United States Patent
Sheikh et al.

(10) Patent No.: US 9,945,863 B2
(45) Date of Patent: Apr. 17, 2018

(54) COILED COIL HELIX CRISTAE MORPHOLOGY 1 (CHCM1) TUMOR MARKER AND CANCER THERAPEUTIC TARGET

(71) Applicant: The Research Foundation of State University of New York, Albany, NY (US)

(72) Inventors: M. Saeed Sheikh, Manlius, NY (US); Ying Huang, Manlius, NY (US); Jie An, Temple, TX (US)

(73) Assignee: The Research Foundation of State University of New York, Albany, NY (US)

(*) Notice: Subject to any disclaimer, the term of this patent is extended or adjusted under 35 U.S.C. 154(b) by 394 days.

(21) Appl. No.: 14/107,306

(22) Filed: Dec. 16, 2013

(65) Prior Publication Data

US 2014/0170241 A1    Jun. 19, 2014

Related U.S. Application Data

(60) Provisional application No. 61/737,527, filed on Dec. 14, 2012.

(51) Int. Cl.
G01N 33/574    (2006.01)
(52) U.S. Cl.
CPC ... *G01N 33/57415* (2013.01); *G01N 33/5743* (2013.01); *G01N 33/57419* (2013.01); *G01N 33/57484* (2013.01)
(58) Field of Classification Search
None
See application file for complete search history.

(56) References Cited

PUBLICATIONS

An et al. In Journal of Biological Chemistry 287(10) 7411-7426 (2012).*
MedicineNet.com (http://www.medterms.com, 2004.*
Diamandis, E.P. in J Natl Cancer Inst 2010;102:1-6.*
Fisher et al. in Cancer Management and Research 4:243-252 (2012).*
Daponte et al. in Anticancer Research 25:1441-1448 (2005).*
Curtin, John A. et al., "Distinct Sets of Genetic Alterations in Melanoma," 2005 N Engl J Med, 2005 vol. 353, No. 20, pp. 2135-2147.
Takata, Minoru et al., "Molecular pathogenesis of malignant melanoma: a different perspective from the studies of melanocytic nevus and acral melanoma," 2009 Pigment Cell Melanoma Res. vol. 23, pp. 64-71.
Moan, Johan et al., "Time trends and latitude dependence of uveal and cutaneous malignant melanoma induced by solar radiation," 2010 Dermato-Endocrinology, vol. 2, No. 1, pp. 3-8.
Yun, Jina et al., "KIT amplification and gene mutations in acral/mucosal melanoma in Korea," 2011 The Authors, APMIS, vol. 119, pp. 330-335.
Kong, Yan et al., "Large-Scale Analysis of KIT Aberrations in Chinese Patients with Melanoma," 2011 Clin Cancer Res, vol. 17, No. 7, pp. 1684-1691.
Singh, Sandeep et al., "Rb-Raf-1 Interaction Disruptor RRD-251 Induces Apoptosis in Metastatic Melanoma Cells and Synergizes with Dacarbazine," 2010 Mol Cancer Ther, vol. 9, No. 12, pp. 3330-3341.
Eggermont, Alexander M.M. et al., "Re-evaluating the role of dacarbazine in metastatic melanoma: what have we learned in 30 years,?" 2004 European Journal of Cancer, vol. 40, pp. 1825-1836.
Daponte, Antonio et al., "Temozolomide and Cisplatin in Advanced Malignant Melanoma," 2005 Anticancer Research vol. 25, pp. 1441-1448.
Baudy, Andreas R. et al, "FDG-PET is a good biomarker of both early response and acquired resistance in BRAF$^{V600}$ mutant melanomas treated with vemurafenib and the MEK inhibitor GDC-0973," 2012 EJNMMI Research, vol. 2, No. 22 (10 pages).
Czarnecka, Anna M. et al., "Cancer as a 'Mitochondriopathy'," 2007 Journal of Cancer Molecules, vol. 3, No. 3, pp. 71-79.
Toyokuni, Shinya et al., "Persistent oxidative stress in cancer," 1995 FEBS Letters 358, pp. 1-3.
Warburg, Otto, "On the Origin of Cancer Cells," 1956 Science, vol. 123, No. 3191, pp. 309-314.
Carew, Jennifer S. et al., "Mitochondrial defects in cancer," 2002 Molecular Cancer, vol. 1, No. 9 (12 pages).
Zick, Michael et al., "Cristae formation—linking ultrastructure and function of mitochondria," 2009 Biochimica et Biophysica Acta, vol. 1793 pp. 5-19.
Frezza, Christian et al., "OPA1 Controls Apoptotic Cristae Remodeling Independently from Mitochondrial Fusion," 2006 Cell, vol. 126, pp. 177-189.
Cipolat, Sara et al., "Mitochondrial Rhomboid PARL Regulates Cytochrome c Release during Apoptosis via OPA1-Dependent Cristae Remodeling," 2006 Cell, No. 126, pp. 163-175.
Gottlieb, Eyal, "OPA1 and PARL Keep a Lid on Apoptosis," 2006 Cell, vol. 126, pp. 27-29.
John, George B. et al., "The Mitochondrial Inner Membrane Protein Mitofilin Controls Cristae Morphology," 2005 Molecular Biology of the Cell, vol. 16, pp. 1543-1554.
Oka, Toshihiko et al., "Identification of a Novel Protein MICS1 that is Involved in Maintenance of Mitochondrial Morphology and Apoptotic Release of Cytochrome c," 2008 Molecular Biology of the Cell, vol. 19, pp. 2597-2608.

(Continued)

*Primary Examiner* — Dennis Heyer
(74) *Attorney, Agent, or Firm* — Harris Beach PLLC

(57) ABSTRACT

Methods for diagnosing and treating a cancer or a tumor in a patient are provided. The methods can comprise the steps of obtaining a biological sample from the patient and analyzing the sample for the presence or absence of Coiled Coil Helix Cristae Morphology 1 protein (CHCM1). A patient is diagnosed with cancer or a tumor provided that CHCM1 is overexpressed. The diagnosed patient is treated by administering a cancer or tumor treatment. The methods can also comprise the steps of obtaining a sample of cancer or tumor cells from the patient, determining a level of CHCM1 expression in the sample of cancer or tumor cells, and administering to the patient a compound for reducing the expression of CHCM1 or for blocking or inhibiting function of CHCM1.

13 Claims, 30 Drawing Sheets

(56) References Cited

PUBLICATIONS

Figure 5B:
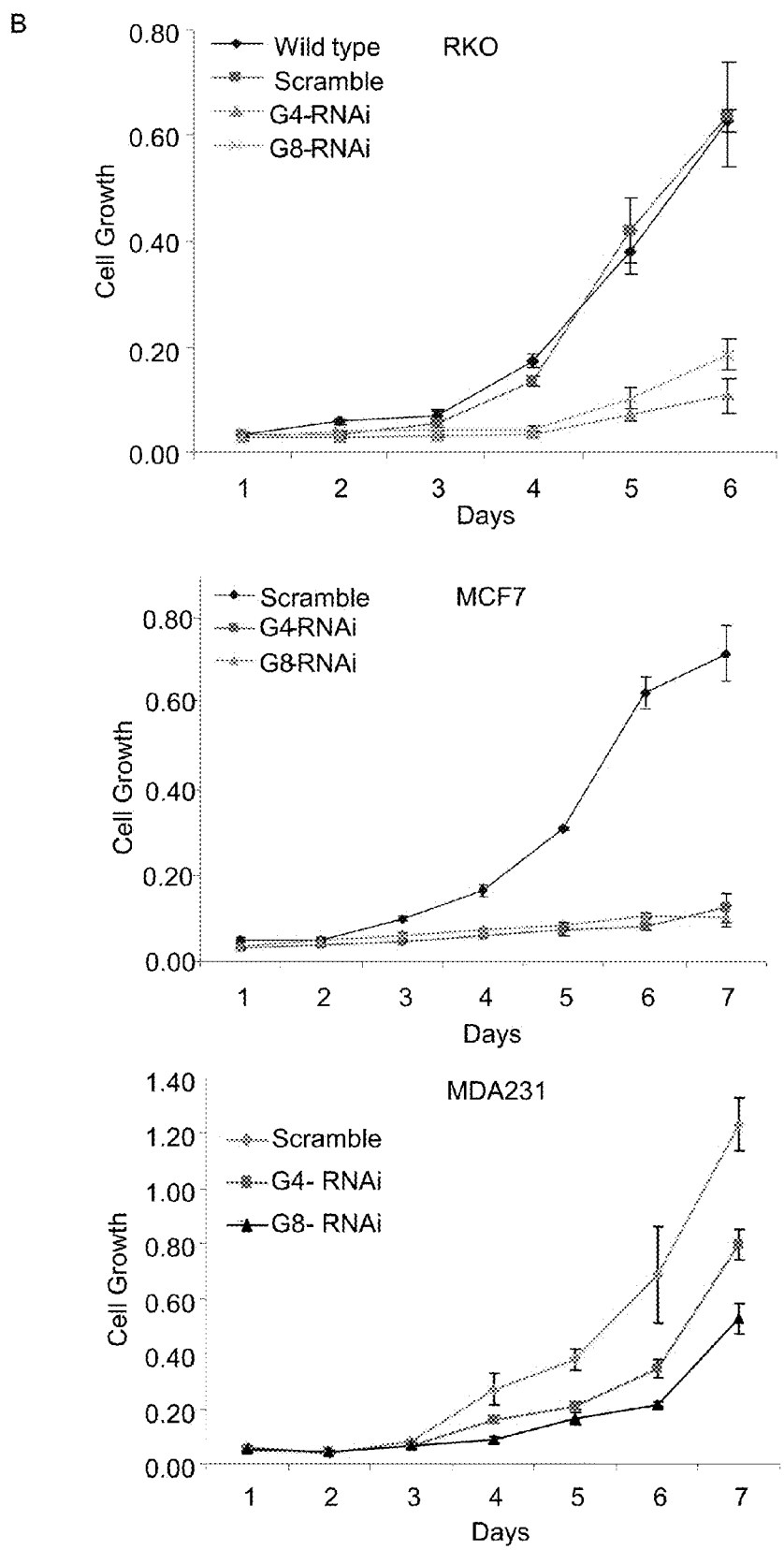

Park, Young-Un et al., "Disrupted-in-schizophrenia 1 (DISC1) plays essential roles in mitochondria in collaboration with Mitofilin," 2010 PNAS, vol. 107, No. 41, pp. 17785-17790.

Darshi, Manjula et al., "ChChd3, an Inner Mitochondrial Membrane Protein, Is Essential for Maintaining Crista Integrity and Mitochondrial Function," 2011 J Biol. Chem., vol. 286, No. 4, pp. 2918-2932.

Mondorf, K., et al. "Screening of combinatorial peptide libraries: Identification of ligands for affinity purification of proteins using a radiological approach", 1998, J. Peptide Res, 52 (pp. 526-536).

Bouchard, P.R., et al. "Discovery and Development of Therapeutic Aptamers," 2010 Annu. Rev. Pharmacol. Toxicol. 50:237-57.

"Systematic evolution of ligands by exponential enrichment", https://en.wikipedia.org/wiki/Systematic_evolution_of_ligands_by_exponential_enrichment, last visited Apr. 26, 2017 (4 pages).

\* cited by examiner

A
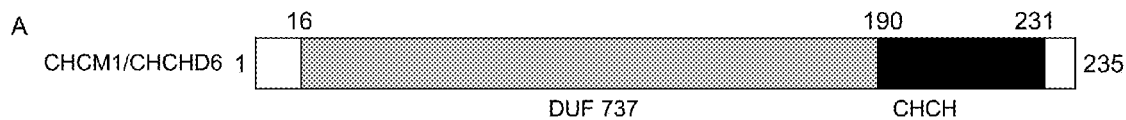
```
MGSTESSEGR RVSFGVDEEE RVRVLQGVRL SENVVNRMKE PSSPPPAPTS STFGLQDGNL
RAPHKESTLP RSGSSGGQQP SGMKEGVKRY EQEHAAIQDK LFQVAKRERE AATKHSKASL
PTGEGSISHE EQKSVRLARE LESREAELRR RDTFYKEQLE RIERKNAEMY KLSSEQFHEA
ASKMESTIKP RRVEPVCSGL QAQILHCYRD RPHEVLLCSD LVKAYQRCVS AAHKG
                     CX₉C                    CX₉C
                          CHCH domain
```
B
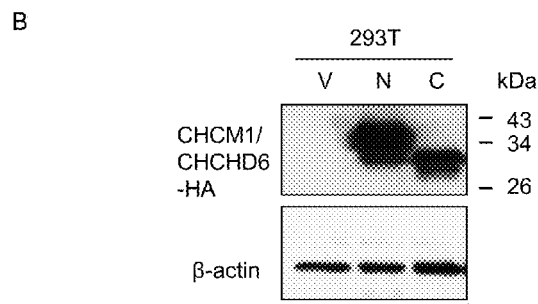
FIGS. 1A-B A      Detection of Exogenous CHCM1/CHCHD6
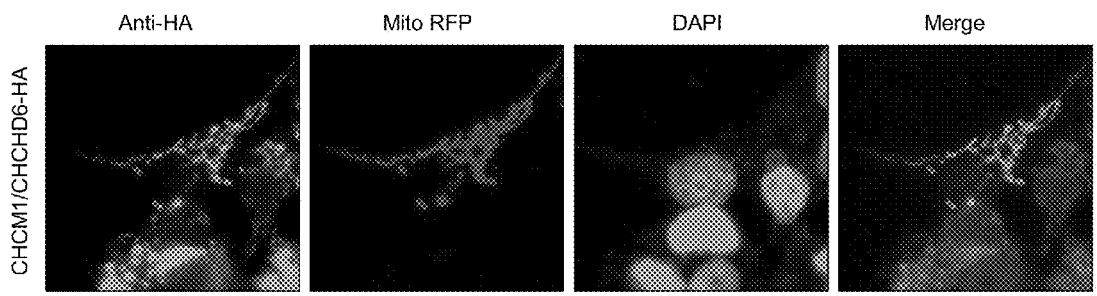
B      Detection of Endogenous CHCM1/CHCHD6
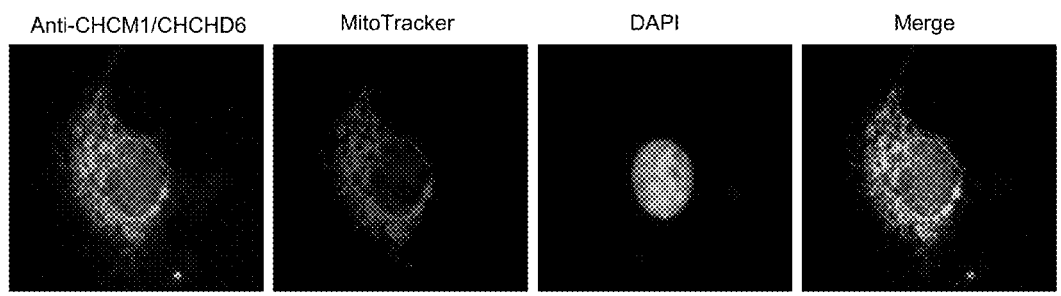
C
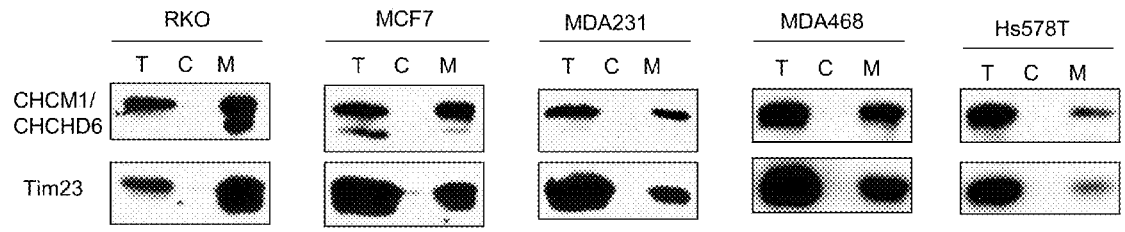
FIGS. 2A-C

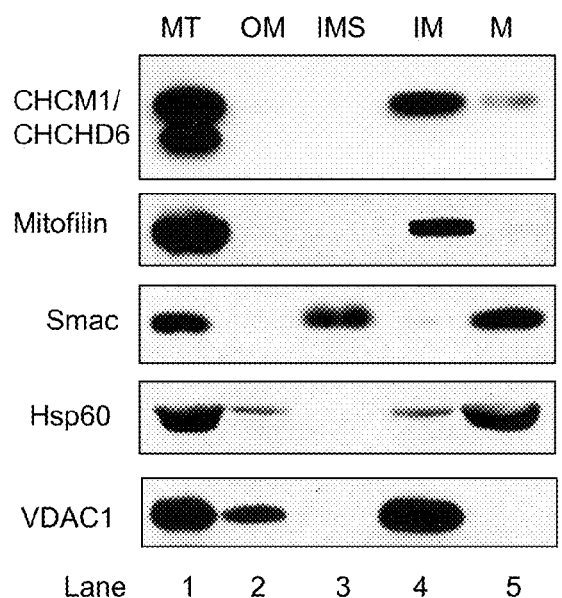
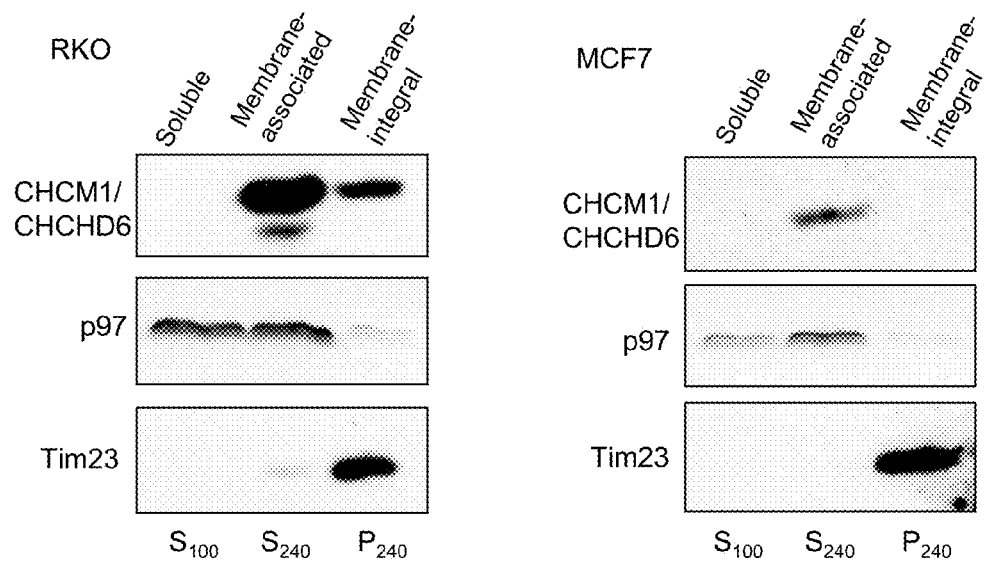
FIGS. 3A-B

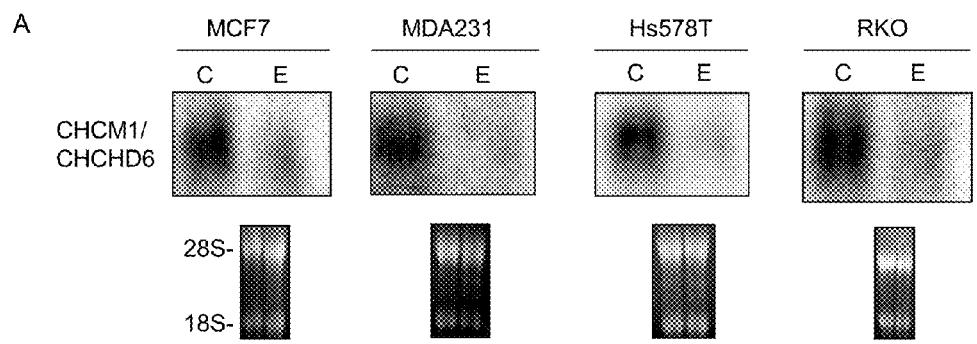
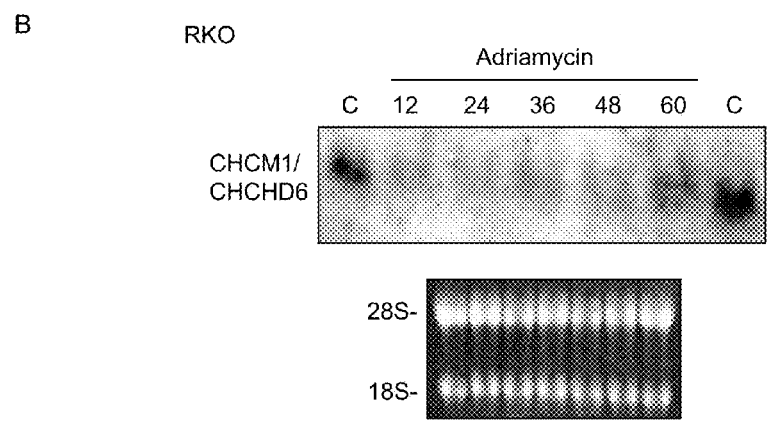
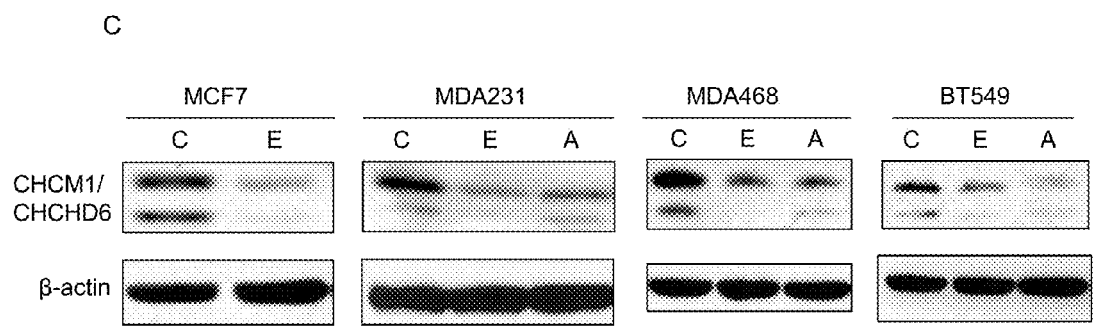
FIGS. 4A-C

A
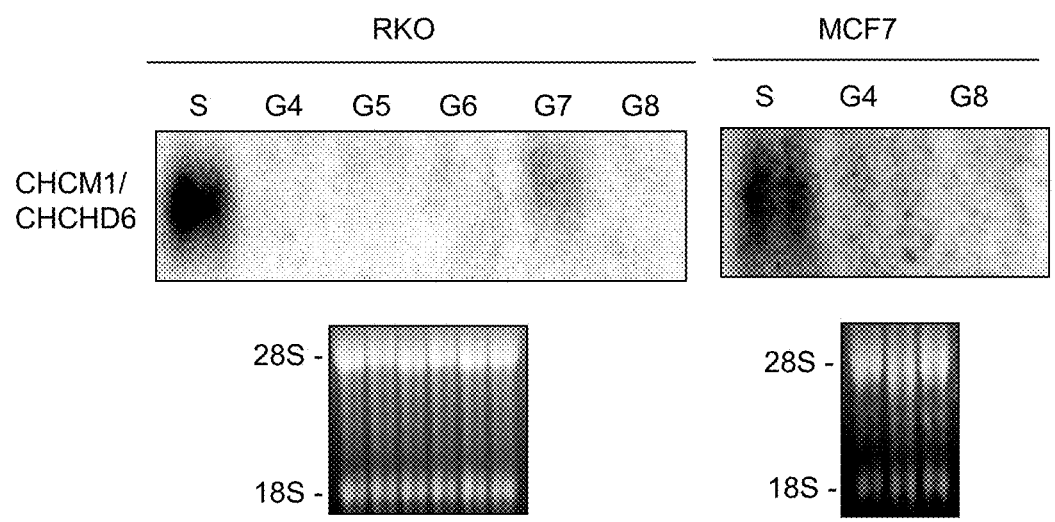
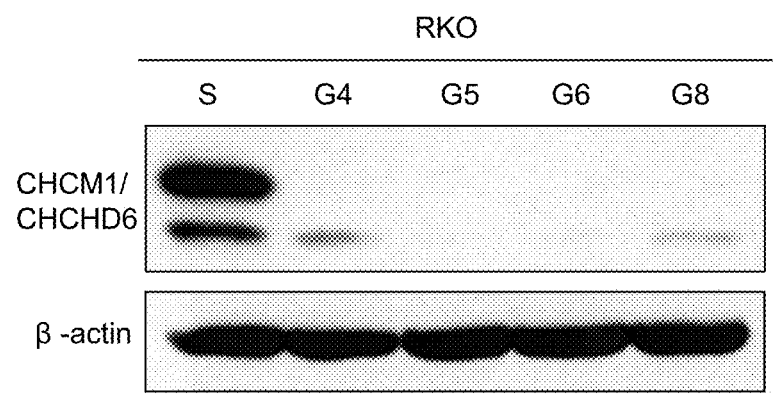
FIG. 5A

A

A
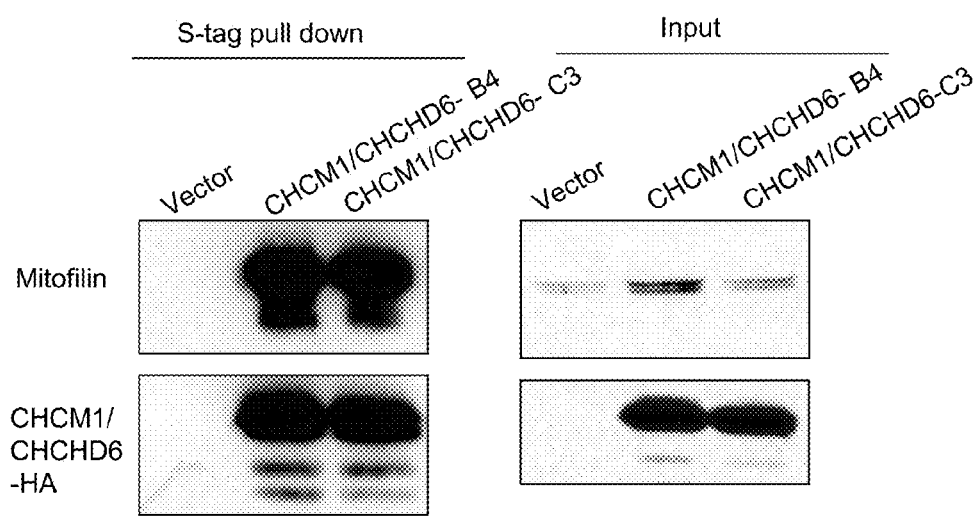
B
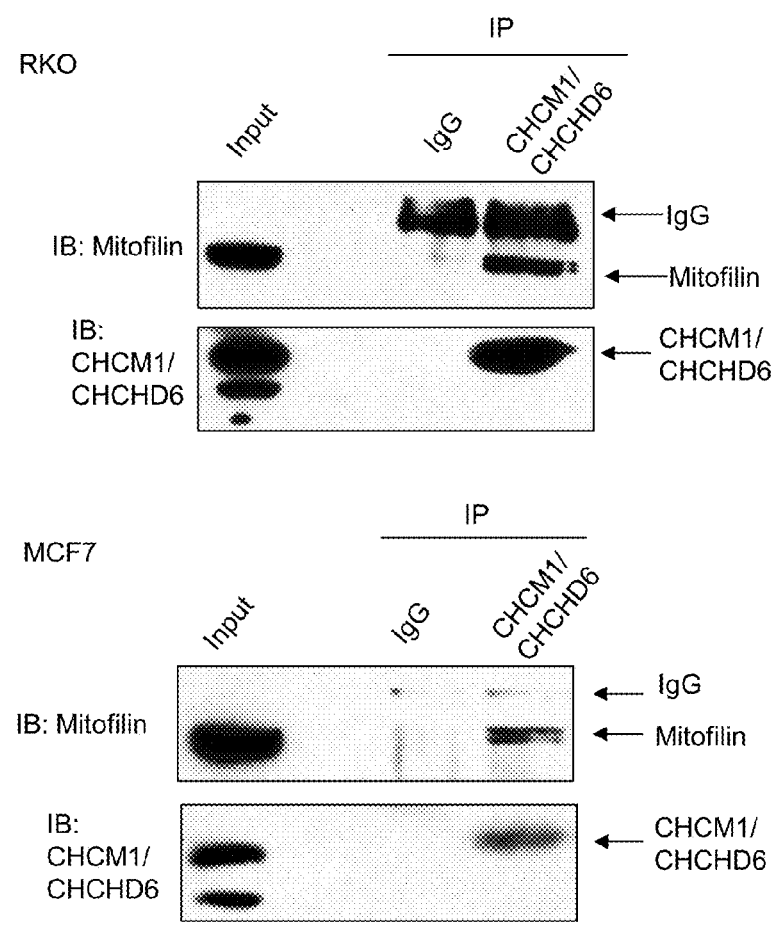
FIGS. 7A-B

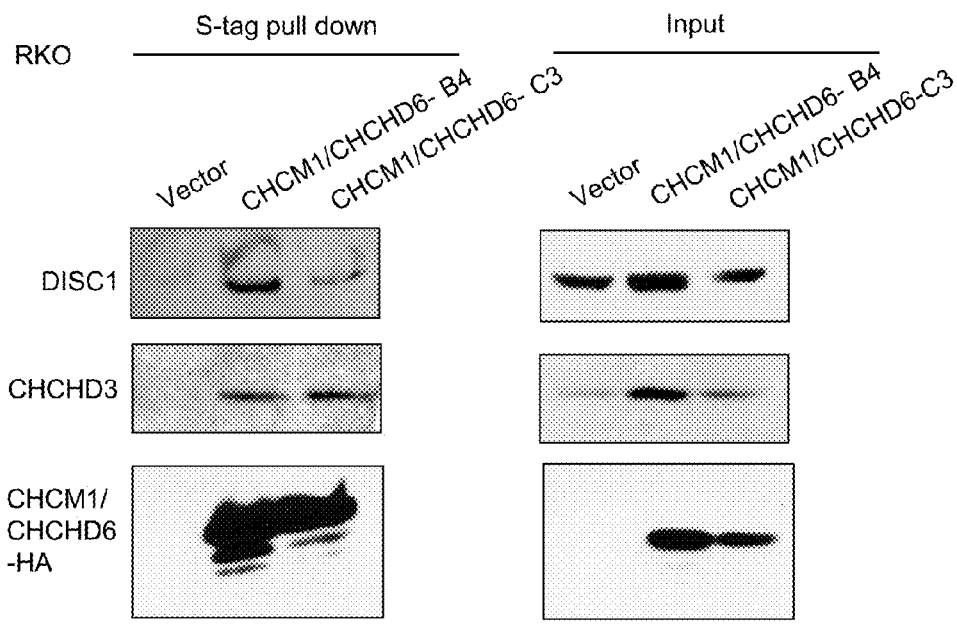
FIGS. 7C-D

A
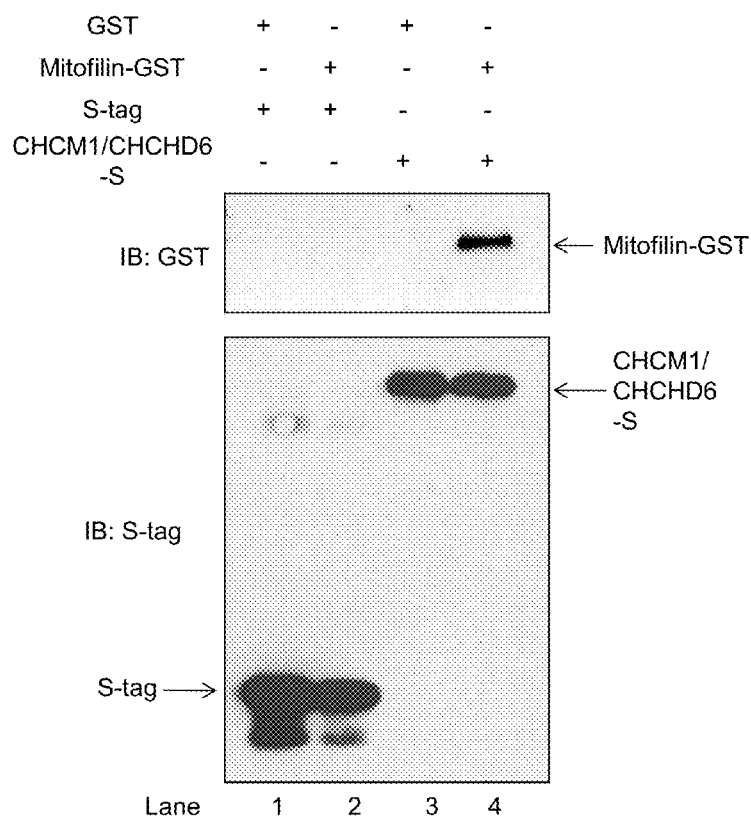
B
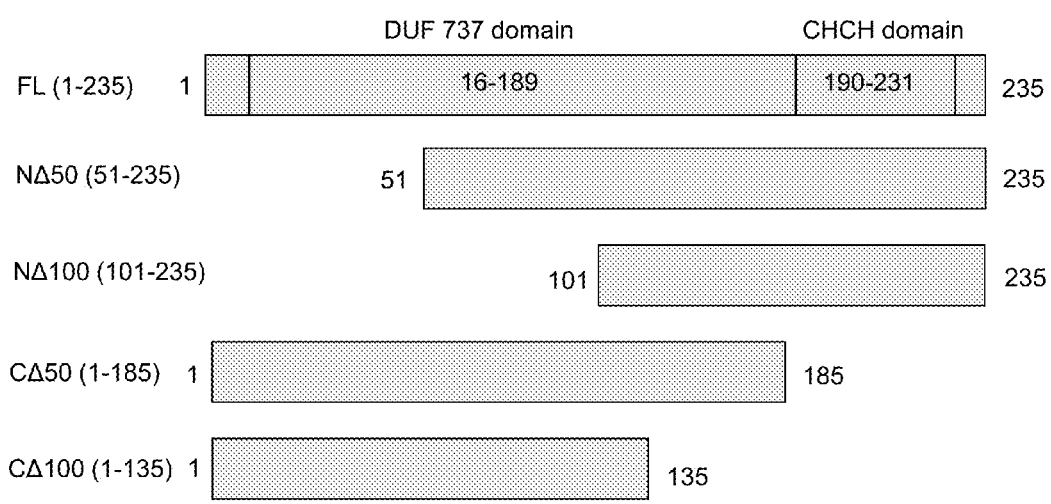
FIGS. 9A-B

C.
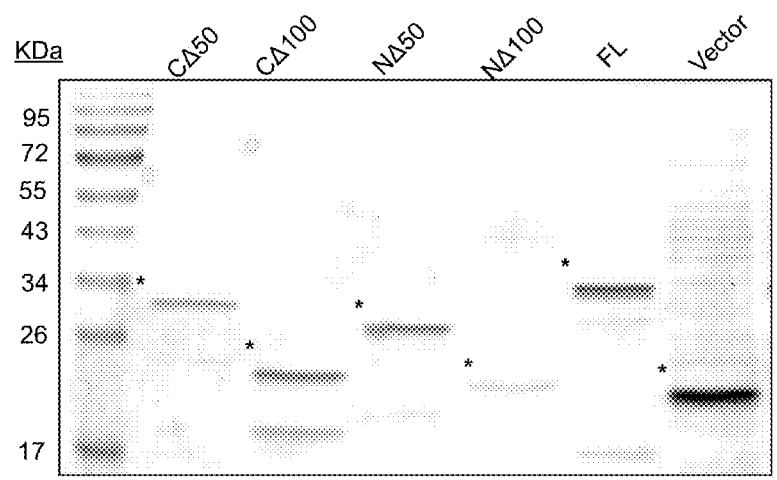
D.
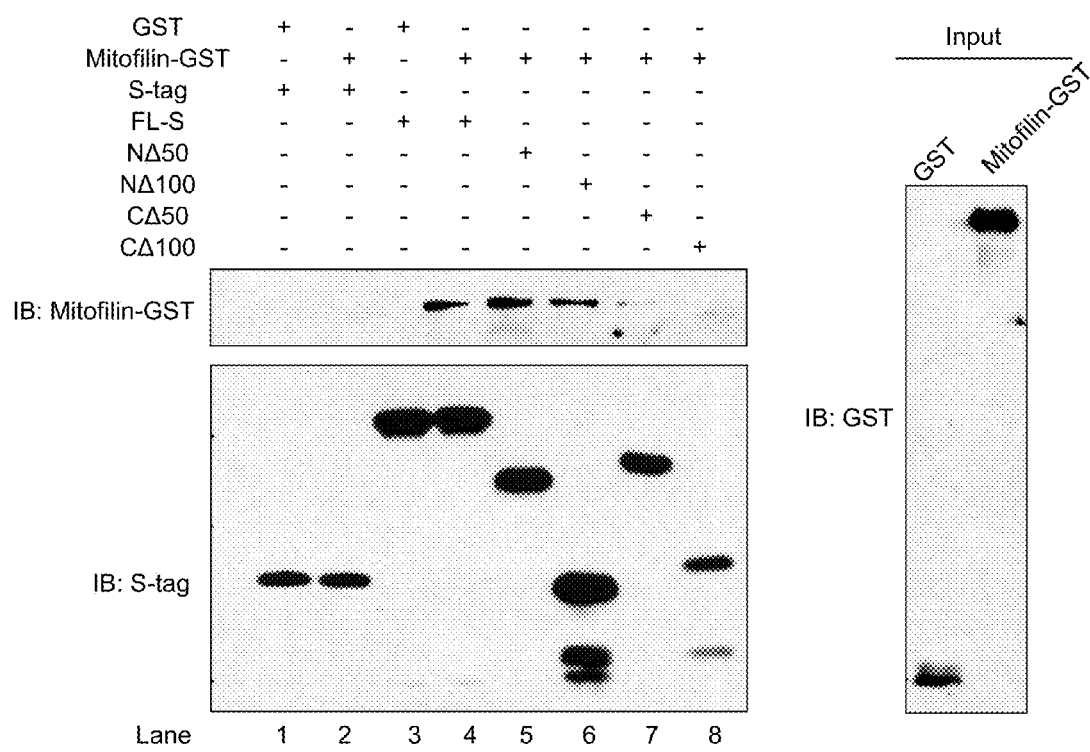
FIGS. 9C-D

A
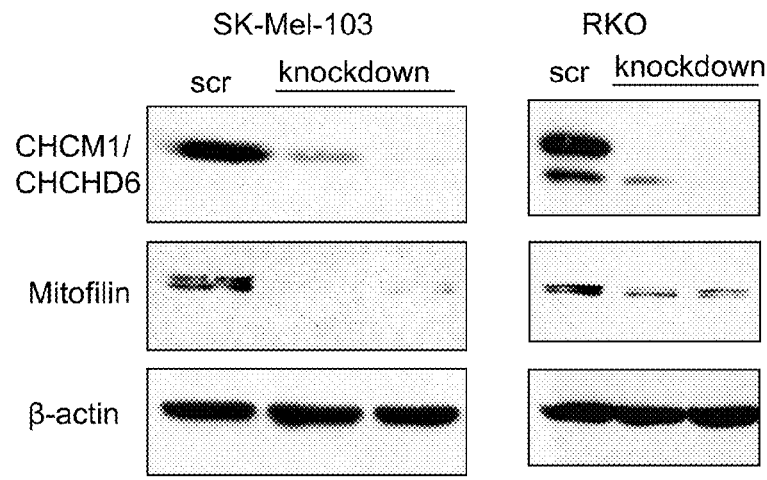
B
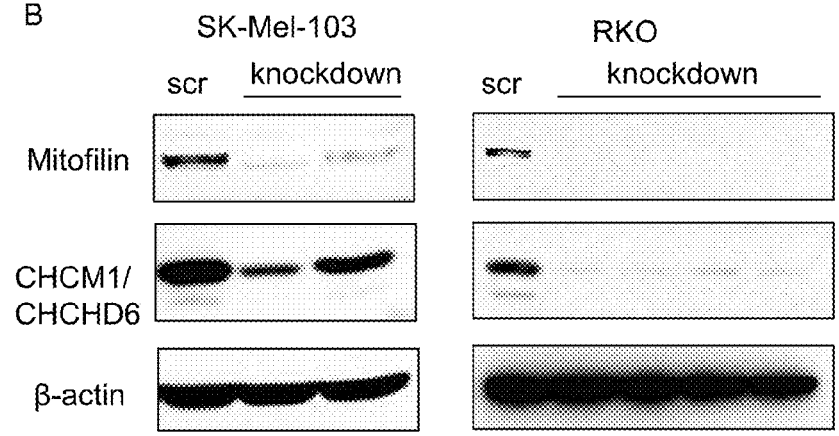
C
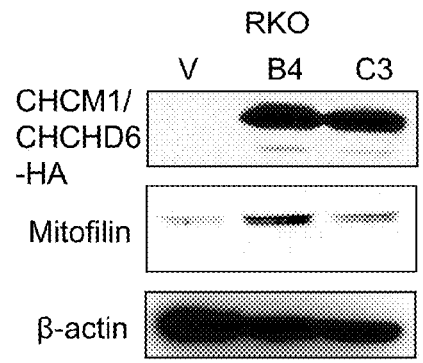
FIGS. 10A-C

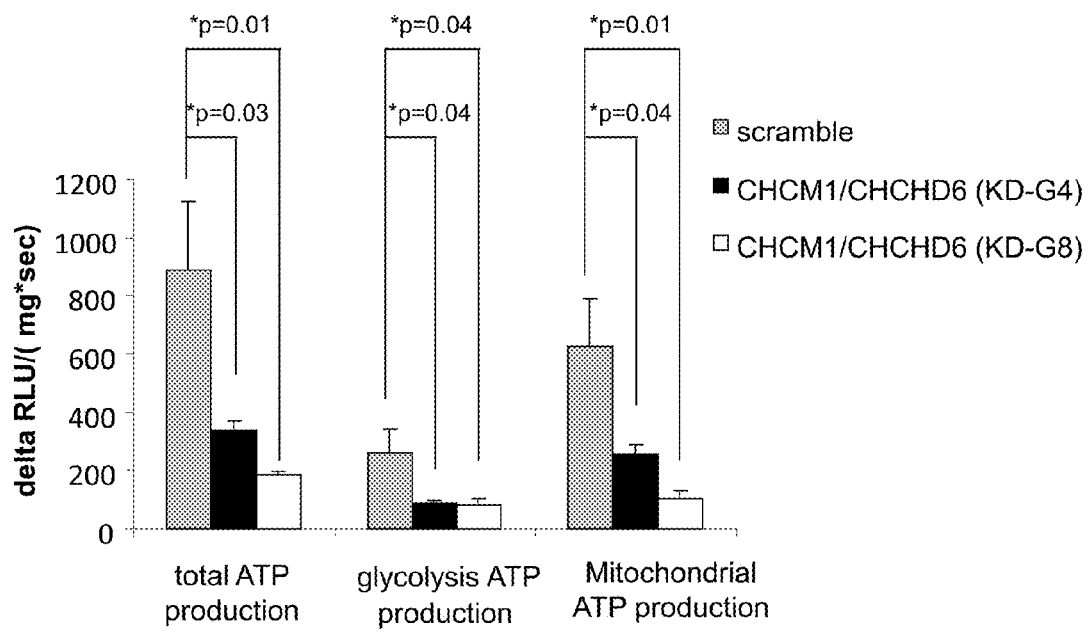
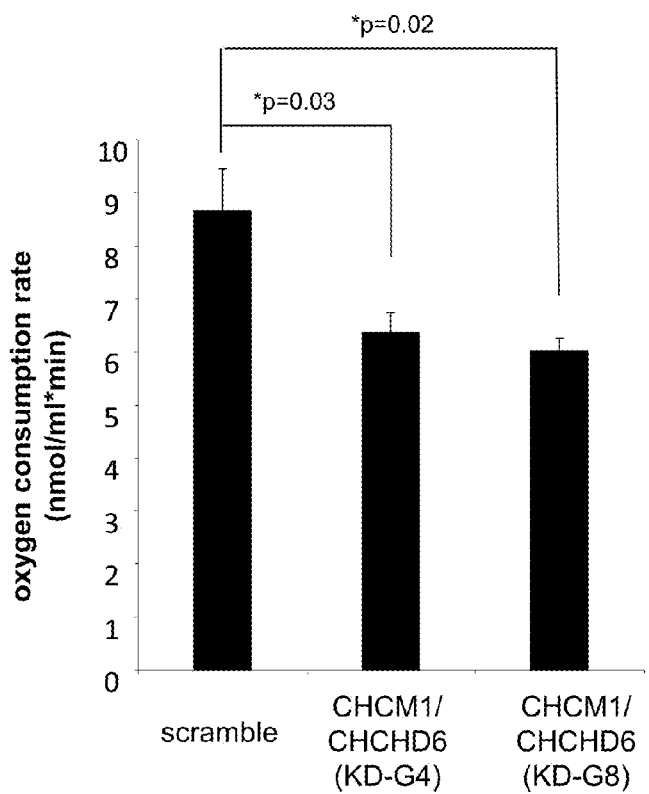
FIGS. 11A-B

A
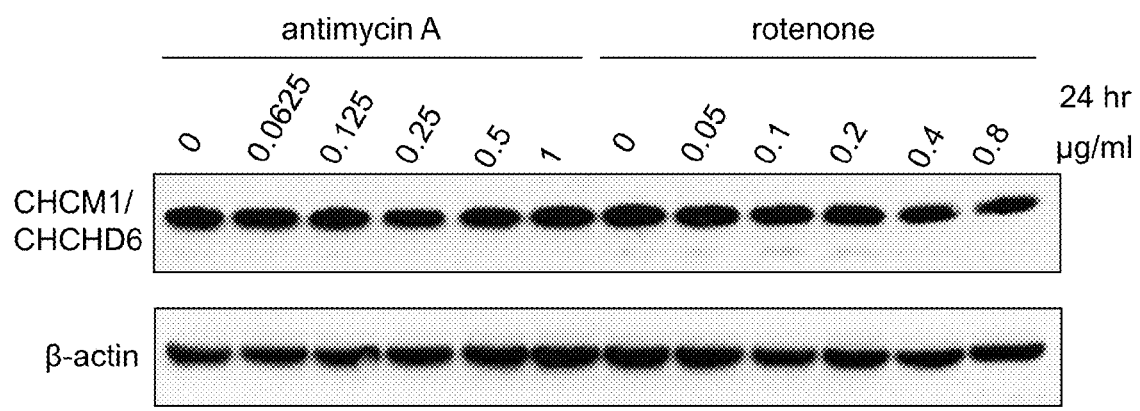
B
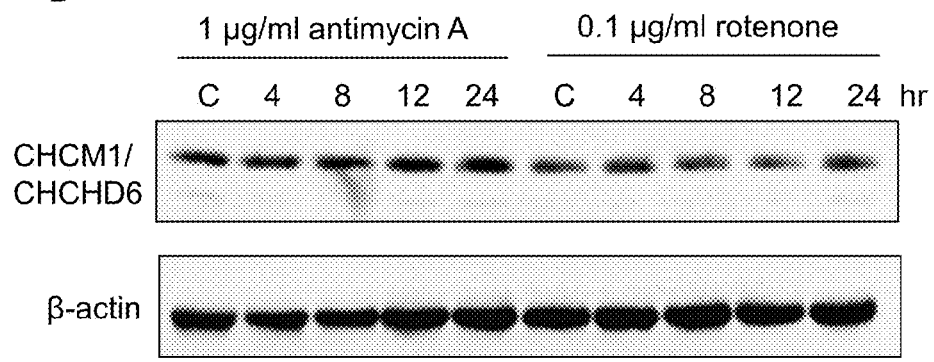
FIGS. 12A-B

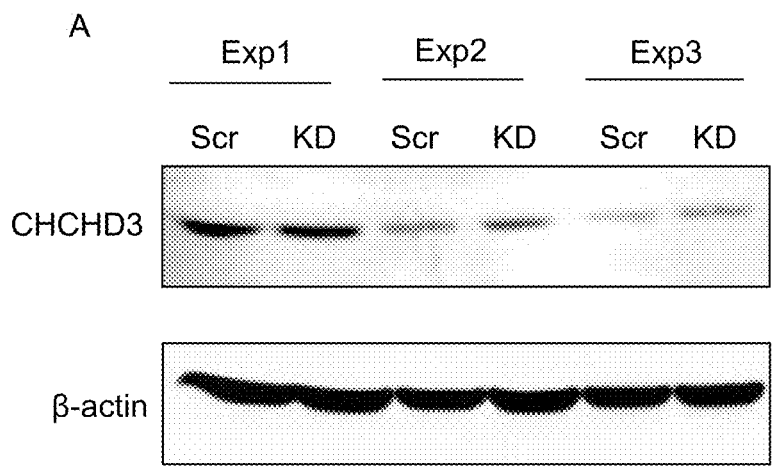
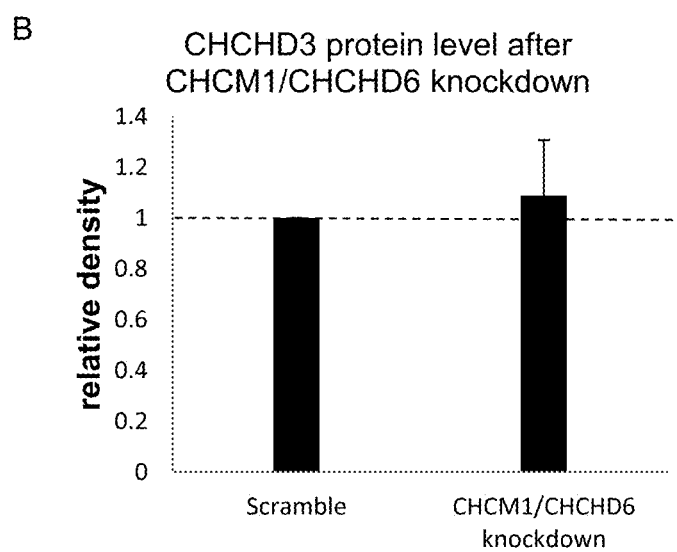
FIGS. 13A-B

| Patient No. | Age (yrs) | Sex | Tumor Type | Tumor Stage |
|---|---|---|---|---|
| P12549/00 | 49 | Female | Malignant melanoma | I; T2N0M0 |
| P7619/00 | 45 | Female | Malignant melanoma | III; T4N0M0 |
| P7683/00 | 73 | Male | Malignant melanoma | III; T4N0M0 |
| C134 | 58 | Male | Malignant melanoma | IV; N/A |
| C161 | 74 | Female | Malignant melanoma | III; T4N0M0 |
| C620T | 40 | Female | Malignant melanoma | III; T4N0M0 |
| C791T | 43 | Female | Malignant melanoma | I; T2N0M0 |

FIG. 16

| CHCM1 staining | Patient No. | Sex | Age | Organ | Pathology diagnosis | Stage | TNM | Type |
|---|---|---|---|---|---|---|---|---|
| 2+ | T382-A1/A5 | F | 65 | Left nasal cavity | Epithelioid malignant melanoma | I | — | Malignant |
| 4+ | T382-A2/A6 | F | 77 | Skin | Epithelioid malignant melanoma of left sole | II | T4N0M0 | Malignant |
| 1+ | T382-A3/A7 | M | 75 | Rectum | Plasmacytoid malignant melanoma (fibrofatty tissue, blood vessel and peripheral nerve) | I | — | Malignant |
| 2+ | T382-A4/A8 | F | 79 | Vulva | Plasmacytoid malignant melanoma | III | T4N1M0 | Malignant |
| 1+ | T382-B1/B5 | M | 36 | Skin | Balloon cell malignant melanoma of left chest wall | II | T4N0M0 | Malignant |
| 3+ | T382-B2/B6 | F | 42 | Skin | Balloon cell malignant melanoma of right thigh | II | T4N0M0 | Malignant |
| 3+ | T382-B3/B7 | F | 52 | Rectum | Rhabdoid malignant melanoma | I | — | Malignant |
| +/− | T382-B4/B8 | M | 63 | Nose | Perivascular cell malignant melanoma | I | — | Malignant |
| 3+ | T382-C1/C5 | M | 60 | Skin | Sarcomatoid malignant melanoma of left buttocks | III | T4N1M0 | Malignant |
| 2+ | T382-C2/C6 | M | 55 | Skin | Sarcomatoid malignant melanoma of left buttocks | II | T4N0M0 | Malignant |
| 3+ | T386-A1/A2/A5/A6 | F | 75 | Skin | Malignant melanoma of left arm | II | T2N0M0 | Malignant |
| 3+ | T386-A3/A4/A7/A8 | M | 74 | Skin | Malignant melanoma of left foot | II | T4N0M0 | Malignant |

FIG. 19A

| CHCM1 | Patient No. | Sex | Age | Organ | Pathology diagnosis | Stage | TNM | Type |
|---|---|---|---|---|---|---|---|---|
| 0 | T386-B1/B2/B5/B6 | M | 51 | Skin | Malignant melanoma of chest wall | II | T4N0M0 | Malignant |
| 2+ | T386-B3/B4/B7/B8 | M | 51 | Skin | Malignant melanoma of left arm | III | T4N1M0 | Malignant |
| 4+ | ME242-A1 | F | 40 | Skin | Malignant melanoma of lower jaw bone | II | T4N0M0 | Malignant |
| 3+ | ME242-A2 | F | 75 | Skin | Malignant melanoma of left buttock | I | T2N0M0 | Malignant |
| 4+ | ME242-A5 | F | 60 | Skin | Malignant melanoma of jaw bones | II | T4N0M0 | Malignant |
| 1+ | ME242-A6 | M | 40 | Skin | Malignant melanoma of right chest wall | II | T4N0M0 | Malignant |
| 3+ | ME242-B1 | M | 70 | Oral cavity | Malignant melanoma of right parotid gland and cervical part | – | – | Malignant |
| 2+ | ME242-B2 | M | 71 | Small intestine | Malignant melanoma of small intestine | – | – | Malignant |
| 3+ | ME242-B5 | M | 64 | Esophagus | Malignant melanoma of esophagus | – | – | Malignant |
| 2+ | ME242-B6 | F | 55 | Oral cavity | Malignant melanoma of right gum | – | – | Malignant |
| 2+ | ME242-C1 | F | 40 | Oral cavity | Malignant melanoma of gum of law right jaw bones (tumoral necrosis) | – | – | Malignant |
| 2+ | ME242-C2 | M | 52 | Oral cavity | Malignant melanoma of pars palatalis | – | – | Malignant |
| 2+ | ME242-C5 | F | 36 | Oral cavity | Malignant melanoma of oral cavity | – | – | Malignant |
| 3+ | ME242-C6 | M | 79 | Oral cavity | Malignant melanoma of right maxillary sinus | – | – | Malignant |

FIG. 19B

| staining | | | | | | | |
|---|---|---|---|---|---|---|---|
| Kera: +/-<br>Melano: - | T382-C3/C7 | M | 25 | Skin | Normal skin tissue | - | Normal |
| Kera: +/-<br>Melano: +/- | T382-C4/C8 | M | 35 | Skin | Normal skin tissue | - | Normal |
| Kera: +/-<br>Melano: - | T386-C1/C2/C5/C6 | F | 50 | Skin | Normal skin tissue | - | Normal |
| Kera: +/-<br>Melano: - | T386-C3/C4/C7/C8 | F | 16 | Skin | Normal skin tissue | - | Normal |
| Kera: +<br>Melano: +/- | ME242-A3 | M | 35 | Skin | Adjacent normal skin tissue | - | NAT |
| Kera: +<br>Melano: - | ME242-A4 | F | 40 | Skin | Normal skin tissue of scalp | - | Normal |
| Kera: +/-<br>Melano: - | ME242-A7 | F | 40 | Skin | Adjacent normal skin tissue of abdominal part | - | Normal |
| Kera: +/- | ME242-A8 | F | 62 | Skin | Normal skin tissue (sparse) | - | NAT |

FIG. 19C

| Melano: +/- | | | | | | |
|---|---|---|---|---|---|---|
| Kera: +/-<br>Melano: - | ME242-B3 | M | 45 | Skin | Adjacent normal skin tissue of scalp (hair follicle and sebaceous glands tissue) | – | – | NAT |
| Kera: +/-<br>Melano: - | ME242-B4 | F | 57 | Skin | Adjacent normal skin tissue of scalp | – | – | NAT |
| Kera: +/-<br>Melano: - | ME242-B7 | M | 19 | Skin | Normal skin tissue of abdominal part | – | – | Normal |
| Kera: +/-<br>Melano: - | ME242-B8 | F | 51 | Skin | Adjacent normal skin tissue of left upper quadrant of the abdomen (sparse) | – | – | NAT |
| Kera: +/-<br>Melano: - | ME242-C3 | F | 49 | Skin | Adjacent normal skin tissue | – | – | NAT |
| Kera: +/-<br>Melano: - | ME242-C4 | M | 31 | Skin | Ajacent normal skin tissue of femoribus internus | – | – | NAT |
| Kera: +/-<br>Melano: - | ME242-C7 | F | 42 | Skin | Adjacent normal skin tissue of left breast | – | – | NAT |
| Kera: + | ME242-C8 | F | 45 | Skin | Adjacent normal skin tissue of scalp (sparse) | – | – | NAT |

FIG. 19D

| Tissue type | Number of samples | Staining intensity | | | | | |
|---|---|---|---|---|---|---|---|
| | | Negative (0) | Weak (+/-) | Weak (1+) | Moderate (2+) | Strong (3+) | Very strong (4+) |
| Melanoma | 26 | 3.85% (1/26) | 3.85% (1/26) | 11.54% (3/26) | 34.62% (9/26) | 34.62% (9/26) | 11.54% (3/26) |
| Normal | 16 | 75% (12/16) | 25% (4/16) | | | | |

FIG. 20

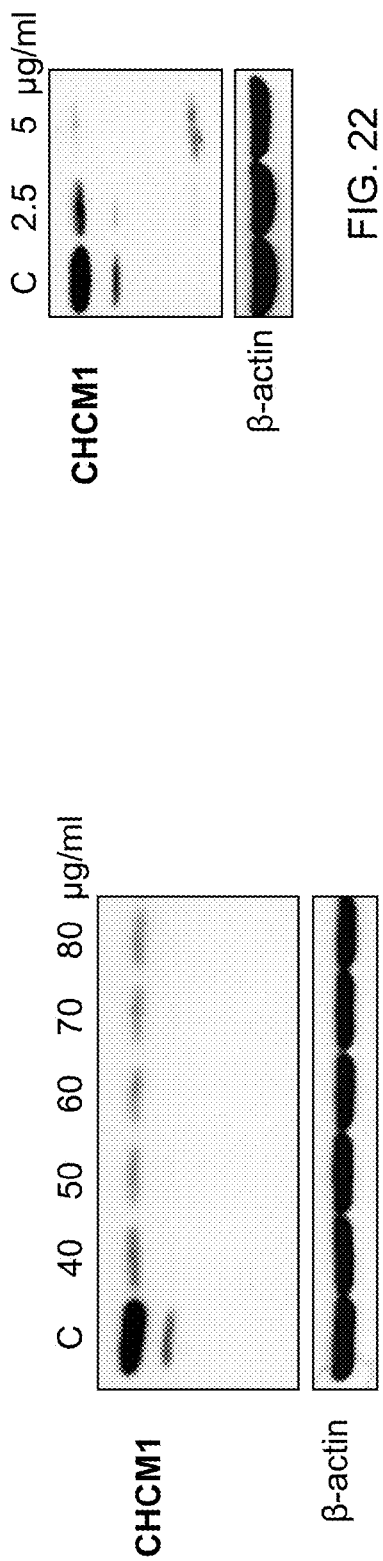
FIG. 21
FIG. 22
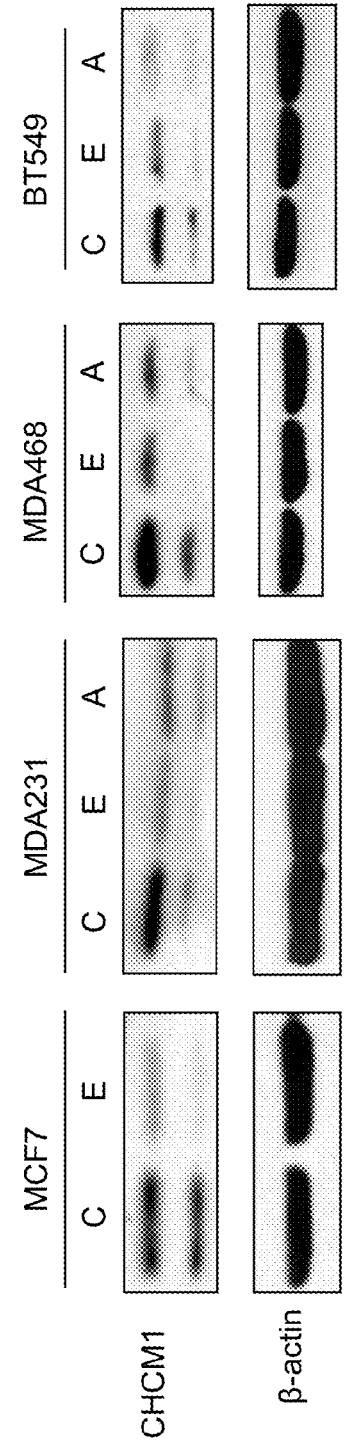
FIG. 23

COILED COIL HELIX CRISTAE MORPHOLOGY 1 (CHCM1) TUMOR MARKER AND CANCER THERAPEUTIC TARGET

CROSS-REFERENCE TO RELATED APPLICATIONS

This application claims priority to and the benefit of U.S. provisional patent application Ser. No. 61/737,527, entitled "CHCM1, A Novel Tumor Marker and Cancer Therapeutic Target," filed Dec. 14, 2012, which is incorporated herein by reference in its entirety.

STATEMENT REGARDING FEDERALLY SPONSORED RESEARCH OR DEVELOPMENT

The disclosed invention was made with government support under contract nos. CA157168 and ES016668 from the National Institutes of Health. The government has rights in this invention.

1. TECHNICAL FIELD

The present invention relates to biomarkers for cancer and tumors, particularly biomarkers for malignant melanoma. The invention also relates to cancer therapeutic targets, particularly malignant melanoma targets.

2. BACKGROUND OF THE INVENTION

Cancer is one of the leading causes of deaths worldwide. In the US alone, more than 1 million cases of various types of cancers are diagnosed each year and more than half million people die due to cancer. Accurate and early diagnosis and treatment of cancer is paramount to improve survival and quality of life. Tumor markers with diagnostic and prognostic significance can help achieve these goals and because tumors exhibit significant tumor heterogeneity, therefore, multiple tumor markers can facilitate accurate and early detection. Also, within a tumor type, one or more tumor markers can serve to sub-classify a subset of tumor and predicts its behavior. Thus, cancer markers that can facilitate accurate cancer diagnosis in general and detection at early stages in particular are urgently needed for all types of cancers. In this context, genes and their protein products differentially expressed between normal and cancer tissues have the potential to serve as important tumor markers. One of the major problems in cancer therapeutics is that the existing cancer drugs affect cancer as well as normal cells. Therefore, better therapeutic approaches are urgently needed to selectively target cancer cells but spare normal cells. In this regard, tumor markers as cancer-specific molecules linked to cancer cell growth and survival can provide very valuable insight into developing newer therapeutic strategies. For example, molecules with anti-tumor potential whose expression is deregulated in cancers can serve as important cancer diagnostic and prognostic markers on the one hand and targets to develop novel cancer therapeutics on the other. These molecules with diagnostic and prognostic potential can also predict patients' response to therapy.

Exposure to environmental agent such as UV radiation has also been linked to melanoma development. Melanoma is considered to be the highly aggressive malignancy affecting the skin (see ref. 1 and references cited therein). Melanoma arises in melanocytes and can be classified into various types including cutaneous, acral, mucosal and uveal melanomas (1). The cutaneous type is the most common and affects skin and has a predominant association with exposure to UV (1-3). This variety can be further subdivided into chronic sun-damage (CSD) melanoma and non-chronic sun-damage (non-CSD) melanoma (2, 3). The acral type affects skin of palms, soles and the area underneath fingernails or toenails. As the name implies, the mucosal variety occurs in mucosal tissues whereas the uveal type affects melanocytes in other organs for example, in iris of the eye. It is believed that the acral, mucosal and uveal types are not linked to UV exposure (1-3). Although the molecular pathogenesis of malignant melanoma remains to be fully investigated, mutations in BRAF gene that encodes a serine threonine kinase have been found in approximately 45% of the cases (1) of cutaneous (non-CSD) melanoma. In the case of mucosal, uveal and CSD varieties, the incidence of BRAF mutations is reported to be lower. Point mutations in NRAS have also been reported for non-CSD melanoma, while aberrations in KIT receptor tyrosine kinase have been found in CSD, mucosal and acral types of melanomas (1). Not all melanomas, however, harbor mutations in BRAF or NRAS or aberrations in KIT receptor-mediated signaling (4, 5). Therefore, further studies are needed to identify additional molecules that are linked to melanoma development and/or progression. Such molecules are expected to prove very valuable for better understanding of melanoma pathogenesis and can also serve as (i) markers for improved diagnosis and prognosis and (ii) targets to develop novel therapeutics.

Further approaches to manage melanoma are urgently needed. Dacarbazine (DTIC) is a commonly used anticancer drug for advanced malignant melanoma but response rate remains low and tumors initially responding to drug eventually acquire resistance to DTIC (6, 7). Cisplatin is another anticancer drug and its use in combination with other therapeutics is being explored as an alternative strategy to manage melanoma (8).

More recently, FDA has approved vemurafenib (PLX4032) for the treatment of malignant melanoma that harbor BRAF mutation ($BRAF^{V600E}$ is the most common oncogenic mutation that activates this kinase and about 45-50% of melanoma harbor such mutation) (9, 10). Vemurafenib does not work in melanomas that harbor wild type BRAF. Another limitation of vemurafenib is that some melanomas although harbor BRAF mutation do not respond to vemurafenib (inherent resistance) while others initially respond but later acquire resistance (9, 11, 12). The molecular basis for acquisition to vemurafenib resistance is believed to be multifactorial in nature and remains to be fully investigated (12).

Citation or identification of any reference in Section 2, or in any other section of this application, shall not be considered an admission that such reference is available as prior art to the present invention.

3. SUMMARY OF THE INVENTION

A method is provided for diagnosing and treating a cancer or a tumor in a patient comprising the steps of:
obtaining a biological sample from a patient,
analyzing the sample for the presence or absence of Coiled Coil Helix Cristae Morphology 1 protein (CHCM1), wherein the patient is diagnosed with the cancer or the tumor if the sample expresses higher levels of CHCM1 compared to normal tissue; and
administering a cancer or a tumor treatment to the diagnosed patient (i.e., provided that the patient is diagnosed with the cancer or the tumor).

In one embodiment of the method, the cancer or tumor is breast cancer, colon cancer or melanoma.

In another embodiment of the method, the biological sample can be a cell or tissue sample such as a sample from a biopsy (e.g., obtained from a patient's suspected cancer or tumor) or a blood sample.

In another embodiment of the method, the step of analyzing the sample for the presence or absence of CHCM1 comprises the step of determining whether CHCM1 is overexpressed, and then administering a cancer (or tumor) treatment to the diagnosed patient provided that CHCM1 is overexpressed.

In another embodiment of the method, the step of analyzing the sample for the presence or absence of CHCM1 comprises the step of performing Western blotting, Northern blotting, dot blotting or PCR-based approaches.

In certain embodiments of the method, overexpression of CHCM1 is 1.5- to 2-fold, 2- to 3-fold, 3- to 5-fold, 5- to 10-fold, or greater than 10-fold greater than normal or wild-type expression of CHCM1.

In another embodiment of the method, quantitatively higher levels of CHCM1 are 1.5 fold and higher compared to corresponding normal tissue. Determination of normal or wild-type expression of CHCM1 can be performed by the skilled artisan using routine methods. Expression may be measured by band intensity (e.g., in a Northern or Western blot), by other measures of expression, or by the intensity of histochemical or immunohistochemical staining.

In another embodiment of the method, the step of administering the cancer treatment to the diagnosed patient comprises the step of administering a therapeutic compound for treating and/or managing the cancer to the patient.

In another embodiment of the method, the therapeutic compound is an anticancer drug including, but not limited to, doxorubicin (ADRIAMYCIN®), etoposide, bendamustine, busulfan, carmustine, chlorambucil, cyclophosphamid, dacarbazine (dtic), ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D/dactinomycin, bleomycin, daunorubicin, epirubicin, idarubicin, mitomycin, mitoxantrone, docetaxel, irinotecan, paclitaxel, topotecan, vinblastine, vincristine, vinorelbine, carboplatin, cisplatin and oxaliplatin.

In another embodiment of the method, the step of administering the cancer treatment to the diagnosed patient comprises the step of administering a compound for reducing the expression of CHCM1 or for blocking or inhibiting function of CHCM1.

In another embodiment of the method, the step of administering the cancer treatment to the diagnosed patient comprises the step of administering a compound for reducing the expression of CHCM1 or for blocking or inhibiting function of CHCM1.

In another embodiment of the method, the compound reducing the expression of CHCM1 or blocking or inhibiting its activity or its interactions with other proteins is a shRNA, siRNA, a peptide, a small molecule (e.g., Cisplatin and DTIC), an antibody, or a large molecule such as such as a full-length protein or a larger fragment of a protein. Smaller fragments (polypeptides) of CHCM1 can also be used to block its interactions with other proteins. For example, small or large CHCM1 mimetics (peptides) can be used which will interact with CHCM1-interacting proteins and thereby inhibit their interactions with CHCM1 (competitive approach).

In another embodiment of the method, the step of administering the cancer treatment to the diagnosed patient comprises the step of down-regulating, inhibiting or blocking the activity of CHCM1, or inhibiting or blocking CHCM1 interactions with other proteins.

In another embodiment of the method, the step of down-regulating, inhibiting or blocking the activity of CHCM1, or inhibiting or blocking CHCM1 interactions with other proteins comprises administering a compound that: down-regulates or inhibits CHCM1, or interferes with or inhibits the functioning of CHCM1 or with CHCM1 interactions with other proteins.

In another embodiment of the method, the compound is a CHCM1 inhibitor. A CHCM1 inhibitor may be any agent that reduces levels of CHCM1 and/or interferes with CHCM1 activity and/or function and/or blocks and/or interferes with CHCM1 interactions with other proteins.

In another embodiment of the method, the step of analyzing the sample comprises the step of performing an assay, wherein the assay comprises the step of determining the level of CHCM1 in the sample.

In another embodiment of the method, the step of determining the level of CHCM1 comprises the step of performing an immunohistochemical staining procedure on the sample, thereby producing a stained sample, wherein the immunohistochemical staining procedure detects CHCM1 expression.

In another embodiment of the method, the method comprises, after the step of performing the immunohistochemical staining procedure, the step of evaluating the stained sample to determine the level of CHCM1.

In another embodiment of the method, the sample is a blood sample, and the step of determining the level of CHCM1 comprises the step of detecting the level of CHCM1 in the blood sample.

In another embodiment of the method, the step of determining the level of CHCM1 comprises the step of detecting the level of mRNA for CHCM1 in the sample A method is provided for diagnosing and treating a cancer or a tumor in a patient comprising the steps of:

obtaining a sample of cancer or tumor cells from the patient, determining a level of CHCM1 expression in the sample of cancer or tumor cells, and administering to the patient a compound for reducing the expression of CHCM1 or for blocking or inhibiting function of CHCM1.

In one embodiment of the method, the method comprises the step of administering to the patient a therapeutic compound for treating and/or managing the cancer or tumor.

In another embodiment of the method, the therapeutic compound is an anticancer drug including, but not limited to, doxorubicin (ADRIAMYCIN®), etoposide, bendamustine, busulfan, carmustine, chlorambucil, cyclophosphamid, dacarbazine (dtic), ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D/dactinomycin, bleomycin, daunorubicin, epirubicin, idarubicin, mitomycin, mitoxantrone, docetaxel, irinotecan, paclitaxel, topotecan, vinblastine, vincristine, vinorelbine, carboplatin, cisplatin and oxaliplatin.

In another embodiment of the method, the therapeutic compound is a CHCM1 inhibitor. A CHCM1 inhibitor may be any agent that reduces levels of CHCM1 and/or interferes with CHCM1 activity and/or function and/or blocks and/or interferes with CHCM1 interactions with other proteins.

A method is provided for diagnosing and treating a cancer or a tumor in a patient comprising the steps of:
  obtaining a biological sample from a patient (e.g., a cancer patient);
  testing the sample for presence of a BRAF mutation; and
  provided that the sample tests positive for presence of a BRAF mutation, administering to the patient vemurafenib.

In one embodiment of the method, the BRAF mutation is V600E. The V600E mutation results in an amino acid substitution at position 600 in BRAF, from a valine (V) to a glutamic acid (E). This mutation occurs within the activation segment of the kinase domain. Approximately 80-90% of V600 BRAF mutations are V600E.

In another embodiment of the method, the method further comprises the steps of: determining a response of the patient to the administered vemurafenib; and, provided that there is a diminished or no response to the administered vemurafenib, administering to the patient a compound for reducing the expression of CHCM1 or for blocking or inhibiting function of CHCM1.

In another embodiment of the method, the diminished response to administered vemurafenib is diminished 10-20%, 20-30%, 30-40%, 40-50%, 50-60%, 60-70%, 70-80%, 80-90% or 90-100% with respect to an established (known in the art or typical) positive response to administered vemurafenib.

In another embodiment of the method, the step of testing the sample for presence of a BRAF mutation comprises determining the nucleotide sequence of the BRAF gene or a fragment thereof from the patient, comparing the determined nucleotide sequence from the patient with wild-type sequence(s) known in the art for the BRAF gene.

Wild-type BRAF gene sequences and mutations of the BRAF gene are well known in the art (see, e.g., H. Davies et al. 2002. Mutations of the BRAF gene in human cancer. Nature 417: 949-954.

A method is provided for diagnosing and treating a cancer or a tumor in a patient is provided comprising the steps of:
  obtaining a biological sample from a cancer patient showing resistance to vemurafenib,
  analyzing the sample for CHCM1 overexpression;
  administering to the patient vemurafenib; and
  administering to the patient a compound for reducing the expression of CHCM1 or for blocking or inhibiting function of CHCM1.

A method is provided for diagnosing and treating a cancer or a tumor in a patient comprising the steps of:
  obtaining a biological sample from a patient:
  testing the sample for presence of a BRAF mutation;
  provided that the sample tests negative for presence of a BRAF mutation or tests wild-type for BRAF;
  administering to the patient a compound for reducing the expression of CHCM1 or for blocking or inhibiting function of CHCM1.

A method is provided for diagnosing a cancer or a tumor in a patient comprising the steps of:
  obtaining a biological sample from a patient,
  analyzing the sample for the presence or absence of cancer cells or tumor cells by measuring the presence or absence of CHCM1,
wherein the patient is diagnosed with the cancer or the tumor if a CHCM1-specific staining cell is detected in the sample.

In one embodiment, a CHCM1-specific staining cell is one that stains above the baseline established for normal or for non-cancer or for non-tumor cells. Such baselines for staining may be established using routine methods known in the art.

A method is provided for treating a cancer or a tumor in a patient comprising:
  requesting a test of the patient, wherein the test provides the results of an analysis to determine whether the patient expresses CHCM1; and
  administering a cancer treatment or a tumor treatment to the patient if the patient expresses CHCM1.

A method is provided for diagnosing cancer or a tumor in a patient, wherein the cancer is characterized by the presence of CHCM1 biomarker comprising the steps of:
  i) obtaining a biological sample from a patient;
  ii) applying an antibody specific for CHCM1 biomarker to the sample, wherein presence of the CHCM1 biomarker creates an antibody-CHCM1 biomarker complex;
  iii) applying a detection agent that detects the antibody-CHCM1 biomarker complex; and
  iv) diagnosing cancer or tumor in the patient provided that the detection agent of step iii) is detected.

In one embodiment of the method, the antibody may be a polyclonal or a preferably, a monoclonal antibody specific for CHCM1. Methods for preparing polyclonal and monoclonal antibodies are well known in the art.

A kit is provided for performing a CHCM1 assay comprising a substance that binds to a CHCM1 protein or nucleic acid.

In one embodiment of the kit, the kit comprises an anti-CHCM1 antibody.

4. BRIEF DESCRIPTION OF THE DRAWINGS

The present invention is described herein with reference to the accompanying drawings, in which similar reference characters denote similar elements throughout the several views. It is to be understood that in some instances, various aspects of the invention may be shown exaggerated, enlarged, exploded, or incomplete to facilitate an understanding of the invention.

FIGS. 1A-B. A. Schematic illustration and amino acids sequence of CHCM1/CHCHD6. DUF: Domain of Unknown Function, CHCH: Coiled coil Helix-Coiled Coil Helix domain. Cysteines in the $CX_9C$-$CX_9C$ motif are highlighted in red. B. Expression of exogenous CHCM1/CHCHD6 in HEK293T cells. V: Vector-only, N: HA-S tagged at the N-terminus of CHCM1/CHCHD6, C: HA-S tagged at the C-terminus of CHCM1/CHCHD6. The N-tagged CHCM1/CHCHD6 migrates slower because there are 3 HA-tags.

FIGS. 2A-C. CHCM1/CHCHD6 is a mitochondrial protein. A. Representative fluorescent photomicrographs showing the subcellular distribution of exogenous HA-tagged CHCM1/CHCHD6 (green) and mitochondria-specific RFP (red) in MCF7 cells. B. Representative fluorescent photomicrographs showing the subcellular distribution of endogenous CHCM1/CHCHD6 (green) and MitoTracker staining (red) in uacc62 cells. Cells were also stained with DAPI nuclear stain. C. Subcellular distribution of endogenous CHCM1/CHCHD6 in multiple cell lines. CHCM1/CHCHD6 distribution was determined by cell fractionation method followed by Western blot analyses. T: Total cell lysate, C: Cytosolic fraction, M: Mitochondrial fraction. Tim23, a mitochondrial protein, was used as a control.

FIGS. 3A-B. A. Submitochondrial distribution of CHCM1/CHCHD6. Western blot analyses of submitochondrial fractions. Submitochondrial fractions were prepared using RKO cells as described in Experimental Procedures. MT: total mitochondria fraction, OM: outer membrane fraction, IMS: intermembrane space fraction, IM: inner membrane fraction, M: matrix fraction. B. Sodium carbonate extraction-based distribution of CHCM1/CHCHD6. Western blot analyses of samples from sodium carbonate extraction assay in RKO and MCF7 cells. $S_{100}$: soluble fraction, $S_{240}$: membrane-associated fraction, $P_{240}$: integral membrane fraction. p97 serves as a marker of soluble and membrane-associated fractions, and Tim23 as a marker of integral membrane fraction.

FIGS. 4A-C. Genotoxic stress down-regulates CHCM1/CHCHD6. A. Northern blot analyses showing the effect of genotoxic etoposide on CHCM1/CHCHD6 mRNA expression in the indicated cells lines. C: control; E: etoposide, 30 µM for 24 hr. B. Effect of doxorubicin (ADRIAMYCIN®) on CHCM1/CHCHD6 mRNA levels in RKO cells. Cells were treated with ADRIAMYCIN® (0.5 µM) for the indicated times in hours. C: untreated controls. C. Western blot analyses showing DNA damage down-regulation of CHCM1/CHCHD6 protein levels in the indicated cells lines. C: control; E: etoposide, 30 µM for 24 hrs; A: ADRIAMYCIN®, 1.0 µM for 24 hr.

FIGS. 5A-B. CHCM1/CHCHD6 depletion reduces cell growth. A. Northern and Western blot analyses showing CHCM1/CHCHD6 knockdown in RKO and MCF7 cells lines. S: scramble; G4, G5, G6, G7 and G8 represent different CHCM1/CHCHD6-shRNA constructs. B. MTT assays showing cell growth in scramble or CHCM1/CHCHD6 knockdown cells representing RKO, MCF7 and MDA231 cell lines. G4 and G8 are two different CHCM1/CHCHD6-shRNA constructs. Values represent mean±SEM of triplicate samples.

Figure 6A:
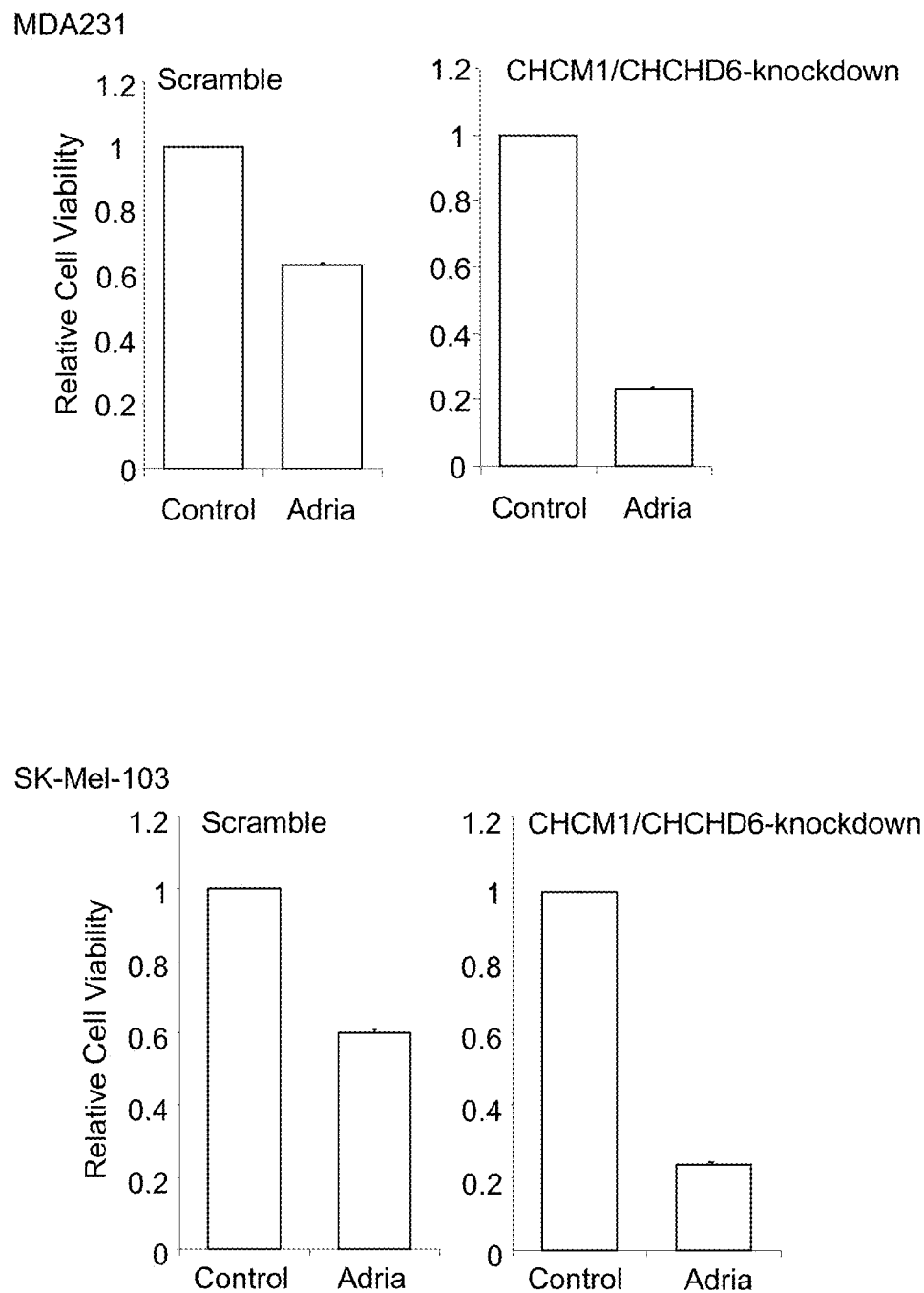
Figure 6B:
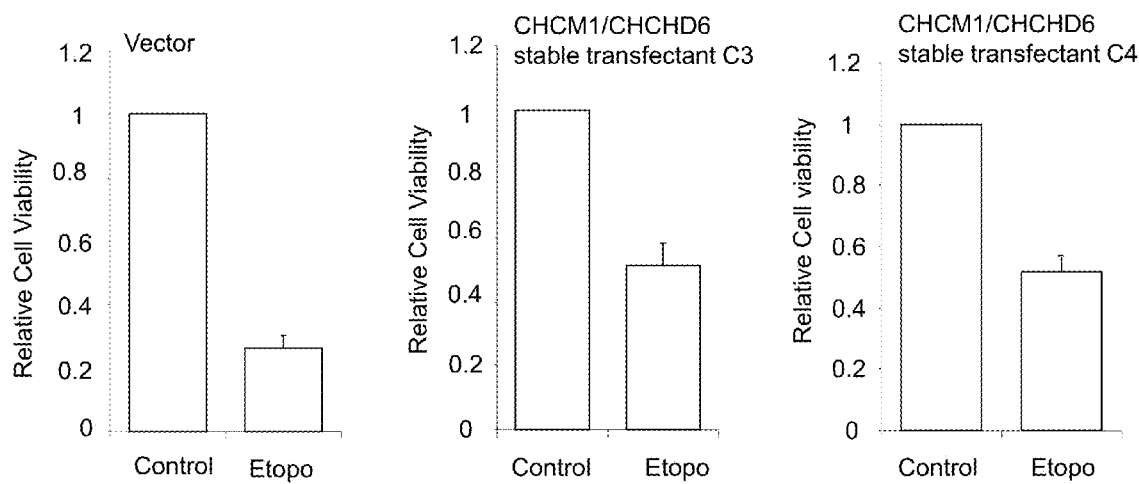

FIGS. 6A-B. CHCM1/CHCHD6 depletion and overexpression alters chemosensitivity of human cancer cells to genotoxic anticancer drugs. A. CHCM1/CHCHD6 knockdown increases cellular sensitivity to doxorubicin (ADRIAMYCIN®). MDA231 and SK-Mel-103 cells were untreated or treated with ADRIAMYCIN® (Adria, 3 µM for MDA231 and 1 µM for SK-Mel-103) for 24 hr and cell viability was assessed by MTT assay. Values represent mean±SEM of triplicate samples. B. Stable overexpression of CHCM1/CHCHD6 reduces cellular sensitivity to etoposide. RKO cells stably expressing exogenous CHCM1/CHCHD6 or vector transfected cells were untreated or treated with etoposide (30 µM) for 48 hr and cell viability was determined by MTT assay. C3 and C4 are two independent CHCM1/CHCHD6 stable transfectants. Values represent mean±SEM of triplicate samples.

FIGS. 7A-D. CHCM1/CHCHD6 interacts with Mitofilin, DISC1 and CHCHD3. A. Exogenous CHCM1/CHCHD6 interacts with endogenous Mitofilin. S-tag pull down analyses were performed on vector transfected or CHCM1/CHCHD6 transfected RKO cells. CHCM1/CHCHD6-B4 and CHCM1/CHCHD6-C3 are independent stable transfectants that express exogenous HA-S-tagged CHCM1/CHCHD6. S-tag pull down was done with S-tag agarose beads and Western blot analyses with indicated antibodies. B. Endogenous CHCM1/CHCHD6 interacts with endogenous Mitofilin. RKO and MCF7 cell lysates were used for CHCM1/CHCHD6 immunoprecipitation by anti-CHCM1/CHCHD6 antibody and Western blot analyses were done with the indicated antibodies. C. Exogenous CHCM1/CHCHD6 interacts with endogenous DISC1 and CHCHD3. S-tag pull down analyses were performed on crude mitochondria lysate from vector transfected or CHCM1/CHCHD6 transfected RKO cells. CHCM1/CHCHD6-B4 and CHCM1/CHCHD6-C3 are independent stable transfectants that express exogenous HA-S-tagged CHCM1/CHCHD6. S-tag pull down was done with S-tag agarose beads and Western blot analysis with indicated antibodies. D. Endogenous CHCM1/CHCHD6 interacts with endogenous DISC1 and CHCHD3. Crude mitochondria lysate from RKO cell was used for CHCM1/CHCHD6 immunoprecipitation by anti-CHCM1/CHCHD6 antibody and Western blot analyses were done with the indicated antibodies.

Figure 8A:
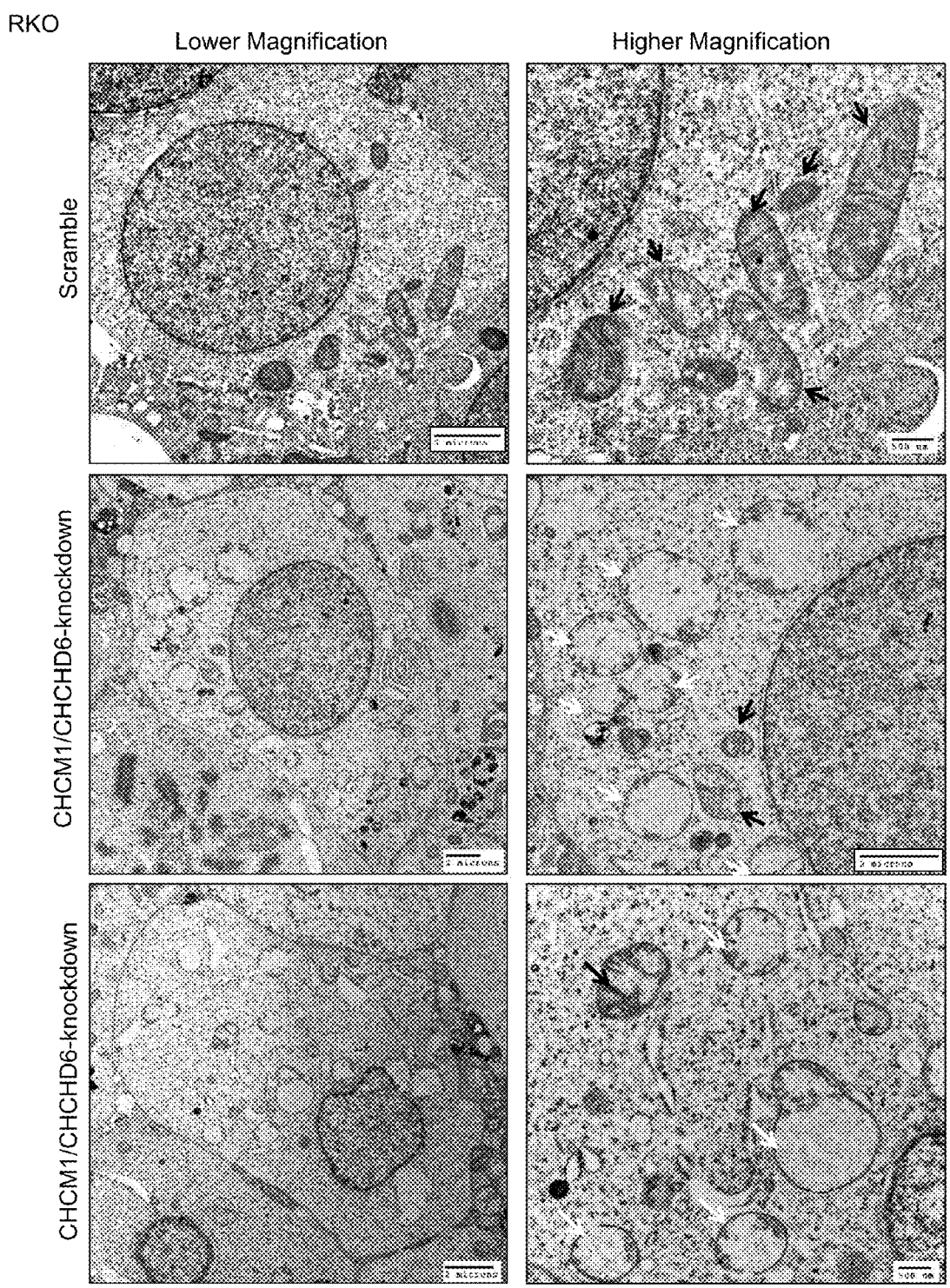
Figure 8B:
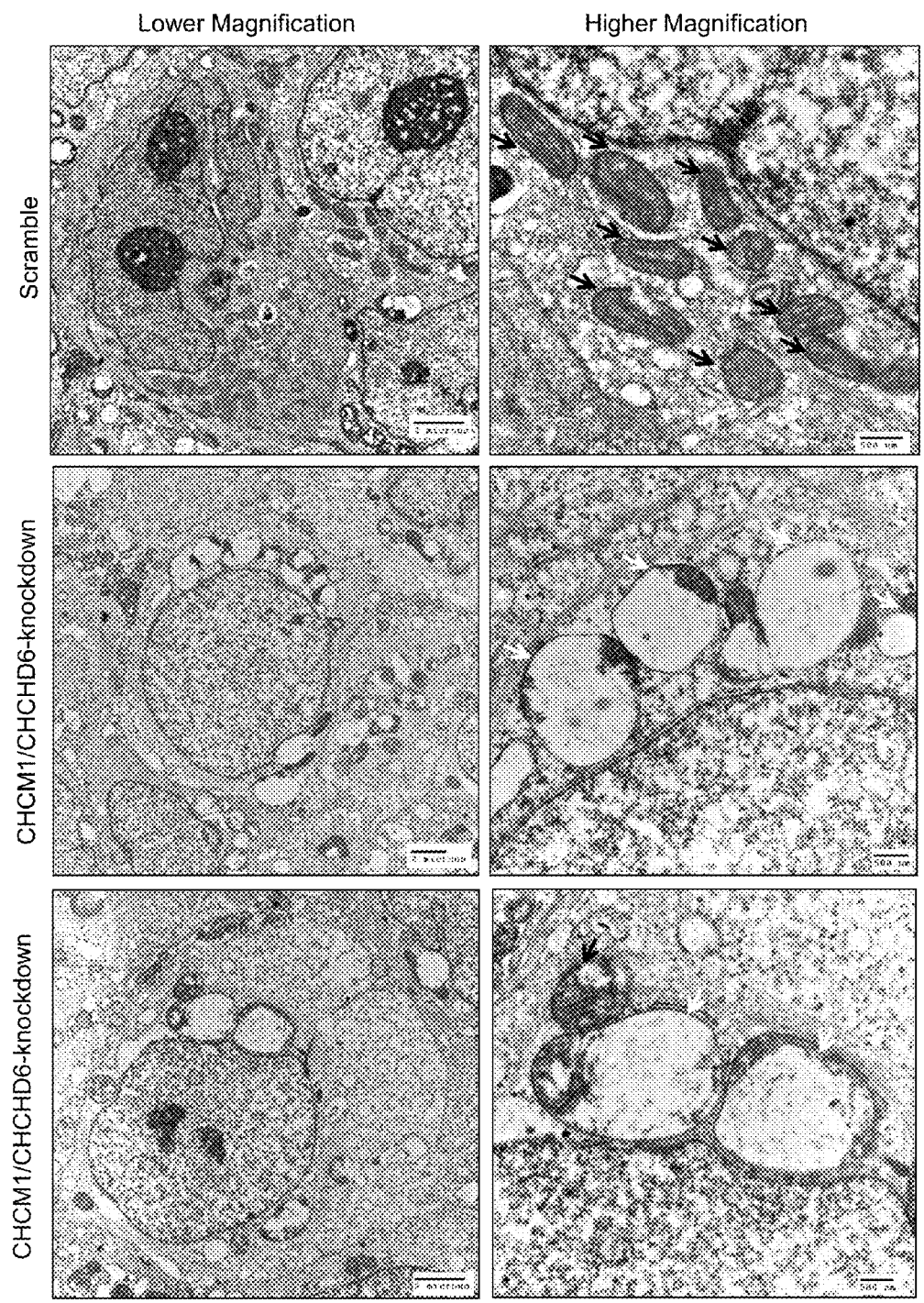

FIGS. 8A-B. CHCM1/CHCHD6 knockdown affects mitochondria cristae morphology. Electron microscope (EM) analyses of scramble and CHCM1/CHCHD6 knockdown RKO cells (A) and MCF7 cells (B). Left panel shows EM photographs at lower magnification and right panel shows the corresponding photographs at higher magnification. Black arrows indicate normal mitochondria. White arrows indicate mitochondria with abnormal cristae structures.

FIGS. 9A-D. CHCM1/CHCHD6 directly interacts with Mitofilin via its C-terminal end. A. Direct interaction between CHCM1/CHCHD6 and Mitofilin. Purified S-tagged full length CHCM1/CHCHD6 was incubated with gel-purified Mitofilin-GST or GST proteins and S-tag pull-down assays were performed. The pull-down protein products were analyzed by Western blot using anti-S or anti-GST antibodies. B. A schematic illustration of the full-length and deletion variants of CHCM1/CHCHD6 protein. C. Coomassie blue staining of recombinant full-length and deletion variants of CHCM1/CHCHD6 from bacteria lysate. S-tag pull-down of recombinant full-length and deletion variants of CHCM1/CHCHD6 were performed on bacteria lysates. The CHCM1/CHCHD6 protein products are indicated by (*). D. Mapping of CHCM1/CHCHD6 and Mitofilin interaction region on CHCM1/CHCHD6. Left panel: Purified S-tagged full length CHCM1/CHCHD6 and deletion variants were incubated with gel-purified Mitofilin-GST or GST protein. Then S-tag pull-downs were performed. The pull-down protein products were analyzed by Western blot using anti-S and anti-GST antibodies. Right panel: Western blot analysis of approximately 1% input of purified GST and Mitofilin-GST proteins.

FIGS. 10A-C. CHCM1/CHCHD6 and Mitofilin are coordinately regulated. A. Western blot analysis of Mitofilin levels in scramble (Scr) or CHCM1/CHCHD6 knockdown SK-Mel-103 and RKO cells. Scr: scramble. B. Western blot analysis of CHCM1/CHCHD6 levels in scramble (Scr) or Mitofilin knockdown SK-Mel-103 and RKO cells. Western blot analyses were performed using anti-CHCM1/CHCHD6 or anti-Mitofilin antibodies. C. Western blot analysis of Mitofilin levels in two independent stable transfectants (B4 and C3) that express exogenous HA-S-tagged CHCM1/CHCHD6. Respective blots were also probed with anti-β-actin antibody as loading controls. Results in panel C are the same as shown also for input in FIG. 7A.

FIGS. 11A-B. CHCM1/CHCHD6 deficiency induces mitochondrial dysfunction. A. CHCM1/CHCHD6 knockdown affects cellular ATP production. ATP levels in scrambled and CHCM1/CHCHD6 knocked down cells were determined as described in Experimental procedures. G4 and G8 represent two independent knockdown cells achieved via two different CHCM1/CHCHD6-shRNA constructs. Values represent average±SEM of four independent experiments *$p<0.05$. B. CHCM1/CHCHD6 knockdown affects oxygen consumption rate. Oxygen consumption rates in scrambled and CHCM1/CHCHD6 knocked down cells were determined as described in Experimental Procedures. G4 and G8 represent two independent knockdown cells achieved via two different CHCM1/CHCHD6-shRNA constructs. Values represent average±SEM of three independent experiments *$p<0.05$.

FIGS. 12A-B. Respiratory chain inhibitors do not affect CHCM1/CHCHD6 levels. A. Western blot analyses showing that antimycin A or rotenone does not have appreciable effect on CHCM1/CHCHD6 protein levels in RKO cells treated with the indicated concentration of each agent for 24 hr. B. Western blot analyses showing that treatment with antimycin A (1 µg/ml) or rotenone (0.1 µg/ml) for various time points does not alter CHCM1/CHCHD6 protein levels in RKO cells. C: control. Respective blots were also probed with anti-β-actin antibody as loading controls.

FIGS. 13A-B. CHCM1/CHCHD6 knockdown is not associated with down-regulation of CHCHD3 levels. A. Western blot analyses show that CHCM1/CHCHD6 knockdown in RKO cells does not lead to down-regulation of CHCHD3 levels. Scr: scramble, KD: CHCM/CHCHD6 knockdown. Exp1, Exp2, Exp3 stand for three independent experiments. Respective blots were also probed with anti-β-actin antibody as loading controls. B. Relative density of CHCHD3 protein after normalization with β-actin levels. Values represents mean+SEM of three independent experiments.

Figure 14:
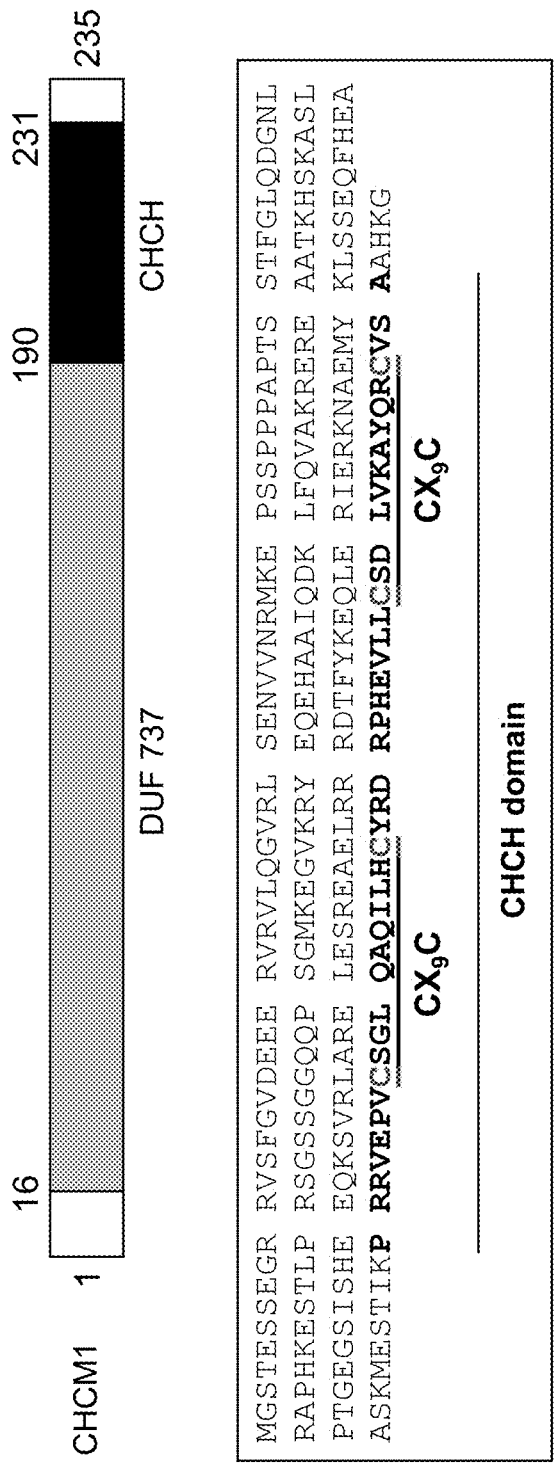

FIG. 14. Schematic (upper panel) and amino acid sequence (lower panel) of CHCM1. CHCH domain is underlined. DUF: domain of unknown function.

Figure 15:
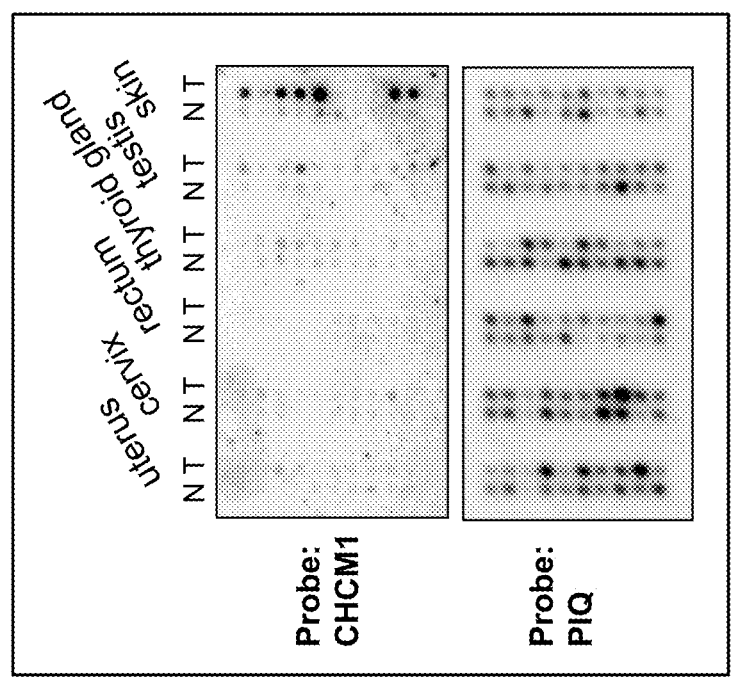

FIG. 15. CHCM1 mRNA expression is increased in melanoma samples when compared to normal skin. Cancer profiling array blot was probed with CHCM1 cDNA. Same blot was also probed with a human PIQ cDNA probe which shows different expression pattern. N: normal; T: tumor.

FIG. 16. Clinicopathological features of melanoma samples (shown in FIG. 15) exhibiting higher CHCM1 mRNA levels.

Figure 17:
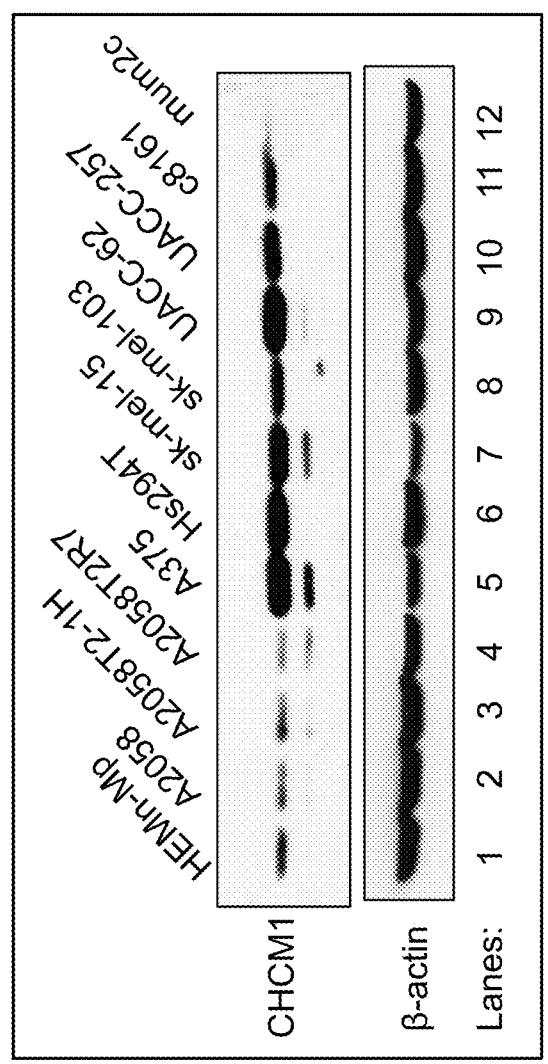

FIG. 17. Western blot analysis showing CHCM1 expression in normal melanocytes and in melanoma cell lines. Lane 1: normal melanocytes. Lanes 2-12 melanoma cells. Lanes 2-4 show derivatives of same A2058 cell line. Same blot was probed with beta-actin antibody.

Figure 18:
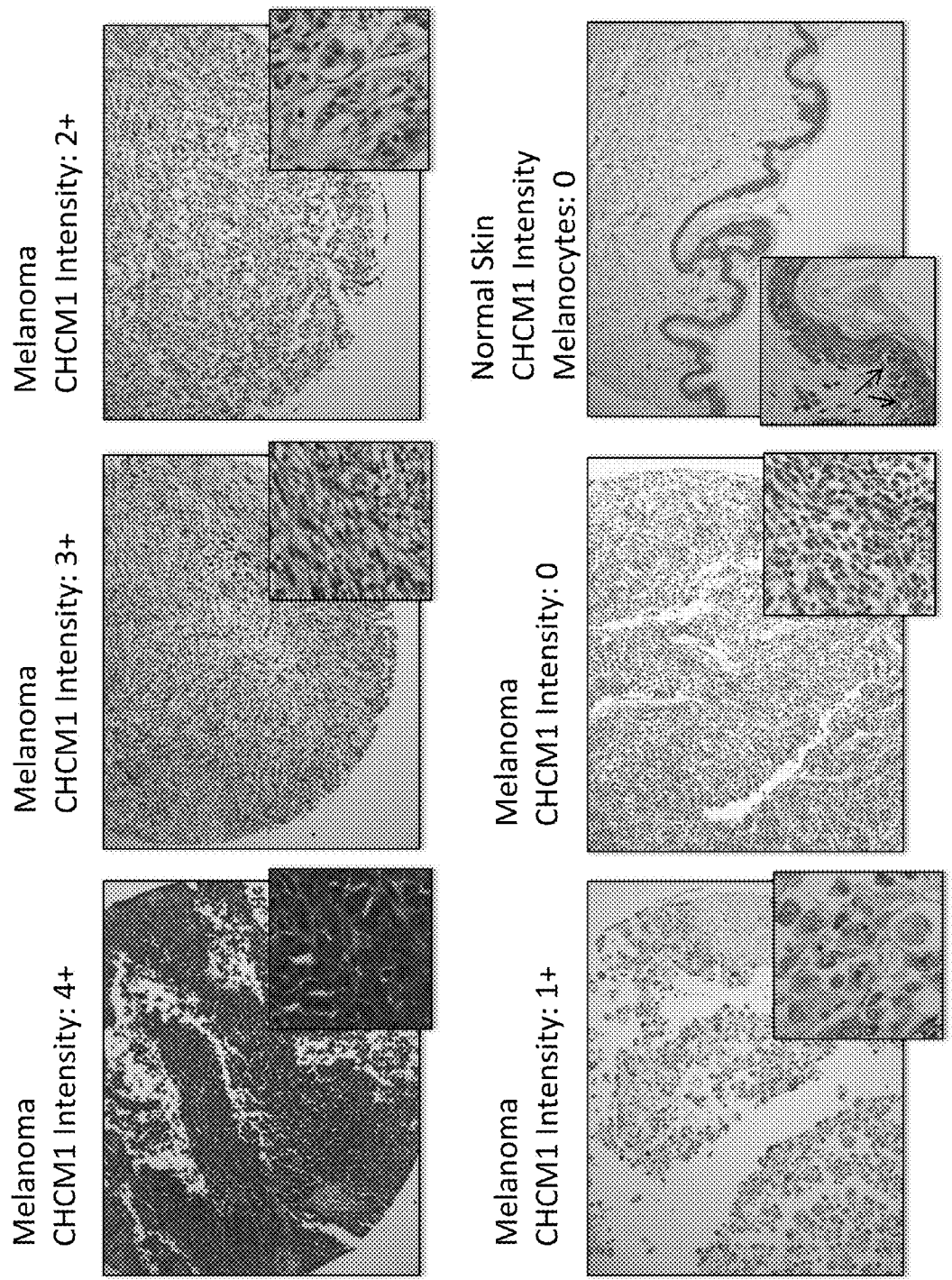

FIG. 18. Representative immunohistochemical staining showing expression of CHCM1 in melanoma and normal skin sections. Varying CHCM1-specific staining is shown in red to pink. In the case of normal skin, most of the superficial cells in the epidermal layer are weakly positive. The basal layer shows weak staining with melanocytes (arrows) mostly negative for CHCM1 staining.

FIGS. 19A-D. CHCM1 staining intensity in melanoma and normal skin specimens, keratinocytes (kera) and melanocytes (melano). Normal adjacent tissue (NAT).

FIG. 20. CHCM1 staining intensity in melanoma compared to melanocytes in normal skin.

FIG. 21. DTIC, an anticancer drug, down-regulates CHCM1 in A375 melanoma cells. Cells were treated with indicated concentration of DTIC for 96 hrs and Western blot analyses were performed with indicated antibodies.

FIG. 22. Cisplatin, an anticancer drug, downregulates CHCM1 in UACC-62 melanoma cells. Cells were treated with indicated concentration of cisplatin for 24 hrs and Western blot analyses were performed with indicated antibodies.

FIG. 23. Etoposide (E) and ADRIAMYCIN® (A), anticancer drugs, down-regulate CHCM1 in various human breast cancer cell lines.

Figure 24:
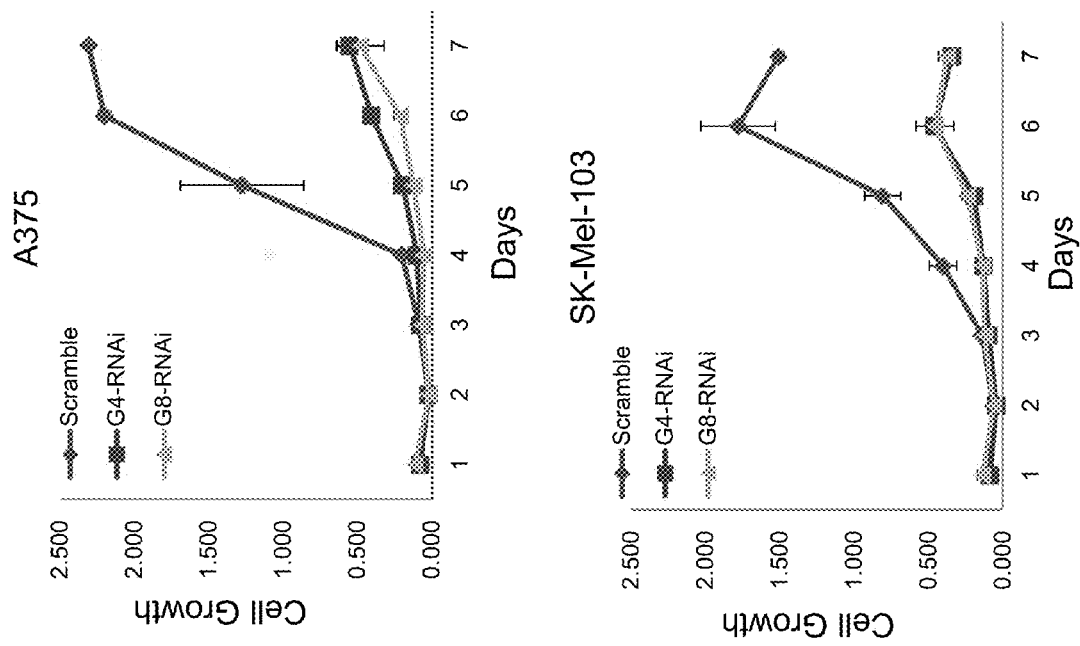

FIG. 24. CHCM1 knockdown leads to growth inhibition in melanoma cells. MTT assays showing cell growth in scramble or CHCM1 knockdown cells. G4 and G8 are two different CHCM1 shRNA constructs.

5. DETAILED DESCRIPTION OF THE INVENTION

For clarity of disclosure, and not by way of limitation, the detailed description of the invention is divided into the subsections set forth below.

5.1. Coiled coil Helix Cristae Morphology 1 (CHCM1)

CHCM1 (Coiled coil Helix Cristae Morphology 1) is a mitochondrial protein that is also annotated in the GenBank as CHCHD6. The nucleotide and amino acid sequences of CHCM1/CHCHD6 are deposited in the GenBank, under accession no. JF264889 (*Homo sapiens* coiled-coil-helix cristae morphology 1 (CHCM1) mRNA, complete cds).

SEQ ID NO: 1 sets forth the nucleic acid sequence of CHCM1 as deposited in GenBank under accession no. JF264889.

SEQ ID NO: 2 sets forth the 235 amino-acid sequence of CHCM1 as deposited in GenBank under accession no. JF264889.

CHCM1 contains 235 amino acids and 26.5 kDa in size (FIGS. 1A-B). The carboxyl-terminal end contains a Coiled coil Helix-Coiled coil Helix (CHCH) domain and the amino-terminal end harbors a putative N-myristoylation site (FIGS. 1A-B).

Based on the known human sequences, CHCM1 DNA and RNA and CHCM1 protein cognates in mammals and birds can be identified and characterized using methods known in the art.

Recombinant or naturally occurring CHCM1 nucleotide sequences of interest may be identified, e.g., in mammalian and bird species, as being at least 45% (or 55%, 65%, 75%, 85%, 95%, 98%, or 99%) identical to the nucleotide sequence of SEQ ID NO:1 or a complement thereof.

Recombinant or naturally occurring CHCM1 nucleotide sequences of interest may also be identified, e.g., in mammalian and bird species, as comprising a nucleotide sequence encoding a protein having an amino acid sequence that is at least 45% (or 55%, 65%, 75%, 85%, 95%, 98%, or 99%) identical to the amino acid sequence of SEQ ID NO:2, wherein the protein encoded by the nucleotide sequence also exhibits at least one structural and/or functional feature of a CHCM1 protein.

Recombinant or naturally occurring CHCM1 amino acid sequences of interest may be identified, e.g., in mammalian and bird species, as being at least 45% (or 55%, 65%, 75%, 85%, 95%, 98%, or 99%) identical to the amino acid sequence of SEQ ID NO:2 wherein the protein exhibits at least one structural and/or functional feature of a CHCM1 protein.

In another embodiment, CHCM1 amino acid sequences of interest share at least 30% homology with a wild-type CHCM1 protein. In other embodiments, CHCM1 protein shares 30-40%, 40-50%, 50-60%, 60-70%, 70-80%, 80-90% or 90-100% homology with a wild-type CHCM1 protein.

Recombinant or naturally occurring CHCM1 nucleic acid molecules may be at least 45% (or 55%, 65%, 75%, 85%, 95%, 98%, or 99%) identical to the nucleotide sequence of SEQ ID NO:1, or a complement thereof, wherein such nucleic acid molecules encode a protein that exhibits at least one structural and/or functional feature of the CHCM1 polypeptide.

CHCM1 Biomarker, Targeting or Regulating CHCM1 Expression, and Methods Based on Same The invention disclosed herein is based on the discovery by the inventors that there is a link between CHCM1 and tumors, particularly malignant melanoma. The inventors have discovered that CHCM1 is down-regulated in response to DNA damage-inducing anticancer drugs and is important for the integrity of mitochondrial cristae structures.

CHCM1 is linked to melanoma development and/or progression. CHCM1 may be used to characterize melanoma pathogenesis and may also serve as (i) a marker for improved diagnosis and prognosis and (ii) a target to develop novel therapeutics.

CHCM1 expression is down-regulated by DTIC and cisplatin in melanoma cell lines (FIGS. 5A-B and 6A-B). DTIC and cisplatin-mediated inhibition of CHCM1 appears to be one of the key events in sensitizing melanoma cells to these drugs in the clinical setting. Lack of CHCM1 inhibition may make melanoma cells resistant against these drugs in the clinic.

As disclosed hereinabove, vemurafenib does not work in melanomas that harbor wild type BRAF. Another limitation of vemurafenib is that some melanomas although harbor BRAF mutation do not respond to vemurafenib (inherent resistance) while others initially respond but later acquire resistance (9, 11, 12). The molecular basis for acquisition to vemurafenib resistance is believed to be multifactorial in nature and remains to be fully investigated (12). Deregulation of CHCM1 may be one of the contributing factors for the inherent or acquired resistance to vemurafenib. As disclosed in the Examples set forth herein, CHCM1 knockdown (genetic inhibition) affects growth of melanoma cell lines that harbor mutant BRAF (vemurafenib-sensitive A375 and UACC-62) or wild type BRAF (vemurafenib-nonresponsive Sk-Mel-103) (FIGS. 8A-B).

In one embodiment, CHCM1 targeting can be used to further improve the therapeutic potential of vemurafenib in vemurafenib-sensitive BRAF-mutant melanoma cells. Wild-type BRAF gene sequences and mutations of the BRAF gene are well known in the art (see, e.g., H. Davies et al. 2002. Mutations of the BRAF gene in human cancer. Nature 417: 949-954.

In another embodiment, CHCM1 targeting can be used to manage melanomas for which vemurafenib cannot be used (i.e., to manage BRAF wild-type tumors) or for those that harbor BRAF mutation but have inherent or acquired resistance to vemurafenib.

CHCM1 can be detected by analyzing specimens by immunohistochemical staining, Western blotting, Immunoprecipitation, protein pull-down, Northern or Dot blotting, microarray or any modification of these procedures. CHCM1 may be detected, for example, in the circulation in cancer patients and their blood samples may be used as materials for its detection for diagnosis/prognosis and response to therapy.

CHCM1 is an intracellular protein and it is well known in the art that some intracellular proteins can be detected in circulation (blood sample) as tumor biomarkers. For example, DJ-1/PARK7 is an intracellular protein that can be detected at an increased levels in circulation of breast cancer patients compared to group who did not have breast cancer (Clin Cancer Res November 2001 7; 3328 also mentioned at this url: http://www.mblintl.com/product/CY-9050). Similarly, SMAC is an intracellular protein but has been reported to be found in serum and the potential of circulating Smac was investigated in bladder cancer patients (Int J Oncol. 2012 April; 40(4):1246-50). Such art-known methods can be used to detect CHCM1 in patient samples, such as blood or tissue samples.

Melanoma is a complex disease and accurate diagnosis is of paramount importance. Newer markers that help facilitate accurate diagnosis and diagnosis of difficult cases are highly desirable. CHCM1 may be employed as a marker for use in melanoma diagnosis.

In one embodiment, CHCM1 expression may be determined, using methods known in the art, at different stages of the melanoma disease progression, to predict tumor behavior and response to cancer therapy.

Also, since better therapeutic options are needed for melanoma, in another embodiment CHCM1 may be employed as a molecular target to develop therapeutics. For example, therapeutics (including for example, small molecules) may be developed and existing ones also utilized to (i) block/decrease CHCM1 expression in human tumors and/or (ii) disrupt its interactions with other molecules and thereby inhibit or completely block tumor growth.

Diagnostic methods and tests for CHCM1 expression levels are also provided. Such diagnostic methods and tests may provide information that no test for melanoma currently known in the art provides. In art-known methods, a panel of markers such as S100, HMB-45, Melan-A, Mart-1 and tyrosinase are used for melanoma diagnosis in the clinic. However, it is not uncommon for melanomas to be negative for some of the available markers. To avoid misdiagnosis, testing for the presence of CHCM1 marker may thus be used to further ascertain a diagnosis.

As disclosed herein, CHCM1 is overexpressed in cutaneous (skin) and non-cutaneous malignant melanomas (FIGS. 19A-D) and can be used as a marker for melanoma diagnosis. In particular, all mucosal melanoma samples in Example 2 results (FIGS. 19A-D) are positive for CHCM1 expression and the majority of them show higher CHCM1 expression with staining intensity in the 2+ and 3+ ranges (where 2+ and 3+ are an arbitrary scale chosen by the skilled artisan for comparing with the staining intensity in normal melanocytes).

Mucosal melanomas are believed to exhibit more aggressive behavior and have higher mortality compared to cutaneous melanomas (Seetharamu N. et al., The Oncologist July 2010 vol. 15 no. 7 772-781). Diagnosis of mucosal melanoma is difficult and generally delayed (Seetharamu N. et al., The Oncologist July 2010 vol. 15 no. 7 772-781). Mucosal melanomas also frequently show micrometastases. The findings that higher number of mucosal melanomas show increased positivity for CHCM1 demonstrate that CHCM1 can also be used for diagnosis of such melanomas including the associated micrometastases.

Use of a CHCM1 assay will help avoid misdiagnosis and facilitate accurate diagnosis of difficult to diagnose cases, and will lead to more timely initiation of intervention/treatment.

Assays for CHCM1 can be of various types appropriate for detecting the expression level of a gene or its protein product. Formats for these gene and protein assays are well known in the art (see, e.g., J. D. Pollock 2002, Gene expression profiling: methodological challenges, results, and prospects for addiction research. Chemistry and Physics of Lipids 121: 241-256; S. Z. Cekan, 2004, Reproductive Biology and Endocrinology 2004, 2:68 (doi:10.1186/1477-7827-2-68); www.plexpress.com/tiedostot/Plexpress_Whitepaper.pdf (visited on Dec. 13, 2013); each of which is incorporated by reference herein in its entirety).

One type of assay provided herein is to analyze biopsy specimens by immunohistochemical staining using an anti-CHCM1 antibody (such as a monoclonal or polyclonal antibody) or any other substance that binds to a CHCM1 protein or nucleic acid and can be detected optically, electrically, magnetically, chemically, physically, or by some other means well known in the art. Western blotting, Northern blotting, dot blotting or PCR-based approaches, all well known in the art, may also be used. It will be readily apparent to the skilled artisan that other methods well known in the art may be used to detect CHCM1.

Kits for performing a CHCM1 assay are also provided. In one embodiment, the kit comprises an anti-CHCM1 antibody (such as a monoclonal or polyclonal antibody). In another embodiment, the kit comprises a substance that binds to a CHCM1 protein or nucleic acid and can be detected optically, electrically, magnetically, chemically, physically, or by some other means well known in the art. In another embodiment, the kit comprises reagents for carrying out an immunohistochemical staining assay, a Western blot, a Northern blot, a dot blot or a PCR-based assay, all of which are well known in the art. In another embodiment, the kit comprises instructions for carrying out a CHCM1 assay using component(s) provided in the kit.

In the current state of the art, vemurafenib has been approved by the US Food and Drug Administration (FDA) as the most recent option for the treatment of malignant melanoma that harbors a BRAF mutation. Vemurafenib, however, does not work in melanomas that harbor wild type BRAF. Another limitation of vemurafenib is that some melanomas that harbor a BRAF mutation do not respond to vemurafenib (inherent resistance) while others initially respond but later acquire resistance.

Deregulation of CHCM1 may contribute to a malignant melanomas' inherent or acquired resistance to vemurafenib. As shown in Example 2, CHCM1 knockdown by RNA interference approach (genetic inhibition) affects growth of melanoma cell lines that harbor mutant BRAF (vemurafenib-sensitive A375 and UACC-62) or wild type BRAF (vemurafenib-nonresponsive Sk-Mel-103) (FIGS. 8A-B). Therefore, targeting of CHCM1 may be used to (i) further improve the therapeutic potential of vemurafenib in vemurafenib-sensitive BRAF-mutant melanoma cells, and (ii) manage melanomas for which vemurafenib cannot be used (i.e. BRAF wild type tumors) or for those that harbor BRAF mutation but have inherent or acquired resistance to vemurafenib. Clearly, targeting CHCM1 would lead to better therapeutic management of malignant melanoma.

As shown FIGS. 6A-B of Example 1, the efficacy of cancer therapeutics, including genotoxic anticancer drugs, can be enhanced by decreasing CHCM1 levels while administering the cancer therapeutic, such as by co-administering a compound that reduces the levels of CHCM1 or blocking the functioning of CHCM1 proteins that have been expressed.

In one embodiment, a method is provided for treating a cancer or a tumor comprising the steps of (a) administering a therapeutic compound that is used for treatment and/or management of the cancer or tumor and (b) administering a compound that reduces the expression of CHCM1 or blocks or inhibits the functioning of CHCM1 proteins. The cancer or tumor may be breast cancer, melanoma or another form of cancer.

The therapeutic compound may be an anticancer drug including, but not limited to, doxorubicin (ADRIAMYCIN®), etoposide, bendamustine, busulfan, carmustine, chlorambucil, cyclophosphamid, dacarbazine (dtic), ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D/dactinomycin, bleomycin, daunorubicin, epirubicin, idarubicin, mitomycin, mitoxantrone, docetaxel, irinotecan, paclitaxel, topotecan, vinblastine, vincristine, vinorelbine, carboplatin, cisplatin and oxaliplatin, or may be any anti-cancer or anti-tumor drug known in the art. The compound reducing the expression of CHCM1 or blocking its activity or its interactions with other proteins can be a shRNA, siRNA, peptide, small molecule (including Cisplatin and DTIC), an antibody, or a large molecule such as a full-length protein or a larger fragment of a protein. The method of treating a cancer can comprise a first step of determining the level of CHCM1 expression in the cancer cells and if CHCM1 is being overexpressed, then proceeding with steps (a) and (b).

Differences between small molecules and large molecules (also referred to in the art as biologics) are well known in the art. Small molecules are usually synthetic, organic compounds with well-defined structures and are relatively stable. Small molecules typically have MW<700 Da and a low number of atoms.

Other art-known definitions of small molecules include:

A medicinal drug compound having a molecular weight of less than 1000 daltons, and typically between 300 and 700 daltons (http://en.wiktionary.org/wiki/small_molecule_drug, visited on Dec. 13, 2013).

Molecule having a low molecular weight (<900 Daltons]) organic compound that may help regulate a biological process, with a size on the order of $10^{-9}$ m (http://en.wikipedia.org/wiki/Small_molecule, visited on Dec. 13, 2013).

Small molecules are typically administered orally. Small molecules have potential for off-target activity. Small molecules are metabolized.

Large molecules are usually protein- or carbohydrate-based.

Large molecules have complex physico-chemical characteristics and are heat sensitive. Large molecules have MW>700 Da (e.g., Peptides ~1 kDa; Recombinant proteins ~30 kDa; Antibodies ~150 kDa). Large molecules are typically administered parenterally. Large molecules have high selectivity and specificity. Large molecules are catabolized.

In another embodiment, a method is provided for treating a cancer or a tumor comprising down-regulating or blocking the activity of CHCM1 or blocking CHCM1 interactions with other proteins. Reducing the expression or blocking the activity of CHCM1 or blocking CHCM1 interactions with other proteins can comprise administering a compound that down-regulates CHCM1 or interferes with the functioning of CHCM1 or with CHCM1 interactions with other proteins. The compound can be any of the compounds described herein as modulating the expression of CHCM1, and any of the known types of compounds that will interfere with the expression or activity of a protein that has been modified to reduce the expression of CHCM1 or bind to it to reduce its activity or functionality. Additional compounds can be identified, based on the structure of CHCM1, using routine methods (see, e.g., Sotriffer C, Klebe G. Identification and mapping of small-molecule binding sites in proteins: computational tools for structure-based drug design. Farmaco March; 57(3):243-51, 2002; Geromichalos GD. Importance of molecular computer modeling in anticancer drug development. J BUON. 2007 September; 12 Suppl 1:S101-18).

In another embodiment, an assay is provided for a cancer or a tumor which comprises determining the level of CHCM1. Determining the level of CHCM1 can include the steps of obtaining a sample of the cancer or tumor (such as by performing a biopsy on a cancer or tumor) and performing an immunohistochemical staining procedure on the sample, wherein the immunohistochemical staining procedure detects CHCM1 expression. A last step can comprise evaluating the stained sample, using methods known in the art, to determine the level of CHCM1. Determining the level of CHCM1 can also comprise the steps of obtaining a blood sample from a patient having the cancer or tumor and detecting the level of CHCM1 in the blood sample.

In certain embodiments, the patient is a mammal, such as a human or a domestic mammal such as a cat, dog, rabbit, sheep, goat, pig, cow or horse. In other embodiments, the patient can be a non-domestic mammal such as a rodent or a zoo mammal, or can be a bird.

Determining the level of CHCM1 can comprise the steps of obtaining a tissue (e.g., blood) sample from the patient having the cancer and detecting the level of the mRNA for CHCM1 in the tissue sample, such as by using RT-PCR or a microarray, which are techniques well known in the art. The assay may be an assay to determine whether a cancer or a tumor is melanoma.

In another embodiment, an assay is provided for determining or testing whether a therapeutic compound modulates the expression of CHCM1 (and thus could potentially be used for treatment and/or management of a cancer or a tumor) comprising similar steps as described above, i.e., (a) administering a test therapeutic compound and (b) administering a compound that reduces the expression of CHCM1 or blocks or inhibits the functioning of CHCM1 proteins. The cancer may be breast cancer, melanoma or another form of cancer, as listed herein.

The therapeutic compound may be an anticancer drug including, but not limited to, doxorubicin (ADRIAMYCIN®), etoposide, bendamustine, busulfan, carmustine, chlorambucil, cyclophosphamid, dacarbazine (dtic), ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D/dactinomycin, bleomycin, daunorubicin, epirubicin, idarubicin, mitomycin, mitoxantrone, docetaxel, irinotecan, paclitaxel, topotecan, vinblastine, vincristine, vinorelbine, carboplatin, cisplatin and oxaliplatin.

The compound reducing the expression of CHCM1 or blocking its activity or its interactions with other proteins can be an shRNA, siRNA, peptide, small molecule (including Cisplatin and DTIC), an antibody, or a large molecule such as a full-length protein or a larger fragment of a protein or CHCM1 mimetics (small or large polypeptides) that would serve to disrupt CHCM1 interactions with other proteins.

The method of treating a cancer or tumor can comprise a first step of determining the level of CHCM1 expression in the cancer (or tumor) cells and if CHCM1 is being overexpressed, then proceeding with steps (a) and (b).

In another embodiment, an assay is provided for determining whether a therapeutic compound reduces the expression or activity of CHCM1 or its interactions with other proteins.

Methods are also provided for using inhibitors of CHCM1 to treat cancer, in particular to treat melanoma. A CHCM1 inhibitor is any agent that reduces levels of CHCM1 and/or interferes with CHCM1 activity and/or function and/or blocks and/or interferes with CHCM1 interactions with other proteins.

Methods are also provided for improving the efficacy of other cancer therapeutics, comprising the step of co-administering a CHCM1 inhibitor with another cancer therapeutic.

An assay for cancer is provided that determines the level of CHCM1 expression. In one embodiment, the cancer is melanoma.

According to various embodiments, a substance suitable for the methods disclosed herein can be a nucleic acid, such as a genetic construct or other genetic means directing expression of an antagonist of CHCM1 function. Nucleic acid molecules suitable for use in the methods disclosed herein include, but are not limited to, anti-sense polynucleotides, other polynucleotides that bind to CHCM1 mRNA, recombinant retroviral vector, or a combination thereof. In a preferred embodiment, the genetic construct comprises a gene delivery vehicle, a recombinant retroviral vector, or a combination thereof. In another preferred embodiment, the substance that inhibits CHCM1 function is a nucleic acid that hybridizes to a CHCM1 mRNA.

In other embodiments, substances suitable for the methods disclosed herein may also include, but are not limited to, peptidomimetic inhibitors of CHCM1 function, ribozymes, and an RNA aptamer, or a combination thereof.

Pharmaceutical agents or genetic therapies that reduce or eliminate CHCM1 activity and function encompass, but are not limited to the following: 1) small molecule inhibitors (preferably having a molecular weight of less than 10,000) of CHCM1 activity (i.e. suicide substrates; competitive or non-competitive inhibitors of CHCM1 activity; RNA aptamers), 2) anti-sense oligonucleotides, 3) peptidomimetics, 4) ribozymes, 5) means for interfering with transcription and/or translation of CHCM1 RNA, or 6) genetic therapy comprising transfection with a dominant negative CHCM1 mutant or 7) use of any of these approaches to block/interfere with CHCM1 interactions with other proteins.

Means for inhibiting CHCM1 function comprise genetic and non-genetic means for inhibiting CHCM1 function, and includes substances that inhibit CHCM1 functions, levels or interactions with other proteins.

Among the genetic construct inhibiting CHCM1 function are various "gene delivery vehicles" known to those of skill in the art, that facilitate delivery to a cell of, for example, a coding sequence for expression of a polypeptide, such as a CHCM1 inhibitor, an anti-sense oligonucleotide, an RNA aptamer capable of inhibiting CHCM1 activity, an RNA aptamer capable of inhibiting a ribozyme, or another genetic construct of inhibiting CHCM1 activity known to those of skill in the art.

Among the non-genetic means for inhibiting CHCM1 function are a pharmaceutical agent, and pharmaceutically acceptable salts thereof that are preferably administered in a pharmaceutically acceptable carrier.

According to preferred embodiments, substances suitable for the methods disclosed herein can be a nucleic acid, such as a genetic construct or other genetic means for directing expression of an antagonist of CHCM1 function. Such expression constructs are well known in the art and can be constructed to direct expression an antagonist of CHCM1 function using methods known in the art. Nucleic acid molecules suitable for use in the methods disclosed herein include, but are not limited to, anti-sense polynucleotides, other polynucleotides that bind to CHCM1 mRNA, recombinant retroviral vector, or a combination thereof. In a preferred embodiment, a genetic construct comprises a gene delivery vehicle, a recombinant retroviral vector, or a combination thereof. In a preferred embodiment, the substance that inhibits CHCM1 function is a nucleic acid that hybridizes to a CHCM1 mRNA.

Preferred substances may also include peptidomimetic inhibitors of CHCM1 function, ribozymes, and an RNA aptamer, or a combination thereof.

Suitable substances for use in the methods disclosed herein may also include a low molecular weight substance having a molecular weight of less than about 10,000 that inhibits CHCM1 activity. Characterizing whether CHCM1 is inhibited can be carried out using routine methods.

Cancers or Tumors that can be Diagnosed, Treated, or Managed

Other types of cancers or tumors, in addition to melanoma, can be diagnosed, treated, or managed using the methods disclosed herein and are listed below. Cancer or tumor treatments for the following types of cancer or tumor are well known in the art:

Acute Lymphoblastic Leukemia (ALL)
Acute Myeloid Leukemia (AML)
Adrenocortical Carcinoma
AIDS-Related Cancers, Kaposi Sarcoma, Lymphoma
Anal Cancer
Appendix Cancer
Astrocytomas
Atypical Teratoid/Rhabdoid Tumor, Central Nervous System
Basal Cell Carcinoma
Bile Duct Cancer, Extrahepatic
Bladder Cancer
Bone Cancer, Ewing Sarcoma Family of Tumors, Osteosarcoma and Malignant Fibrous Histiocytoma
Brain Stem Glioma
Brain Tumor, Astrocytomas, Brain and Spinal Cord Tumors, Brain Stem Glioma, Central Nervous System Atypical Teratoid/Rhabdoid Tumor, Central Nervous System Embryonal Tumors, Central Nervous System Germ Cell Tumors, Craniopharyngioma, Ependymoma
Breast Cancer
Bronchial Tumors
Burkitt Lymphoma
Carcinoid Tumor, Gastrointestinal
Carcinoma of Unknown Primary
Cardiac (Heart) Tumors
Central Nervous System, Atypical Teratoid/Rhabdoid Tumor, Embryonal Tumors,
Germ Cell Tumor, Primary Lymphoma
Cervical Cancer
Chordoma
Chronic Lymphocytic Leukemia (CLL)
Chronic Myelogenous Leukemia (CML)
Chronic Myeloproliferative Disorders
Colon Cancer
Colorectal Cancer
Craniopharyngioma
Cutaneous T-Cell Lymphoma
Duct, Bile, Extrahepatic
Ductal Carcinoma In Situ (DCIS)
Embryonal Tumors, Central Nervous System
Endometrial Cancer
Ependymoma
Esophageal Cancer
Esthesioneuroblastoma
Ewing Sarcoma
Extracranial Germ Cell Tumor
Extragonadal Germ Cell Tumor
Extrahepatic Bile Duct Cancer
Eye Cancer, Intraocular Melanoma, Retinoblastoma
Fibrous Histiocytoma of Bone, Malignant, and Osteosarcoma
Gallbladder Cancer
Gastric (Stomach) Cancer
Gastrointestinal Carcinoid Tumor
Gastrointestinal Stromal Tumors (GIST)
Germ Cell Tumor, Central Nervous System—Childhood, Extracranial—Childhood,
Extragonadal, Ovarian, Testicular
Gestational Trophoblastic Disease
Glioma, Childhood Brain Stem
Hairy Cell Leukemia
Head and Neck Cancer
Heart Cancer
Hepatocellular (Liver) Cancer
Histiocytosis, Langerhans Cell
Hodgkin Lymphoma
Hypopharyngeal Cancer
Intraocular Melanoma
Islet Cell Tumors, Pancreatic Neuroendocrine Tumors
Kaposi Sarcoma
Kidney, Renal Cell, Wilms Tumor and Other Childhood Kidney Tumors
Langerhans Cell Histiocytosis
Laryngeal Cancer
Leukemia, Acute Lymphoblastic (ALL), Acute Myeloid (AML), Chronic Lymphocytic (CLL), Chronic Myelogenous (CML), Hairy Cell
Lip and Oral Cavity Cancer
Liver Cancer (Primary)
Lobular Carcinoma In Situ (LCIS)
Lung Cancer, Non-Small Cell, Small Cell
Lymphoma, AIDS-Related, Burkitt, Cutaneous T-Cell, Hodgkin, Non-Hodgkin, Primary
Central Nervous System (CNS)
Macroglobulinemia, Waldenström
Male Breast Cancer
Malignant Fibrous Histiocytoma of Bone and Osteosarcoma
Melanoma, Intraocular (Eye)
Merkel Cell Carcinoma
Mesothelioma, Malignant
Metastatic Squamous Neck Cancer with Occult Primary
Midline Tract Carcinoma Involving NUT Gene
Mouth Cancer
Multiple Endocrine Neoplasia Syndromes
Multiple Myeloma/Plasma Cell Neoplasm
Mycosis Fungoides
Myelodysplastic Syndromes
Myelodysplastic/Myeloproliferative Neoplasms
Myelogenous Leukemia, Chronic (CML)
Myeloid Leukemia, Acute (AML)
Myeloma, Multiple
Myeloproliferative Disorders, Chronic
Nasal Cavity and Paranasal Sinus Cancer
Nasopharyngeal Cancer
Neuroblastoma
Non-Hodgkin Lymphoma
Non-Small Cell Lung Cancer
Oral Cancer
Oral Cavity Cancer, Lip and Oropharyngeal Cancer
Osteosarcoma and Malignant Fibrous Histiocytoma of Bone
Ovarian Cancer, Epithelial, Germ Cell Tumor, Low Malignant Potential Tumor
Pancreatic Cancer
Pancreatic Neuroendocrine Tumors (Islet Cell Tumors)
Papillomatosis
Paraganglioma
Paranasal Sinus and Nasal Cavity Cancer
Parathyroid Cancer
Penile Cancer
Pharyngeal Cancer
Pheochromocytoma, Pituitary Tumor
Plasma Cell Neoplasm/Multiple Myeloma Pleuropulmonary Blastoma
Pregnancy and Breast Cancer
Primary Central Nervous System (CNS) Lymphoma
Prostate Cancer
Rectal Cancer
Renal Cell (Kidney) Cancer
Renal Pelvis and Ureter, Transitional Cell Cancer
Retinoblastoma
Rhabdomyosarcoma
Salivary Gland Cancer
Sarcoma, Ewing, Kaposi, Osteosarcoma (Bone Cancer), Rhabdomyosarcoma, Soft Tissue,
Uterine
Sézary Syndrome
Skin Cancer, Melanoma, Merkel Cell Carcinoma, Nonmelanoma
Small Cell Lung Cancer
Small Intestine Cancer
Soft Tissue Sarcoma
Squamous Cell Carcinoma
Squamous Neck Cancer with Occult Primary, Metastatic
Stomach (Gastric) Cancer
T-Cell Lymphoma, Cutaneous
Testicular Cancer
Throat Cancer
Thymoma and Thymic Carcinoma
Thyroid Cancer
Transitional Cell Cancer of the Renal Pelvis and Ureter
Unknown Primary, Carcinoma of
Ureter and Renal Pelvis, Transitional Cell Cancer
Urethral Cancer
Uterine Cancer, Endometrial
Uterine Sarcoma
Vaginal Cancer
Vulvar Cancer
Waldenström Macroglobulinemia
Wilms Tumor Routes of Administration and Definitions Administering a therapeutic compound refers to the process of delivering to a mammal a therapeutic agent, or a combination of therapeutic agents. The process of administration can be varied, depending on the therapeutic agent, or agents, and the desired effect. Administration can be accomplished by any means appropriate for the therapeutic agent, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Administration will generally also include delivery with a pharmaceutically acceptable carrier, such as, for example, a buffer, a polypeptide, a peptide, a polysaccharide conjugate, a liposome and/or a lipid. Gene therapy protocol is considered an administration in which the therapeutic agent is a polynucleotide capable of accomplishing a therapeutic goal when expressed as a transcript or a polypeptide in the mammal.

The administration of a compound and variants thereof (e.g., "administering" a compound) used in reference to a compound of the invention can also mean introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In treating a cancer or a tumor, a therapeutically effective amount a CHCM1 inhibitor is administered. A therapeutically effective amount is that amount that will generate the desired therapeutic outcome. A therapeutically effective amount can be an amount administered in a dosage protocol that includes days or weeks of administration. It is also that amount of active compound or pharmaceutical agent that elicits the biological or medicinal response in a tissue, system, animal or human that is being sought by a researcher, veterinarian, medical doctor or other clinician.

The term "pharmaceutically acceptable carrier" refers to a carrier for administration of a therapeutic agent, such as, for example, a polypeptide, polynucleotide, small molecule (preferably a molecule having a molecular weight of less than about 10,000), peptoid, or peptide, refers to any pharmaceutically acceptable carrier that does not itself induce the production of antibodies harmful to the individual receiving the composition, and which may be administered without undue toxicity. It can also refer to a carrier, such as a solvent, suspending agent or vehicle, for delivering the compound or compounds in question to the animal or human. The carrier may be liquid or solid and is selected with the planned manner of administration in mind Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

A pharmaceutically acceptable component is one that is suitable for use with humans and/or animals without undue adverse side effects (such as toxicity, irritation, and allergic response) commensurate with a reasonable benefit/risk ratio.

"Mammalian cell" as used herein refers to a subset of eukaryotic cells useful in the invention as host cells, and includes human cells, and animal cells such as those from dogs, cats, cattle, horses, rabbits, mice, goats, sheep, pigs, etc. The cells used can be genetically unaltered or can be genetically altered, for example, by transformation with appropriate expression vectors, marker genes, and the like.

The term "antagonist" as used herein refers to a molecule that blocks signaling, such as for example a molecule that can bind a receptor, but which does not cause a signal to be transduced by the receptor to the cell. In general, an antagonist of a polypeptide is an inhibitor of any biological activity of the polypeptide. A given inhibitor or agonist may target and inhibit one biological activity, while not affecting another non-target activity of the molecule. As used herein, in other embodiments, suitable CHCM1 inhibitors for use in the methods disclosed herein can include, but are not limited to, short hairpin RNA (shRNA) small interfering RNAs (siRNAs) or microRNAs (miRNAs) that are effective to inhibit CHCM1 via RNA interference (RNAi) (post transcriptional gene silencing).

RNAi technology is well known in the art and provides an efficient means for blocking expression of a specific gene. RNAi technology takes advantage of the cell's natural machinery, facilitated by short interfering RNA molecules, to effectively knockdown expression of a gene of interest. There are several ways known in the art to induce RNAi, synthetic molecules, shRNA, siRNA, miRNA, RNAi vectors, and in vitro dicing.

RNAi may be used to inhibit the CHCM1 genes, such as by creating shRNA or siRNAs or miRNAs having the appropriate sequence and delivering them to the cells in which inhibition of the CHCM1 gene is desired. A key area of research in the use of RNAi for clinical applications is the development of a safe delivery method, which to date has involved mainly viral vector systems similar to those suggested for gene therapy. Once developed, these delivery methods can be employed in the methods disclosed herein. RNAi inducing agents can also be delivered using bacteria, retroviruses, DNA viruses, lipidoids and amphoteric liposomes and nanoparticle-based approaches known in the art.

General rules known in the art for selecting siRNA targets on mRNA sequences include, for example, the following (see www.rnaiweb.com/RNAi/siRNA_Design visited on Dec. 11, 2013): (i) Targets should be located 50-100 nt downstream of the start codon (ATG); (ii) Search for sequence motif $AA(N_{19})TT$ or $NA(N_{21})$, or $NAR(N_{17})YNN$, where N is any nucleotide, R is purine (A, G) and Y is pyrimidine (C, U); (iii) Target sequences should have a G+C content between 35-60%; (iv) Avoid stretches of 4 or more nucleotide repeats; (v) Avoid 5'URT and 3'UTR, although siRNAs targeting UTRs have been shown to successfully induce gene silencing; and (vi) Avoid sequences that share a certain degree of homology with other related or unrelated genes.

Similarities and differences between siRNA and shRNA are known in the art, see, e.g., Rao D D, Vorhies J S, Senzer N, Nemunaitis J. siRNA vs. shRNA: similarities and differences. Adv Drug Deliv Rev. 2009 Jul. 25; 61(9):746-59.

Designing shRNA targets is also well known in the art, see, e.g., Chris B. Moore, Elizabeth H. Guthrie, Max Tze-Han Huang, and Debra J. Taxman. Short Hairpin RNA (shRNA): Design, Delivery, and Assessment of Gene Knockdown. Methods Mol Biol. 2010; 629:141-158.)

Selecting targets for miRNA: In animals, the tendency of miRNAs to bind their mRNA targets with imperfect sequence homology poses considerable challenges with target prediction. In animals, target sites are often only partially complementary to their miRNAs and are mostly located in the 3'UTR of target genes. Several computational approaches have been developed to facilitate experimental design and predicting miRNA targets. In general, computational target prediction identifies potential binding sites according to base-pairing rules and cross species conservation conditions.

The dosage form of the CHCM1 inhibitor that is administered according to the methods disclosed herein may be a liquid solution ready for use or intended for dilution with a preservation solution. Alternatively, the dosage form may be lyophilized or power filled prior to reconstitution with a preservation solution. The lyophilized substance may contain, if suitable, conventional excipients.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "composition" is intended to encompass a product comprising the specified ingredients in the specified amounts, as well as any product which results, directly or indirectly, from combination of the specified ingredients in the specified amounts.

A person of ordinary skill in the art can easily determine an appropriate dose of one of the instant compositions to administer to a subject without undue experimentation. Typically, a physician will determine the actual dosage which will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calit), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

REFERENCES FOR DETAILED DESCRIPTION
OF THE INVENTION

1. Curtin J A, Fridlyand J, Kageshita T, et al. Distinct sets of genetic alterations in melanoma. N Engl J Med 2005; 353(20):2135-47.

2. Takata M, Murata H, Saida T. Molecular pathogenesis of malignant melanoma: A different perspective from the studies of melanocytic nevus and acral melanoma. Pigment Cell Melanoma Res 2010; 23(1):64-71.
3. Moan J, Cicarma E, Setlow R et al. Time trends and latitude dependence of uveal and cutaneous malignant melanoma induced by solar radiation. Dermatoendocrinol 2010; 2(1):3-8.
4. Yun J, Lee J, Jang J, et al. KIT amplification and gene mutations in acral/mucosal melanoma in korea. APMIS 2011; 119(6):330-5.
5. Kong Y, Si L, Zhu Y, et al. Large-scale analysis of KIT aberrations in chinese patients with melanoma. Clin Cancer Res 2011; 17(7):1684-91.
6. Singh S, Davis R, Alamanda V, et al. Rb-Raf-1 interaction disruptor RRD-251 induces apoptosis in metastatic melanoma cells and synergizes with dacarbazine. Mol Cancer Ther. 2010; 9(12):3330-41.
7. Eggermont A M, Kirkwood J M. Re-evaluating the role of dacarbazine in metastatic melanoma: what have we learned in 30 years? Eur J Cancer 2004; 40:1825-36.
8. Daponte A, Ascierto P A, Gravina A, et al. Temozolomide and cisplatin in avdanced malignant melanoma. Anticancer Res. 2005; 25(2B):1441-7.
9. Baudy A R, Dogan T, Flores-Mercado J E, et al. FDG-PET is a good biomarker of both early response and acquired resistance in BRAFV600 mutant melanomas treated with vemurafenib and the MEK inhibitor GDC-0973. EJNMMI Res 2012; 2(1):22.
10. Yang H, Higgins B, Kolinsky K, et al. RG7204 (PLX4032), a selective BRAFV600E inhibitor, displays potent antitumor activity in preclinical melanoma models. Cancer Res 2010; 70(13):5518-27.
11. Neyns B, Seghers A C, Wilgenhof S, Lebbe C. Successful rechallenge in two patients with BRAF-V600-mutant melanoma who experienced previous progression during treatment with a selective BRAF inhibitor. Melanoma Res 2012 May 11. [Epub ahead of print]
12. Kudchadkar R, Paraiso K H, Smalley K S. Targeting mutant BRAF in melanoma: current status and future development of combination therapy strategies. Cancer J 2012; 18(2):124-31.

The following examples are offered by way of illustration and not by way of limitation.

6. EXAMPLES

6.1 Example 1: CHCM1/CHCHD6, a Novel Mitochondrial Protein Linked to Regulation of Mitofilin and Mitochondrial Cristae Morphology Summary The structural integrity of mitochondrial cristae is crucial for mitochondrial functions; however, the molecular events controlling the structural integrity and biogenesis of mitochondrial cristae remain to be fully elucidated. This example demonstrate the functional characterization of a novel mitochondrial protein named CHCM1 (Coiled coil Helix Cristae Morphology 1)/CHCHD6. CHCM1/CHCHD6 harbors a Coiled coil Helix-Coiled coil Helix (CHCH) domain at its carboxyl-terminal end and predominantly localizes to mitochondrial inner membrane. CHCM1/CHCHD6 knockdown causes severe defects in mitochondrial cristae morphology. The mitochondrial cristae in CHCM1/CHCHD6-deficient cells become hollow with loss of structural definitions and reduction in electron-dense matrix. CHCM1/CHCHD6 depletion also leads to reductions in cell growth, ATP production and oxygen consumption. CHCM1/CHCHD6 through its carboxyl-terminal end strongly and directly interacts with mitochondrial inner membrane protein Mitofilin that is known to also control mitochondrial cristae morphology. CHCM1/CHCHD6 also interacts with other Mitofilin-associated proteins including DISC1 and CHCHD3. Knockdown of CHCM1/CHCHD6 reduces Mitofilin protein levels; conversely, Mitofilin knockdown leads to reduction in CHCM1 levels, indicating coordinate regulation between these proteins. The results further indicate that genotoxic anticancer drugs that induce DNA damage down-regulate CHCM1/CHCHD6 expression in multiple human cancer cells whereas mitochondrial respiratory chain inhibitors do not affect CHCM1/CHCHD6 levels. CHCM1/CHCHD6 knockdown in human cancer cells enhances chemosensitivity to genotoxic anticancer drugs whereas its overexpression increases resistance. Collectively, the results indicate that CHCM1/CHCHD6 is linked to regulation of mitochondrial cristae morphology, cell growth, ATP production and oxygen consumption, and highlight its potential as a possible target for cancer therapeutics.

INTRODUCTION

Mitochondria are key organelles that contain double membranes and harbor their own DNA as well as components of transcriptional and translational machinery. They are implicated in a variety of processes including energy or free radical generation, regulation of apoptosis and modulation of various signaling pathways. Defects in mitochondrial function have been associated with a variety of pathological states including but not limited to neurogenic muscle weakness, ataxia and retinitis pigmentosa, mitochondrial encephalomyopathy lactic acidosis, stroke-like episodes, myoclonic epilepsy and ragged-red fibers, Leber hereditary optic neuropathy and Kearns-Sayre syndrome (1, 2). There is also a strong link between alterations in mitochondrial function and a variety of cancers (1, 3-5).

Mitochondria are dual membrane organelles that contain an outer membrane and an inner membrane. Although several models of mitochondrial inner membrane topology have been proposed, it is generally believed that within the inner membrane there exist an inner boundary membrane (IBM) and the cristae membrane (CM) (6). The IBM is believed to be in a closer proximity of the outer membrane while CM extends into the mitochondrial matrix and these membranes are joined via cristae junctions. Thus, the mitochondrial cristae are formed by the inner membrane folds extending as invaginations (6). Although the exact molecular mechanisms as to how mitochondrial cristae and cristae junctions are formed are not understood, emerging evidence suggests that the integrity of mitochondrial cristae morphology is important for mitochondrial structure and function. For example, mitochondrial cristae remodeling has been proposed to affect mitochondrial storage and release of cytochrome c (7-9). It has also been proposed that OPA1 and Parl play an important role in regulation of cristae remodeling (7-9). Other proteins including Mitofilin, MICS1, FIFO ATP synthase, DISC1 and ChChd3 have also been reported to be involved in regulation of mitochondrial cristae morphology (10-14). The molecular mechanisms that control the structural integrity and biogenesis of mitochondrial cristae remain to be fully elucidated and identification of additional molecules are expected to greatly improve the understanding of these events.

In this example, we report the identification and characterization of a mitochondrial protein CHCM1 (Coiled coil Helix Cristae Morphology 1) that is also linked to controlling mitochondrial cristae structures. The nucleotide and amino acid sequences of CHCM1 are deposited in the GenBank database, under accession # JF264889. A sequence corresponding to CHCM1 was found to be annotated in the database as a hypothetical protein CHCHD6 without experimental characterization. The results indicate that the presence of CHCM1 (hereafter referred to in this example as CHCM1/CHCHD6) is critical for maintaining the mitochondrial cristae morphology, ATP production as well as oxygen consumption. CHCM1/CHCHD6 predominantly localizes to the mitochondrial inner membrane and strongly interacts with Mitofilin, another mitochondrial inner membrane protein. CHCM1/CHCHD6 is regulated in response to DNA damage (genotoxic stress) and alterations in its expression affect chemosensitivity of human cancer cells to genotoxic anticancer drugs.

Experimental Procedures

Cell Culture, Antibodies and Reagents

Cell lines HEK293T (human embryonic kidney cells), MCF7 (human breast cancer cells), RKO (human colon cancer cells), MDA231 (human breast cancer cells), MDA468 (human breast cancer cells), Hs578T (human breast cancer cells), UACC-62 (human melanoma cells) and SK-Mel-103 (human melanoma cells) were maintained in Dulbecco's modified Eagle's medium (DMEM) supplemented with 10% fetal bovine serum (Gemini Bio-Products Inc., West Sacramento, Calif.). Human breast cancer cell line BT549 was maintained in RPMI-1640 medium supplemented with 10% fetal bovine serum. The following antibodies were used in the studies in this example: anti-HA-tag (clone 3F10) (Roche Applied Science, Indianapolis, Ind.); anti-β-actin (Sigma-Aldrich Corp., St. Louis, Mo.); anti-VDAC1 (Calbiochem, EMD Chemicals Group, Darmstadt, Germany); anti-Mitofilin (Protein Tech Group, Chicago, Ill.); anti-p97 (Fitzgerald Industries International, Concord, Mass.); anti-Tim23 (BD Biosciences, San Diego, Calif.); anti-S-tag (Novagen, EMD Biosciences, Darmstadt, Germany); anti-GST (GenScript, Piscataway, N.J.); anti-Hsp60 (Enzo Life Sciences, Plymouth Meeting, Pa.); anti-Smac (Upstate Cell Signaling Solutions, Lake Placid, N.Y.), anti-CHCHD3 (Abcam, San Francisco, Calif.), anti-DISC1 (Santa Cruz Biotechnology, Santa Cruz, Calif.). Rabbit polyclonal antibodies specific for human CHCM1/CHCHD6 were generated using routine methods using a commercial source (ProSci Inc., Poway, Calif.) using full-length recombinant human CHCM1/CHCHD6 protein purified from *E. coli*. For cell transfections Lipofectamine 2000 (Invitrogen, Carlsbad, Calif.) was used. Restriction endonucleases for subcloning were from New England BioLabs (Ipswich, Mass.). Pfu DNA polymerase was from Stratagene (La Jolla, Calif.). Chemical reagents used in transmission electron microscopy experiments were from Electron Microscopy Sciences (Hatfield, Pa.) and Polysciences Inc. (Warrington, Pa.). Other chemical reagents were from Thermo Fisher Scientific (USA) and Sigma-Aldrich Corp. (St. Louis, Mo.).

Expression Constructs

Clones containing cDNAs of CHCM1/CHCHD6 and Mitofilin were purchased from ATCC (Manassas, Va.) and Open Biosystems (Huntsville, Ala.) respectively. Fragments corresponding to open reading frames (ORFs) of CHCM1/CHCHD6, Mitofilin and CHCM1/CHCHD6 deletion variants were generated by PCR amplification. ORF of CHCM1/CHCHD6 and its deletion variants were inserted into pSRα-HA-S and pET30a (Novagen, EMD Chemicals Group, Darmstadt, Germany) expression vectors respectively. HA-S tagged-CHCM1/CHCHD6-pcDNA3.1 expression construct was obtained by inserting CHCM1/CHCHD6 ORF into pcDNA3.1 mammalian expression vector (Invitrogen, Carlsbad, Calif.). GST-tagged-Mitofilin was generated by inserting ORF of Mitofilin into pGEX6P-1 expression vector (GE healthcare, Piscataway, N.J.). All vectors were sequenced to validate their authenticity.

Stable Transfection

For stable transfections, expression vector pcDNA3.1 carrying HA/S-tagged CHCM1/CHCHD6 was used. The same vector without CHCM1/CHCHD6 insert was used for control transfection. RKO human colon cancer cells were transfected with these vectors using Lipofectamine 2000 (Invitrogen, Carlsbad, Calif.) and G418-resisitant colonies selected after approximately 2 weeks. Several independent colonies were picked up and expanded into mass culture and screened for the expression of exogenous CHCM1/CHCHD6. Several vector-only transfected colonies were also isolated, pooled and expanded into mass culture. CHCM1/CHCHD6 expressing clones B4, C3 and C4 were selected for further studies.

Immunostaining

Immunostaining of exogenous CHCM1/CHCHD6 tagged with HA was performed as previously described with some modifications (15). Briefly, cells were cultured in Lab-tek II chamber slides and then transiently co-transfected with pSRα-HA expression vector alone or CHCM1/CHCHD6-HA-pSRα expression construct with pDsRed2-Mito (Clontech Laboratories, Mountain View, Calif.) respectively. After approximately 24 hr, cells were fixed with 4% paraformaldehyde for 30 min followed by methanol (−20° C.) for 10 min and acetone (−20° C.) for 10 sec. Then anti-HA primary antibody and FITC-conjugated secondary antibody (Jackson Immuno Research Laboratories, West Grove, Pa.) were used to label cells. Nuclear staining was with DAPI nuclear dye. Slides were observed under an Olympus fluorescent microscope using the appropriate filters.

Immunostaining of endogenous CHCM1/CHCHD6 was performed as previously described with minor modifications (16). Briefly, cells were cultured in Lab-tek II chamber slides and stained with MitoTracker® according to manufacturer's protocols (Molecular Probes®/Invitrogen, Carlsbad, Calif.). Then cells were fixed with 4% paraformaldehyde for 30 min after that incubated with PBS buffer for 5 min and PBS+ 0.1% Triton-X 100 buffer for 10 min Later cells were subjected to an incubation for 1 hr with PBS+1% BSA+ 0.05% Triton-X 100 buffer at room temperature. Finally, cells were incubated with normal rabbit IgG alone or anti-CHCM1/CHCHD6 primary antibody diluted (1:600) in PBS+0.05% Triton-X 100 buffer respectively at 4° C. overnight. The next day cells were washed with PBS+1% BSA buffer for 3 times, 10 min each. Then, as a secondary antibody, FITC-conjugated anti-rabbit antibody was employed; DAPI was used for nuclear staining and slides were analyzed using an Olympus fluorescent microscope that had the required filters.

Isolation and Fractionation of Mitochondria

Isolation and fractionation of mitochondria were performed according to standard procedure (17). Briefly, cells were harvested by 600×g centrifugation for 10 min. After washing with cold PBS once, cells were re-suspended with 5 volumes of homogenization buffer (0.25 M sucrose; 20 mM HEPES-KOH, pH7.5; 10 mM KCl; 1.5 mM $MgCl_2$; 1 mM EDTA; 1 mM EGTA; 1 mM dithiothreitol and 0.1 mM PMSF). The suspension was subsequently homogenized with a Dounce-glass homogenizer and the mixture was centrifuged 750×g at 4° C. for 15 min. Supernatant was collected and centrifuged 10,000×g at 4° C. for 15 min. The pellet was obtained which represented crude mitochondria and the supernatant was further centrifuged at 100,000×g for 1 hr to obtain cytosolic fraction.

Submitochondrial Fractionations

RKO human colon cancer cells were used for generating submitochondrial fractions. Mitochondria from these cells were isolated and gradient purified as described previously (18). Briefly, cells were harvested by low-speed centrifugation and re-suspended in homogenization buffer (10 mM NaCl, 1.5 mM $MgCl_2$ and 10 mM Tris-HCl, pH7.5). The suspension was incubated on ice for 4-5 min, homogenized in a Dounce-glass homogenizer and subsequently transferred to sucrose-containing $T_{10}E_{20}$ buffer (10 mM Tris-HCl, 1 mM EDTA, pH7.6) with final sucrose concentration at 250 mM. After centrifugation 1300×g for 3 min, supernatant was isolated and centrifuged 1300×g for additional 3 min. The supernatant was further centrifuged 15,000×g for 15 min and crude mitochondria portioned in the pellet fraction. The crude mitochondrial fraction was washed three times with 250 mM sucrose in $T_{10}E_{20}$ buffer and layered on a discontinuous sucrose gradient (1.0 and 1.7 M sucrose in $T_{10}E_{20}$ buffer) and centrifuged at 70,000×g for 40 min. The mitochondrial fraction from the interface between two layers was recovered and diluted with an equal volume of 250 mM sucrose in $T_{10}E_{20}$ buffer and purified mitochondria were obtained after 15,000×g centrifugation for 15 min.

To prepare mitochondrial subfractionations, we used swell-contract method as reported previously (19, 20). Briefly, purified mitochondria were suspended in 20 mM potassium phosphate (pH7.2) containing 0.02% BSA on ice for 20 min, ATP and $MgCl_2$ were then added at a final concentration of 1 mM and incubated on ice for additional 5 min. The mixture was centrifuged at 10,000×g for 10 min and the recovered pellet was re-suspended in suspension buffer (0.25 M sucrose, 1 mM EGTA and 10 mM HEPES-NaOH, pH7.4) and centrifuged at 10,000×g for 10 min to recover mitoplasts in the pellet fraction. All supernatants were collected and centrifuged at 100,000×g for 1 hr. The final supernatant represented intermembrane space fraction and the pellet fraction corresponded to outer membrane fraction. Mitoplast fraction was re-suspended in suspension buffer without BSA and an equal volume of lysis buffer (25 mM HEPES, pH7.0 containing 1% Triton X-100) was added. The mixture was incubated on ice for 30 min and finally centrifuged at 100,000×g for 1 hr to recover matrix fraction in the supernatant and the inner-membrane fraction in the pellet.

Sodium Carbonate Extraction Assay

Sodium carbonate extraction assay was performed according to previously published reports (21, 22). Briefly, RKO or MCF-7 cells were homogenized with a Dounce-glass homogenized in a buffer composed of 250 mM sucrose, 10 mM Tris-HCl, pH7.4, 1 mM DTT, 1 mM EDTA and protease inhibitors and the mixture was centrifuged at 100,000×g for 1 hr to separate membrane and soluble fractions. Then about 60 μg of membrane proteins were diluted 50 folds in 100 mM sodium carbonate (pH 11.5) and incubated on ice for 30 min. The suspension was centrifuged 240,000×g for 1 hr at 4° C. Membrane-associated fraction portioned in the supernatant was precipitated with trichloroacetic acid (TCA) while the pellet representing the membrane integral fraction was dissolved in 1× protein loading buffer.

Northern Blot Analyses

Northern blot analyses were done according to standard procedure (23, 24). Briefly, total RNA was extracted by Trizol reagent (Invitrogen, Carlsbad, Calif.) and ~15 μg of total RNA were size-separated on 1.2% agarose gel and transferred to nylon membrane (Whatman, GE Health care, Piscataway, N.J.). Human CHCM1/CHCHD6 cDNA probe was labeled with $^{32}P$ and hybridization was performed in QuikHyb solution (Stratagene, La Jolla, Calif.) at 65° C.

Western Blotting, S-Tag Pull-Down and Immunoprecipitation

Western blotting and immunoprecipitations were done by standard procedures as previously described (25, 26). S-tag pull down experiments were performed using human cancer cells as well as bacterial lysates. Cell pellets were prepared and lysed in lysis buffer (50 mM Tris-HCl, pH 7.4, 120 mM NaCl, 0.1% NP-40, 10 mM NaF, 5 mM EDTA, 2 mM $Na_3VO_4$, 2 mM $MgCl_2$, 10 mM KCl, 25 mM glycerophosphate, protease inhibitor cocktail, okadic acid and 1 mM PMSF) and S-tag pull down was performed by using S-protein agarose beads (Novagen, EMD Chemicals Group, Darmstadt, Germany) according to manufacturer's protocol. For S-tag pull down using bacterial lysates, wild type and deletion variants of S-tagged CHCM1/CHCHD6 were expressed in *E. coli* BL21 (DE3) and induced by 1 mM IPTG (isopropyl-1-thio-β-D-galactopyranoside) at 30° C. for 6 hr. Bacteria were lysed in a buffer containing 28 mM Tris, 135 mM NaCl, 1 mM dithiothreitol (DTT), 1% Triton-X 100 (w/v), protease inhibitor cocktail and 400 μg/ml lysosome for 30 min at room temperature, followed by 26,000×g centrifugation for 30 min (Sorvall RC5C Plus) and S-tag pull down was done according to manufacturer's protocol. GST-tagged Mitofilin was expressed in bacteria and gel-purified as previously described (27).

RNA Interference (RNAi)

Endogenous CHCM1/CHCHD6 and Mitofilin were knocked-down by lentiviral shRNA-mediated approach (28). The pLKO.1 lentiviral vectors containing the scrambled or CHCM1/CHCHD6-specific shRNAs or Mitofilin-specific shRNAs were generated by The RNA interference Consortium and purchased from Open Biosystems (Huntsville, Ala.). Lentiviruses were produced and titered according to the supplier's protocols. In all experiments, the multiplicity of infection (M.O.I.) was 1.0. Five shRNAs to target five different regions of CHCM1/CHCHD6 were used. Artificial DNA sequences coding for shRNAs are as follows. The first part of the sequence is in sense orientation then loop (underlined) followed by antisense sequence:

```
CHCM1/CHCHD6-specific shRNA-G4:
                                    (SEQ ID NO: 3)
GAGCGTATTGAGAGGAAGAATCTCGAGATTCTTCCTCTCAATACGCTC
T, CHCM1/CHCHD6-specific shRNA-G5:
                                    (SEQ ID NO: 4)
CCTGAAGAAGGGACCAATCATCTCGAGATGATTGGTCCCTTCTTCAGG
T, CHCM1/CHCHD6-specific shRNA-G6:
                                    (SEQ ID NO: 5)
GCATGCTGCTATCCAGGATAACTCGAGTTATCCTGGATAGCAGCATGC
T,
```

```
CHCM1/CHCHD6-specific shRNA-G7:
                                         (SEQ ID NO: 6)
CTTTGGCCTTCAAGATGGCAACTCGAGTTGCCATCTTGAAGGCCAAAG

T,

CHCM1/CHCHD6-specific shRNA-G8:
                                         (SEQ ID NO: 7)
GCTGAGATGTATAAACTGTCTCTCGAGAGACAGTTTATACATCTCAGC

T.
```

The following four shRNAs to target four different regions of Mitofilin were used. Artificial DNA sequences encoding the shRNAs are as follows. The first part of the sequence is in sense orientation then loop (underlined) followed by antisense sequence):

```
Mitofilin-specific shRNA-A1:
                                         (SEQ ID NO: 8)
CCGGGCTAAGGTTGTATCTCAGTATCTCGAGATACTGAGATACAACCTT

AGCTTTTTG,

Mitofilin-specific shRNA-A2:
                                         (SEQ ID NO: 9)
CCGGCCAAGCTTTAACCGCAGCTATCTCGAGATAGCTGCGGTTAAAGCT

TGGTTTTTG,

Mitofilin-specific shRNA-A3:
                                        (SEQ ID NO: 10)
CCGGGCACTATCCTATATGCCAAATCTCGAGATTTGGCATATAGGATAG TGCTTTTTG,
and Mitofilin-specific shRNA-A4:
                                        (SEQ ID NO: 11)
CCGGGTCTAGAAATGAGCAGGTTTACTCGAGTAAACCTGCTCATTTCTA

GACTTTTTG.
```

MTT Assay

MTT powder (MTT, Methylthiazolyldiphenyl-tetrazolium bromide, available from Sigma-Aldrich, St. Louis, Mo., Cat. No. M2128) was dissolved in DMEM without fetal bovine serum and phenol red to a final concentration of 1 mg/ml and then added to cells and incubated for ~1-4 hrs depending on cell confluency. Medium was then removed and equal volume of isopropanol with 0.04N HCl was added to dissolve the precipitate. Finally, absorbance was read at 570 nm wavelength subtracting background reading at 650 nm wavelength with a Bio-Rad Smart-Spec 3100 instrument.

Transmission Electron Microscopy

Scramble and CHCM1/CHCHD6 knockdown cells were harvested and fixed by Ito and Karnovsky's fixative (2.5% glutaraldehyde, 2% paraformaldehyde in 0.1 M cacodylate buffer, pH 7.4) at 4° C. overnight (29). The next day cells were rinsed with 0.1 M cacodylate buffer for 5 times, 5 min each. After fixing with 1% osmium tetroxide in 0.1 M cacodylate buffer for 1 hr on ice, the samples were rinsed with double-distilled $H_2O$ for 3 times, 8 min each and later fixed with 1% Tannic acid for 1 hr. After rinsing with double-distilled $H_2O$ for additional 3 times 8 min each, samples were dehydrated and embedded into Poly/Bed® 812 according to the protocol of Poly/Bed® 812 BDMA Mini-kit (Polyscience, Inc., Warrington, Pa.). Poly/Bed®-embedded cells were cut into 80-90 nm ultrathin serial sections by a diamond knife-DIATOME 45 degree (Diatome U S, Hatfield, Pa.). Sections were supported on nickel grids/200 mesh (Electron Microscopy Sciences, Hatfield, Pa.) and post-stained in 4% uranyl acetate and 4% lead citrate. Finally sections were observed under Tecnai™ Transmission Electron Microscope (BioTwin lens) with Advantage Plus CCD Camera System at an 80.0-kV acceleration voltage.

Mitochondrial ATP Synthesis Assay

Mitochondrial ATP synthesis assay was performed as reported previously (30). Briefly, CHCM1/CHCHD6 knockdown or scramble knockdown RKO cells were harvested, washed with glucose-free, serum free DMEM. Each sample with approximately $1.5 \times 10^6$ cells were re-suspended and incubated in 160 µl of buffer A (150 mM KCl, 25 mM Tris-HCl, 2 mM EDTA, 0.1% BSA, 10 mM potassium phosphate, pH 7.4, 0.1 mM $MgCl_2$) with digitonin (40 µg/ml final concentration) for 1 min at room temperature. After a wash with buffer A, cells were centrifuged at 800×g at room temperature and pellets were re-suspended in 160 µl buffer A containing $P^1$, $P^5$-di (adenosine) pentaphosphate (0.15 mM). Subsequently, 10 µl of buffer B (0.5 M Tris-acetate, pH 7.75, 0.8 mM luciferin, 20 µg/ml luciferase), ADP (to 0.1 mM), malate and pyruvate (both to 1 mM) were added to the cell suspension. Oligomycin (1 µg/ml) was also added to one replicate of each sample prepared as above. Cells were transferred to a luminometer glass tubes and gently mixed with a vortex for 2 sec. Tubes were then placed in a luminometer (LUMAT LB 9507, Berthold Technologies, Germany) and light emission was recorded in the kinetic mode. The integration time for each reading was 1 sec. Interval between readings was 15 sec and a total recording time was 4 min. Finally, total cellular protein content of each sample was determined.

Oxygen Consumption Rate Measurement

Intact cell oxygen consumption rate was measured by an Oxygraph system with DW1 Oxygen Electrode (Hansatech Instruments Ltd., Norfolk, U. K.) as described previously (30). Briefly, RKO cells with CHCM1/CHCHD6 knockdown or scramble knockdown were harvested by trypsinization and centrifugation at 2500 rpm. Approximately $1.5 \times 10^6$ cells were re-suspended in 300 µl growth medium for each sample and injected into the polarographic chamber for the intact cell-coupled oxygen consumption rate.

Statistical Analysis

The MTT assay data for the evaluation of cancer cell proliferation and chemosensitivity as well as cellular ATP production assay and oxygen consumption assay reported in this study were expressed as the mean±SEM of three independent experiments. Statistical analysis was performed with One-tailed Student's t-test. The value of $P<0.05$ was considered as statistically significantly.

Results

CHCM1/CHCHD6 is a Novel Mitochondrial Protein.

Tee identification and characterization of several novel stress regulated proteins including PDRG1, SKNY, DOC45, RBEL1 has been previously reported (24-25, 32-34). CHCM1/CHCHD6 was also identified in efforts to identify novel markers of cellular stress response. In particular, CHCM1/CHCHD6 was identified as one of several BBEL1-interacting proteins.

We performed a standard proteomic screen involving S-tag pull-down and mass spectrometry assays and identified several BBEL1-interacting proteins including CHCM1/CHCHD6. Sequence corresponding to CHCM1 was found to be annotated in the database as a hypothetical protein (CHCHD6) indicating it to be a novel previously uncharacterized protein. An EST (expression sequence tag; ATCC)

cDNA corresponding to CHCM1/CHCHD6 was sequenced and found to contain an open reading frame composed of 235 amino acids with a predicated molecular mass of 26.5 kDa. CHCM1/CHCHD6 is predicted to have a myristylation site (MGSTESSEGRRVSFGVDE) at the N-terminal end and a Coiled coil Helix-Coiled coil Helix (CHCH) domain at its C-terminal end harboring twin $CX_9C$ structural motifs (FIG. 1A). In addition, a DUF737 domain (Domain of Unknown Function) is present at the N-terminus (FIG. 1A).

To ensure that the cDNA corresponding to CHCM1/CHCHD6 encodes a bona fide protein of expected size, we constructed expression vectors in which CHCM1/CHCHD6 cDNA was tagged with HA-S-tag both at the N- or C-termini and transfected into HEK293T cells and its expression was detected by Western blotting. The representative results shown in FIG. 1B indicate that the expression vector carrying CHCM1/CHCHD6 expressed CHCM1/CHCHD6 protein in the expected size range, a finding which confirmed that CHCM1/CHCHD6 cDNA encoded a bona fide protein. Of note, the N-tagged construct has three HA-tags while the C-tagged construct only one and hence, the CHCM1/CHCHD6 expressed by the former is larger in mass and migrates slower. The C-tagged construct was used in all subsequent experiments.

Next, we sought to investigate the subcellular distribution of CHCM1/CHCHD6 and to that end, we transiently co-transfected HA-tag vector-alone or expression vector carrying HA-tagged CHCM1/CHCHD6 along with pDsRed2-Mito vector [which expresses RFP (red fluorescent protein) in mitochondria] into MCF7 human breast cancer cells and performed immunostaining using anti-HA antibody. The results shown in FIG. 2A indicate that exogenous CHCM1/CHCHD6 displayed localization similar to that noted for mitochondrial RFP (red), indicating that CHCM1/CHCHD6 is a mitochondrial protein (FIG. 2A). Cells transfected with HA-tag vector-alone without CHCM1/CHCHD6 insertion did not display immunofluorescent pattern resembling that noted for CHCM1/CHCHD6 and thus, served as a negative control (data not shown).

We also investigated subcellular localization of endogenous CHCM1/CHCHD6 using a polyclonal antibody generated against purified CHCM1/CHCHD6 using routine methods. Results in FIG. 2B indicate that endogenous CHCM1/CHCHD6 displayed mitochondrial localization as well.

We also performed cellular fractionations to determine the sub-cellular distribution of CHCM1/CHCHD6. Results obtained from multiple cells lines shown in FIG. 2C indicate that endogenous CHCM1/CHCHD6 was predominantly detected in the mitochondrial fractions. The same blots were also probed to detect Tim23 that is a known mitochondrial protein and as expected, Tim23 was detected in the mitochondrial fractions (FIG. 2C). Using the same approach, we also analyzed subcellular localization of exogenous CHCM1/CHCHD6 and that was also predominantly detected in the mitochondrial fractions (data not shown). Taken together, these results indicate that CHCM1/CHCHD6 is a bona fide mitochondrial protein.

Next, we investigated the submitochondrial localization of CHCM1/CHCHD6 and thus performed the sucrose gradient centrifugation to enrich purified mitochondria that were subsequently subjected to ultracentrifugations to separate outer membrane (OM), intermembrane space (IMS), inner membrane (IM) and matrix (M) fractions. These fractions were then analyzed by Western blotting and as is shown (FIG. 3A), CHCM1/CHCHD6 was not detected in the OM or IMS fraction but was predominantly present in the IM fraction and a trace amount was detected also in the M fraction. We also analyzed the submitochondrial distributions of other proteins such as Mitofilin, Smac, HSP60 and VDAC1 that have been reported to localize to different mitochondrial compartments.

As shown in FIG. 3A, Hsp60, which is known to predominantly reside in the matrix, was also detected in the matrix with trace amounts detected in the OM and IM fractions (panel, lanes 2 and 4), a finding consistent with those reported by others that Hsp60 can be detected at other sites (35-37). VDAC1 is known to reside in the mitochondrial OM and has been reported to also localize to other subcellular sites including plasma membrane and the ER (38-39). As expected, VDAC1 was found in the OM fraction but not in the IMS or M fraction although it was also detected in the IM fraction (FIG. 3A). Smac is an IMS protein and as expected, it was detected in the IMS fraction (FIG. 3A). Smac was also detected in the M fraction but not in the OM or IM fraction (FIG. 3A) which may be consistent with recently reported findings that modified smac localized to the matrix (40). Mitofilin is a known IM protein (41-42) and, as expected, it was detected predominantly in the IM fraction but not in the OM, IMS and M fractions (FIG. 3A). Thus, the sub-mitochondrial distribution pattern of CHCM1/CHCHD6 is largely similar to that of Mitofilin's (FIG. 3A, lane 4), a finding that indicates that CHCM1/CHCHD6 appears to predominantly localize to the mitochondrial inner membrane.

Computer-based protein structural analyses did not reveal CHCM1/CHCHD6 to contain hydrophobic transmembrane regions. We therefore performed a sodium carbonate extraction assay to determine whether CHCM1/CHCHD6 was an integral membrane protein or a membrane-associated protein. Cellular proteins were first separated into two fractions: (i) a soluble fraction ($S_{100}$) and (ii) non-soluble fraction that contained integral membrane proteins as well as membrane-associated proteins. The non-soluble fraction was treated with sodium carbonate to dissociate non-integral membrane-associated proteins. The sodium carbonate-treated lysates were subsequently separated by ultra-centrifugation to obtain membrane-associated proteins (supernatants, $S_{240}$) and the integral membrane proteins (pellets, $P_{240}$). Western blot analyses were performed to analyze these fractions to detect CHCM1/CHCHD6 as well as markers of membrane-associated (p97) and integral membrane (Tim23) proteins.

As shown in FIG. 3B, CHCM1/CHCHD6 was not detected in the soluble ($S_{100}$) fraction (lane 1) but high levels of CHCM1/CHCHD6 were detected in the membrane-associated ($S_{240}$) fraction (lane 2). Small amount of CHCM1 was also detected in the $P_{240}$ fraction (lane 3). As expected, p97, a non-integral membrane-associated protein, was detected in the $S_{100}$ and $S_{240}$ fractions (lanes 1 and 2). Similarly, Tim23, an integral membrane protein, was predominantly detected in the $P_{240}$ fraction (lane 3). Together, these results indicate that CHCM1/CHCHD6 appears to be a membrane-associated protein.

Genotoxic Stress Down-Regulates CHCM1/CHCHD6

CHCM1/CHCHD6 is a mitochondrial protein and certain mitochondrial proteins have been found to affect cell growth, cell death and are also regulated in response to anti-cancer drug treatment. Therefore, we sought to investigate the effect of anticancer drugs including etoposide and ADRIAMYCIN® (doxorubicin) that induce DNA damage (genotoxic stress) using various human cancer cell lines representing different malignancies. The results indicated that these drugs strongly down-regulated CHCM1/CHCHD6 expression. FIG. 4A shows representative Northern blot analyses indicating that etoposide (E) strongly down-regulated CHCM1/CHCHD6 mRNA expression in multiple human cancer cell lines (C: untreated controls; E: etoposide treated samples). Kinetics of mRNA down-regulation following ADRIAMYCIN® treatment (FIG. 4B) in RKO human colon cancer cells indicated that CHCM1/CHCHD6 expression was reduced within 12 hours and its effect was maintained until 60 hours post-treatment. Using anti-CHCM1/CHCHD6 antibody, we further confirmed that CHCM1/CHCHD6 was down-regulated by these genotoxic drugs also at the protein levels in multiple human cancer cell lines (FIG. 4C). Because CHCM1/CHCHD6 is a mitochondrial protein, we also investigated whether it was regulated by mitochondrial respiratory chain inhibitors including antimycin A and rotenone. Results shown in FIGS. 12A-B indicate that these agents did not appreciably affect the CHCM1/CHCHD6 levels.

CHCM1/CHCHD6 Depletion Reduces Cell Proliferation.

To gain insight into the function of CHCM1/CHCHD6, endogenous CHCM1/CHCHD6 was knocked down using a lentiviral shRNA approach. To this end, we utilized a number of lentiviral vectors expressing shRNAs namely G4, G5, G6, G7 and G8 each targeting different region of CHCM1/CHCHD6 mRNA. A lentiviral vector with a scrambled sequence as a control was also used. The knockdown efficiency was then tested in various human cancer cell lines. Representative results in FIG. 5A show that these constructs effectively knocked down endogenous CHCM1/CHCHD6 at mRNA and protein levels in RKO human colon and MCF-7 breast cancer cells. We next performed MTT assay to assess the effect of CHCM1/CHCHD6 deficiency in various human cancer cell lines and as shown in FIG. 5B, CHCM1/CHCHD6 knockdown led to significant reduction in cancer cell growth.

CHCM1/CHCHD6 Depletion or Overexpression Alters Chemosensitivity of Human Cancer Cells to Genotoxic Anticancer Drugs.

Because CHCM1/CHCHD6 was down-regulated following treatment with genotoxic anticancer drugs and that its depletion affected cancer cell growth, we also investigated the effect of CHCM1/CHCHD6 deficiency on cancer cell growth following treatment with genotoxic anticancer drugs. Results in FIG. 6A show that CHCM1/CHCHD6 knockdown further increased etoposide and ADRIAMYCIN®-mediated chemosensitivity of human cancer cells. We also established RKO human colon cancer cells stably expressing exogenous CHCM1/CHCHD6 and tested their chemosensitivity to etoposide. Results of two independent clones (C3 and C4) are shown in FIG. 6B and as is shown, increased expression of exogenous CHCM1/CHCHD6 in RKO cells resulted in reduced etoposide-mediated chemosensitivity.

CHCM1/CHCHD6 Interacts with Mitofilin, CHCHD3 and DISC1.

CHCM1/CHCHD6 exhibits mitochondrial distribution. Mitofilin, a known mitochondrial protein, was also present along with CHCM1/CHCHD6 in a previous proteomic screen when we tried to find BBEL1 interacting proteins. In a study reported by Xie et al. (43), Mitofilin was found to be present in a complex with multiple proteins including the hypothetical protein CHCHD6 that corresponds to CHCM1. We therefore, sought to investigate mutual interactions between CHCM1/CHCHD6 and Mitofilin. First, we performed S-tag pull down assay using cell lysates from RKO cells stably expressing exogenous S-tagged CHCM1/CHCHD6. The results in FIG. 7A show that exogenous CHCM1/CHCHD6 strongly interacted with endogenous Mitofilin. Next, we performed immunoprecipitation with anti-CHCM1/CHCHD6 antibody and found that endogenous CHCM1/CHCHD6 also strongly interacted with endogenous Mitofilin (FIG. 7B). These results indicate that CHCM1/CHCHD6 also interacts with Mitofilin in cellulo.

To date, detailed characterization of Mitofilin interactions with two other proteins including DISC1 (Disrupted-in-schizophrenia1) and ChChd3 has been reported (13, 14). DISC1 is linked to neurodevelopment and believed to be important for Mitofilin stability (13), whereas CHCHD3 linked to maintaining mitochondrial cristae morphology (14). Therefore, we also investigated whether CHCM1/CHCHD6 interacts with CHCHD3 and/or DISC1.

First, we performed S-tag pull down assay using cell lysates representing crude mitochondrial-fractions from RKO cells stably expressing exogenous S-tagged CHCM1/CHCHD6. The results in FIG. 7C show that exogenous CHCM1/CHCHD6 interacted with endogenous CHCHD3 and DISC1. Next, we performed immunoprecipitations using anti-CHCM1/CHCHD6 antibodies and found that endogenous CHCM1/CHCHD6 also displayed interactions with endogenous CHCHD3 and DISC1 (FIG. 7D). These results indicate that CHCM1/CHCHD6 also interacts with both CHCHD3 and DISC1.

CHCM1/CHCHD6 is Linked to Maintaining Mitochondria Cristae Morphology.

Mitofilin has been reported to reside in the inner membrane of mitochondria and linked to maintaining mitochondrial cristae morphology (10, 41, 42). The results of this study confirmed that Mitofilin indeed localized to the inner mitochondrial membrane (FIG. 3A). Because the results indicated that CHCM1/CHCHD6 also predominantly localized to the inner membrane of mitochondria (FIG. 3A) and the fact that it interacted with Mitofilin, we sought to investigate whether CHCM1/CHCHD6 was also linked to maintaining mitochondrial cristae morphology.

To that end, we knocked down CHCM1/CHCHD6 in three different cells lines including RKO (human colon cancer), MCF-7 (human breast cancer) and A375 (human melanoma) cells, and analyzed mitochondrial morphology by transmission electron microscopy (TEM). The results indicated that CHCM1/CHCHD6 knockdown in all three cell lines altered mitochondrial morphology. Representative results for RKO and MCF-7 cells are shown in FIGS. 8A-B in which black arrows point to normal and white arrows indicate abnormal mitochondria. As is shown FIGS. 8A-B), the normal mitochondria in scrambled control cells had well-defined cristae structures whereas a larger number of mitochondria in the CHCM1/CHCHD6 knockdown cells (Table 1) displayed clearly altered cristae structures (FIGS. 8A-B). Table 1 below shows the percentages of mitochondria with abnormal cristae structures in scramble and CHCM1/CHCHD6 knockdown cells. These results thus, indicate that CHCM1/CHCHD6 is also linked to maintaining mitochondrial cristae morphology.

TABLE 1

Percentage of abnormal mitochondria devoid or nearly devoid of cristae structures inscramble and CHCM1/CHCHD6 knockdown cells

| Samples | Abnormal Mitochondria | |
|---|---|---|
| | Experiment 1 | Experiment 2 |
| RKO-scramble | 5.5% (5/91) | 2.8% (3/106) |
| RKO-CHCM1/CHCHD6 (KD-G8) | 55.6% (109/196) | 70.5% (74/105) |

TABLE 1-continued

Percentage of abnormal mitochondria devoid or nearly devoid of cristae structures inscramble and CHCM1/CHCHD6 knockdown cells

| Samples | Abnormal Mitochondria | |
|---|---|---|
| | Experiment 1 | Experiment 2 |
| RKO-CHCM1/CHCHD6 (KD-G4) | 17.8% (30/169) | |
| MCF7-scramble | 6.25% (11/176) | |
| MCF7-CHCM1/CHCHD6 (KD-G8) | 65.2% (723/1109) | |
| MCF7-CHCM1/CHCHD6 (KD-G4) | 58.3% (833/1428) | |

CHCM1/CHCHD6 Directly Interacts with Mitofilin Via its C-Terminus.

The preceding results indicate that CHCM1/CHCHD6 strongly interacts with Mitofilin (FIGS. 7A-D) and just like Mitofilin, CHCM1/CHCHD6 knockdown leads to alterations in mitochondrial cristae morphology (FIGS. 8A-B). We next undertook studies to (i) investigate whether CHCM1/CHCHD6 directly or indirectly interacts with Mitofilin and (ii) identify the region through which CHCM1/CHCHD6 interacts with Mitofilin.

First, we constructed two separate bacterial expression vectors: one carrying S-tagged CHCM1/CHCHD6 and another with GST-tagged Mitofilin. The expression vectors carrying CHCM1/CHCHD6 or Mitofilin were independently introduced into E. coli and the expressed proteins were purified. The purified proteins were then used to test their mutual interactions. Results in FIG. 9A show that indeed, the purified CHCM1/CHCHD6 and Mitofilin exhibited direct interactions (FIG. 9A, lane 4).

We next generated 4 deletion variants of CHCM1/CHCHD6 that were lacking 50 or 100 amino acids at their N- or C-terminal ends (FIG. 9B). These variants were introduced into bacterial expression vector with S tag at their N-terminal ends and then expressed in E. coli and purified. FIG. 9C shows Coomassie blue staining of purified full-length and deletion variants of CHCM1/CHCHD6 (denoted by *sign). S-tag pull-down assay was performed using purified CHCM1/CHCHD6 protein variants and gel-purified GST-tagged Mitofilin protein, and the resultant precipitants were analyzed by immunoblotting with anti-GST or anti-S-tag antibodies separately. The results (FIG. 9D) show that the full-length as well as deletions variants devoid of N-terminal 50 and 100 amino acids exhibited interactions with Mitofilin. However, the CHCM1/CHCHD6 deletion variants lacking the C-terminal 50 or 100 amino acids displayed reduced or absent interactions with Mitofilin (FIG. 9D lanes 7 and 8). These results indicate that the carboxyl-terminus of CHCM1/CHCHD6 including the CHCH domain appeared to be important for its interaction with Mitofilin.

CHCM1/CHCHD6 and Mitofilin are Coordinately Regulated.

The preceding results indicate that CHCM1/CHCHD6 directly interacts with Mitofilin and just like Mitofilin, it is linked to regulating mitochondrial cristae morphology. Next, we analyzed the effect of CHCM1/CHCHD6 knockdown on Mitofilin expression and found that CHCM1/CHCHD6 knockdown resulted in down-regulation of endogenous Mitofilin (FIG. 10A). In some cells, such as SK-mel103 melanoma cell line, CHCM1/CHCHD6 deficiency reproducibly led to a dramatic decrease in the endogenous Mitofilin levels whereas in some cells, including RKO colon and MCF-7 breast cancer cell lines, the decreases in Mitofilin levels were less dramatic or minimal varying from experiment to experiment.

We also performed the reverse experiments and investigated the effect of Mitofilin deficiency on CHCM1/CHCHD6 levels and noted that Mitofilin deficiency also led to a decrease in CHCM1/CHCHD6 levels (FIG. 10B). The effect of increased expression of CHCM1/CHCD6 was also analyzed using RKO colon cancer cells stably expressing exogenous CHCM1/CHCHD6 and as shown in FIG. 10C, overexpression of exogenous CHCM1/CHCHD6 increased expression level of endogenous Mitofilin. Together, these results indicate that the expression levels of both proteins are coordinately regulated and a crosstalk appears to exist between these two proteins modulating their regulation and function.

CHCM1/CHCHD6 Deficiency Induces Mitochondrial Dysfunction.

Because CHCM1/CHCHD6 knockdown affected mitochondrial cristae morphology, we also investigated the effect of CHCM1/CHCHD6 deficiency on mitochondrial function. To that end, we performed a luciferase-based assay to measure cellular and mitochondrial ATP synthesis in CHCM1/CHCHD6-proficient and -deficient cells. The results (FIG. 11A) indicated that CHCM1/CHCHD6 deficiency clearly affected total as well as mitochondrial ATP synthesis. We also compared oxygen consumption rate (OCR) in CHCM1/CHCHD6-proficient and -deficient cells and as shown in FIG. 11B, knockdown of CHCM1/CHCHD6 led to a clear decrease in OCR. These results thus indicate that CHCM1/CHCHD6 knockdown also affects mitochondrial function.

DISCUSSION

In this example, we report the identification and characterization of CHCM1/CHCHD6, a novel mitochondrial protein that predominantly localizes to the mitochondrial inner membrane. We have also found that the depletion of endogenous CHCM1/CHCHD6 alters mitochondrial cristae morphology. In CHCM1/CHCHD6 deficient cells, the affected mitochondrial cristae appear to be hollow with loss of structural definitions and reduction in electron-dense matrix. Published evidence indicates that the depletion of Mitofilin, another mitochondrial inner membrane protein, also alters mitochondrial cristae morphology (10, 41, 42). CHCM1/CHCHD6 strongly and directly interacts with Mitofilin. CHCM1/CHCHD6 appears to interact with Mitofilin through its C-terminal end, and the C-terminal 50 amino acids harboring the CHCH domain appear to be critical for these interactions. Furthermore, CHCM1/CHCHD6 and Mitofilin are coordinately regulated as Mitofilin levels are reduced in CHCM1/CHCHD6-deficient cells and CHCM1/CHCHD6 levels are decreased in Mitofilin knockdown cells. Thus, CHCM1/CHCHD6 and Mitofilin appear to be critical partners in maintaining the structural integrity of the mitochondrial cristae.

The molecular basis for the coordinate regulation between CHCM1/CHCHD6 and Mitofilin remains to be fully elucidated. Mitofilin is believed to exist in a larger protein complex. Both CHCM1/CHCHD6 and Mitofilin may reside in the same multi-protein complex and depletion of either one disrupts the complex formation. Previously published ultrastructural analysis of mitochondria from Mitofilin-deficient cells indicates that the mitochondrial inner membrane exhibits "onion-like concentric spherical" structures as well as layers of "tightly packed concentric-membranous sheets" (10).

By contrast, CHCM1/CHCHD6 knockdown more severely affects mitochondrial cristae structures, since most of the CHCM1/CHCHD6-deficient mitochondria are devoid of well-defined cristae structures. For example, in the CHCM1/CHCHD6-deficient cells, the affected mitochondrial cristae appear to be hollow with loss of structural definitions and reduction in electron-dense matrix. Thus, the mitochondrial ultrastructure alterations due to loss of Mitofilin are morphologically distinct from those noted, due to CHCM1/CHCHD6 depletion. CHCM1/CHCHD6, in addition to its interactions with Mitofilin, may exhibit crosstalk with other mitochondrial proteins to regulate structural integrity of mitochondrial cristae.

Mitofilin is believed to exhibit homotypic interactions in addition to its interactions with other mitochondrial proteins (10, 43). To date, Mitofilin interactions with two other proteins including DISC1 (Disrupted-in-schizophrenia1) and ChChd3 have been investigated in detail (13, 14). Alterations in DISC1 structure/function are linked to pathogenesis of schizophrenia that is believed to be a neuronal disorder (13). A portion of DISC1 has been reported to reside in mitochondria and interacts with Mitofilin. DISC1 deficiency is reported to be associated with mitochondrial dysfunction, Mitofilin ubiquitination and alterations in cristae morphology (13). The morphological features of cristae structures due to DISC1 depletion are similar to those noted due to Mitofilin deficiency. Therefore, alterations in the function of DISC1 and Mitofilin are thought to be linked to pathogenesis of schizophrenia (13). In this study, we have found that CHCM1/CHCHD6 also interacts with DISC1.

A more recent study has reported the identification and characterization of ChChd3 as a novel mitochondrial protein (14). ChChd3 localizes to the inner mitochondrial membrane and also interacts with Mitofilin. We have found that CHCM1/CHCHD6 also interacts with ChChd3. ChChd3 knockdown also leads to alterations in mitochondrial cristae morphology. Just like CHCM1/CHCHD6, ChChD3 also harbors a CHCH domain at its C-terminal end and exhibits 36% amino acid identity with CHCM1/CHCHD6. Furthermore, knockdown of ChChd3 results in reduced cell proliferation, and the morphological abnormalities of mitochondrial cristae due to chchd3 knockdown appear to be similar to those noted in CHCM1/CHCHD6-deficient cells. However, ChChd3 knockdown is reported to minimally affect the total cellular ATP levels whereas CHCM1/CHCHD6 knockdown profoundly affects the total cellular and mitochondrial ATP levels. Thus, CHCM1/CHCHD6 and chchd3 are two novel mitochondrial proteins that appear to exhibit similar and distinct characteristics. Furthermore, we have found that CHCM1/CHCHD6 deficiency is not associated with down-regulation of endogenous CHCHD3 (FIGS. 13A-B) a finding that indicates that mitochondrial dysfunction due to CHCM1/CHCHD6 deficiency does not appear to secondarily occur due to down-regulation of endogenous CHCHD3.

In addition to aforementioned proteins, OPA1 and MICS1 are two additional inner mitochondrial membrane proteins that are also linked to maintaining the integrity of cristae morphology (6, 7-9, 11). In the case of OPA1 depletion, the mitochondria display "reticular, curved and expanded" cristae structures (7-9) while MICS1 deficiency leads to "mild fragmentation, lump-like structures and short curved tubules" in mitochondrial cristae (11). Clearly, the morphologic features of mitochondrial cristae due to OPA1 or MICS1 deficiency are different from those noted due to Mitofilin, DISC1, ChChd3 or CHCM1/CHCHD6 depletion. OPA1 or MICS1 has not been reported to interact with Mitofilin; it will be interesting to investigate CHCM1/CHCHD6 interactions with OPA1 and/or MICS1 and their effects on its function.

It is evident that CHCM1/CHCHD6 appears to be needed for the structural integrity of mitochondrial cristae because mitochondrial ultrastructure alterations due to CHCM1/CHCHD6 deficiency are more severe than those noted due to the loss of Mitofilin and other mitochondrial proteins. Indeed, CHCM1/CHCHD6 depletion is associated with down-regulation of Mitofilin and such effect is more dramatic in some cells while in some cells Mitofilin down-regulation following CHCM1/CHCHD6 is not very robust. It is possible that CHCM1/CHCHD6 depletion-mediated alterations in mitochondrial cristae morphology could partly result due to concomitant down-regulation of Mitofilin. We have also found that CHCM1/CHCHD6 deficiency does not lead to down-regulation of endogenous CHCHD3 (FIGS. 13A-B). These findings would therefore, indicate that CHCM1/CHCHD6 depletion-mediated alterations in mitochondrial cristae morphology do not appear to occur through deficiency in CHCHD3 levels and thus, point to unique functional characteristic of CHCM1/CHCHD6 in maintaining mitochondrial cristae morphology. It is conceivable that CHCM1/CHCHD6 via its interactions with Mitofilin, CHCHD3 and DISC1 and/or with some of the other mitochondrial proteins may exert a tight control over structural integrity and biogenesis of mitochondrial cristae. CHCM1/CHCHD6 deficiency could lead to loss of its interactions with other proteins and that might severely affect the dynamics of these processes. It is possible that CHCM1/CHCHD6, directly or indirectly, also regulates and fine tunes the processing of other mitochondrial events as its expression is down-regulated, at both mRNA and protein levels, by genotoxic (DNA damage-inducing) anticancer drugs in human cancer cells. CHCM1/CHCHD6 knockdown affects cancer cell growth and enhances chemosensitivity to anticancer drugs. By contrast, increased expression of exogenous CHCM1/CHCHD6 desensitizes cancer cells to these agents. These findings therefore, also highlight the potential of CHCM1/CHCHD6 as a possible target for cancer therapeutics.

REFERENCES FOR EXAMPLE 1

1. Czarnecka, A. M., Gammazza, A. M., Di Felice, V., Zummo, G., and Cappello, F. (2007) *J. Cancer Mol.* 3 (3), 71-79
2. Kirkinezos, I. G, and Moraes, C. T. (2001) *Semin. Cell Dev. Biol.* 12, 449-457
3. Toyokuni, S., Okamoto, K., Yodoi, J., and Hiai, H. (1995) *FEBS Lett.* 358, 1-3
4. Warburg, O. (1956) *Science* 123, 309-314
5. Carew, J. S., and Huang, P. (2002) *Mol. Cancer* 1, 9
6. Zick, M., Rabl, R., and Reichert, A. S. (2009) *Biochim. Biophys. Acta* 1793, 5-19
7. Frezza, C., Cipolat, S., Martins de Brito, O. et al. (2006) *Cell* 126, 177-189
8. Cipolat, S., Rudka, T., Hartmann, D. et al. (2006) *Cell* 126, 163-175
9. Gottlieb, E. (2006) *Cell* 126, 27-29
10. John, G B., Shang, Y., Li, L., Renken, C., Mannella, C. A., Selker, J. M., Rangell, L., Bennett, M. J., and Zha, J. (2005) *Mol. Biol. Cell* 16, 1543-1554

11. Oka, T., Sayano, T., Tamai, S., Yokota, S., Kato, H., Fujii, G, and Mihara, K. (2008) *Mol. Biol. Cell* 19, 2597-2608
12. Velours, J., Dautant, A., Satin, B., Sagot, I., and Brethes, D. (2009) *Int. J. Biochem. Cell Biol.* 41, 1783-1789
13. Park, Y. U., Jeong, J., Lee, H., Mun, J. Y., Kim, J. H., Lee, J. S., Nguyen, M. D., Han, S. S., Suh, P. G, and Park, S. K. (2010) *Proc. Natl. Acad. Sci. U.S.A.* 107, 17785-17790
14. Darshi, M., Mendiola, V. L., Mackey, M. R., Murphy, A. N., Koller, A., Perkins, G A., Ellisman, M. H., and Taylor, S. S. (2011) *J. Biol. Chem.* 286, 2918-2932
15. Rong, R., Jin, W., Zhang, J., Sheikh, M. S., and Huang, Y. (2004) *Oncogene* 23, 8216-8230
16. Powell, M. J., Casimiro, M. C., Cordon-Cardo, C., He, X., Yeow, W. S., Wang, C., McCue, P. A., McBurney, M. W., and Pestell, R. G (2011) *Cancer Res.* 71, 964-975
17. Yang, J., Liu, X., Bhalla, K., Kim, C. N., Ibrado, A. M., Cai, J., Peng, T. I., Jones, D. P., and Wang, X. (1997) *Science* 275, 1129-1132
18. Magalhaes, P. J., Andreu, A. L., and Schon, E. A. (1998) *Mol. Biol. Cell* 9, 2375-2382
19. Murthy, M. S., and Pande, S. V. (1987) *Proc. Natl. Acad. Sci. U.S.A.* 84, 378-382
20. Prasannan, P., and Appling, D. R. (2009) *Arch. Biochem. Biophys.* 481, 86-93
21. Fujiki, Y., Hubbard, A. L., Fowler, S. and Lazarow, P. B. (1982) *J. Cell Biol.* 92, 97-102.
22. Lui, H. M., Chen, J., Wang, L., and Naumovski, L. (2003) *Mol. Cancer. Res.* 1, 508-518
23. Luo, X., He, Q., Huang, Y., and Sheikh, M. S. (2005) *Cell Death Differ* 12, 1310-1318
24. Luo, X., Huang, Y., and Sheikh, M. S. (2003) *Oncogene* 22, 7247-7257
25. Montalbano, J., Jin, W., Sheikh, M. S., and Huang, Y. (2007) *J. Biol. Chem.* 282, 37640-37649
26. He, Q., Shi, J., Jones, S., An, J., Liu, Y., Huang, Y., and Sheikh, M. S. (2009) *Mol. Cell. Pharmacol.* 1, 23-28
27. Corcoran, C. A., Montalbano, J., Sun, H., He, Q., Huang, Y., and Sheikh, M. S. (2009) *J. Biol. Chem.* 284, 21955-21970
28. Moffat, J., Grueneberg, D. A., Yang, X. et al. (2006) *Cell* 124, 1283-1298
29. Ito, S. and Karnovsky, M. J. (1968) *J. Cell Biol.* 39, 168a-169a
30. Vives-Bauza, C., Yang, L., and Manfredi, G. (2007) *Methods Cell Biol.* 80, 155-171
31. Barrientos, A. (2002) *Methods.* 26, 307-316
32. Corcoran, C. A., He, Q., Ponnusamy, S., Ogretmen, B., Huang, Y., and Sheikh, M. S. (2008) *Mol. Cancer. Res.* 6, 795-807
33. Sun, H., Luo, X., Montalbano, J., Jin, W., Shi, J., Sheikh, M. S., and Huang, Y. (2010) *Mol. Cancer. Res.* 8, 57-66
34. Montalbano, J., Lui, K., Sheikh, M. S., and Huang, Y. (2009) *J. Biol. Chem.* 284, 18129-18142
35. Ghosh, J. C., Siegelin, M. D., Dohi, T., and Altieri, D. C. (2010) *Cancer Res.* 70, 8988-8993
36. Goh, Y. C., Yap, C. T., Huang, B. H., Cronshaw, A. D., Leung, B. P., Lai, P. B., Hart, S. P., Dransfield, I., and Ross, J. A. (2011) *Cell Mol. Life Sci.* 68, 1581-1592
37. Merendino, A. M., Bucchieri, F., Campanella, C. et al. (2010) *PLoS One* 5, e9247
38. Shoshan-Barmatz, V., Zalk, R., Gincel, D., and Vardi, N. (2004) *Biochim. Biophys. Acta* 1657, 105-114
39. De Pinto, V., Messina, A., Lane, D. J., and Lawen, A. (2010) *FEBS Lett.* 584, 1793-1799
40. Ozawa, T., Natori, Y., Sako, Y., Kuroiwa, H., Kuroiwa, T., and Umezawa, Y. (2007) *ACS Chem. Biol.* 2, 176-186
41. Gieffers, C., Korioth, F, Heimann, P., Ungermann, C., and Frey, J. (1997) *Exp. Cell Res.* 232, 395-399
42. Odgren, P. R., Toukatly, G, Bangs, P. L., Gilmore, R., and Fey, E. G (1996) *J. Cell. Sci.* 109 (Pt 9), 2253-2264
43. Xie, J., Marusich, M. E, Souda, P., Whitelegge, J., and Capaldi, R. A. (2007) *FEBS Lett.* 581, 3545-3549

6.2 Example 2: CHCM1 Expression at the mRNA Level

CHCM1 (Coiled coil Helix Cristae Morphology 1) is a mitochondrial protein that is also annotated in the GenBank as CHCHD6. This example demonstrates a link between CHCM1 and tumors, particularly malignant melanoma. The results indicate that CHCM1 is down-regulated in response to DNA damage-inducing anticancer drugs and important for the integrity of mitochondrial cristae structures. CHCM1 contains 235 amino acids and 26.5 kDa in size (FIG. 14). The carboxyl-terminal end contains a Coiled coil Helix-Coiled coil Helix (CHCH) domain and the amino-terminal end harbors putative N-myristoylation site (FIG. 14).

Using cancer profiling arrays, we have examined CHCM1 expression at the mRNA level in matched normal and tumor specimens representing 154 patients and 19 different tissue types. The results show that CHCM1 expression is deregulated in some malignancies. For example, 70% (7/10) of skin cancers showed high level of expression of CHCM1. All 7 specimens showing increased expression were malignant melanoma (FIGS. 15 and 16). In addition, 4 out of 7 (57%) informative breast cancer patient samples showed increased expression in tumor tissue than matching normal tissues. In the case of testicular and thyroid gland tumors, 6/10 (60%) of each tumor type showed increased expression by tumor tissues than matching normal tissues.

We also investigated the expression status of CHCM1 at the protein level in matching normal and tumor samples representing breast, colon and lung tissues. We examined 10 pairs of primary matching normal and tumor tissues from breast cancer patients, 30 pairs of matching normal and tumors tissues from colon cancer patients and 2 pairs of normal and tumor tissues from lung cancer patients. The results indicated that CHCM1 protein expression was increased in 30% (3/10) of breast cancer samples, 50% (15/30) colon cancer samples and 100% (2/2) lung cancer samples when compared with their respective matching normal tissue samples. These findings indicate that CHCM1 expression is deregulated in primary human cancers.

The most striking feature of CHCM1 deregulation was found in melanoma. For example, its expression was noted to be highly increased in melanomas compared to other malignancies when analyzed on the same membrane (FIG. 15). FIG. 16 shows that clinicopathological features of melanoma samples (shown in FIG. 15) exhibited higher CHCM1 mRNA levels.

We have also analyzed CHCM1 expression in human normal neonatal epidermal melanocytes (HEMn-MP) and found that in comparison to normal melanocytes, 7/11 (63.6%) melanoma cell lines showed higher protein expression (FIG. 17) further supporting the notion that CHCM1 expression appears to be up-regulated in melanoma.

We have since performed immunohistochemical staining on melanoma and normal skin specimens. The results indicated that CHCM1 expression is increased in the majority of melanoma specimens (FIGS. 18, 19A-D and 20). Melanoma is cancer of the melanocytes. The normal melanocytes predominantly reside in the basal layer of epidermis. We noted that in general, the basal layers of normal skin samples showed weaker staining for CHCM1. Evaluation of normal melanocytes in the epidermal layers showed absent to weaker staining for CHCM1. Thus, the results indicate that CHCM1 expression is increased in the malignant melanoma (FIGS. 18, 19A-D and 20).

Collectively, the results in this example demonstrate that CHCM1 expression is deregulated in human malignancies in a tissue specific manner and therefore, CHCM1 has potential to serve as a tissue specific tumor marker most importantly for melanoma for which newer markers are urgently needed. The results also indicate that CHCM1 is down-regulated in human cancers in response to treatment with DNA toxic anticancer drugs (FIGS. 21-23) and that CHCM1 knockdown in cancer cells leads to growth inhibition (FIG. 24) indicating that CHCM1 also can serve as a target to develop cancer therapeutics.

Cancer is one of the leading causes of deaths worldwide. In the US alone, more than 1 million cases of various types of cancers are diagnosed each year and more than half million people die due to cancer. Accurate and early diagnosis, and treatment of cancer is paramount to improve survival and quality of life. Tumor markers with diagnostic and prognostic significance can help achieve these goals and because tumors exhibit significant tumor heterogeneity, therefore, multiple tumor markers can facilitate accurate and early detection. Also, within a tumor type, one or more tumor markers can serve to sub-classify a subset of tumor and predicts its behavior. Thus, cancer markers that can facilitate accurate cancer diagnosis in general and detection at early stages in particular are urgently needed for all types of cancers. In this context, genes and their protein products differentially expressed between normal and cancer tissues have the potential to serve as important tumor markers. One of the major problems in cancer therapeutics is that the existing cancer drugs affect cancer as well as normal cells. Therefore, better therapeutic approaches are urgently needed to selectively target cancer cells but spare normal cells. In this regard, tumor markers as cancer-specific molecules linked to cancer cell growth and survival can provide very valuable insight into developing newer therapeutic strategies. For example, molecules with anti-tumor potential whose expression is deregulated in cancers can serve as important cancer diagnostic and prognostic markers on the one hand and targets to develop novel cancer therapeutics on the other. These molecules with diagnostic and prognostic potential can also predict patients' response to therapy.

(I) The highly significant findings indicate that CHCM1 expression is increased in malignant melanomas and in some cancers of breast, colon, lung, testis and thyroid. These findings highlight the significance of CHCM1 as a powerful and high-value diagnostic and prognostic tumor marker as well as an anti-tumor target to develop better therapeutic strategies particularly for melanomas and also for other malignancies. For example, assays can be developed to measure CHCM1 expression at the mRNA or protein levels to diagnose melanoma and cancers. These assays can also be used to examine expression at different stages during the course of these malignancies in order to predict tumor behavior and response to cancer therapy. Novel therapeutics can be developed and the existing ones can also be used to (i) block/decrease CHCM1 expression in human tumors and/or (ii) disrupt its interactions with other molecules and thereby inhibit or completely block tumor growth.

(II) The CHCM1-based assays will also have utility for basic biomedical research laboratories engaged in investigating molecular pathogenesis of cancers using cell-based and animal studies.

Exposure to environmental agent such as UV radiation has also been linked to melanoma development. Melanoma is considered to be the highly aggressive malignancy affecting the skin (1 and refs therein). Melanoma arises in melanocytes and can be classified into various types including cutaneous, acral, mucosal and uveal melanomas (1). The cutaneous type is the most common and affects skin and has a predominant association with exposure to UV (1-3). This variety can be further subdivided into chronic sun-damage (CSD) melanoma and non-chronic sun-damage (non-CSD) melanoma (2, 3). The acral type affects skin of palms, soles and the area underneath fingernails or toenails. As the name implies, the mucosal variety occurs in mucosal tissues whereas the uveal type affects melanocytes in other organs for example, in iris of the eye. It is believed that the acral, mucosal and uveal types are not linked to UV exposure (1-3). Although the molecular pathogenesis of malignant melanoma remains to be fully investigated, mutations in BRAF gene that encodes a serine threonine kinase have been found in approximately 45% of the cases (1) of cutaneous (non-CSD) melanoma. In the case of mucosal, uveal and CSD varieties, the incidence of BRAF mutations is reported to be lower. Point mutations in NRAS have also been reported for non-CSD melanoma, while aberrations in KIT receptor tyrosine kinase have been found in CSD, mucosal and acral types of melanomas (1). It is of note that not all melanomas harbor mutations in BRAF or NRAS or aberrations in KIT receptor-mediated signaling (4, 5). Therefore, further studies are needed to identify additional molecules that are linked to melanoma development and/or progression. Such molecules are expected to prove very valuable for better understanding of melanoma pathogenesis and can also serve as (i) markers for improved diagnosis and prognosis and (ii) targets to develop novel therapeutics. CHCM1 is one such molecule.

Novel approaches to manage melanoma are urgently needed. Dacarbazine (DTIC) is a commonly used anticancer drug for advanced malignant melanoma but response rate remains low and tumors initially responding to drug eventually acquire resistance to DTIC (6, 7). Cisplatin is another anticancer drug and its use in combination with other therapeutics is being explored as an alternative strategy to manage melanoma (8). The results in this example indicate that CHCM1 expression is down-regulated by DTIC and cisplatin in melanoma cell lines (FIGS. 5 and 6). It is therefore, possible that DTIC and cisplatin-mediated inhibition of CHCM1 is one of the key events in sensitizing melanoma cells to these drugs in the clinical setting and that lack of CHCM1 inhibition may make melanoma cells resistant against these drugs in the clinic. More recently, FDA has approved vemurafenib (PLX4032) for the treatment of malignant melanoma that harbor BRAF mutation (BRAF$^{V600E}$ is the most common oncogenic mutation that activates this kinase and about 45-50% of melanoma harbor such mutation) (9, 10). Vemurafenib does not work in melanomas that harbor wild type BRAF. Another limitation of vemurafenib is that some melanomas although harbor BRAF mutation do not respond to vemurafenib (inherent resistance) while others initially respond but later acquire resistance (9, 11, 12). The molecular basis for acquisition to vemurafenib resistance is believed to be multifactorial in nature and remains to be fully investigated (12). It is possible that deregulation of CHCM1 may be one of the contributing factors for the inherent or acquired resistance to vemurafenib. The preliminary results indicate that CHCM1 knockdown (genetic inhibition) affects growth of melanoma cell lines that harbor mutant BRAF (vemurafenib-sensitive A375 and UACC-62) or wild type BRAF (vemurafenib-nonresponsive Sk-Mel-103) (FIGS. 8A-B). Targeting of CHCM1 may be used to (i) further improve the therapeutic potential of vemurafenib in vemurafenib-sensitive BRAF-mutant melanoma cells, and (ii) manage melanomas for which vemurafenib cannot be used (i.e. BRAF wild type tumors) or for those that harbor BRAF mutation but have inherent or acquired resistance to vemurafenib.

CHCM1 can be detected by analyzing specimens by immunohistochemical staining, Western blotting, Immunoprecipitation, protein pull-down, Northern or Dot blotting, microarray or any modification of these procedures. It is possible that that CHCM1 may be detected in the circulation in cancer patients and the blood samples could be used as materials for its detection for diagnosis/prognosis and response to therapy. CHCM1 is an intracellular protein and there is evidence in the literature that some intracellular proteins can be detected in circulation (blood sample) as tumor biomarker. For example, DJ-1/PARK7 is an intracellular protein that was detected at an increased levels in circulation of breast cancer patients compared to group who did not have breast cancer (Clin Cancer Res November 2001 7; 3328 also mentioned at this url: http://www.mblint1.com/product/CY-9050). Similarly, SMAC is an intracellular protein but has been reported to be found in serum and the potential of circulating Smac was investigated in bladder cancer patients (Int J Oncol. 2012 April; 40(4):1246-50).

Melanoma is a complex disease and accurate diagnosis is of paramount importance. Newer markers that help facilitate accurate diagnosis and diagnosis of difficult cases are highly desirable. CHCM1 would serve as a powerful, high-value marker of melanoma diagnosis. Furthermore, CHCM1 expression can be determined at different stages of the disease to predict tumor behavior and response to cancer therapy. Also, better therapeutic options are needed for melanoma and CHCM1 can serve as a molecular target to develop therapeutics. For example, novel therapeutics (including for example, small molecules) can be developed and the existing ones can also be utilized for a new use to (i) block/decrease CHCM1 expression in human tumors and/or (ii) disrupt its interactions with other molecules and thereby inhibit or completely block tumor growth.

Tests for CHCM1 expression levels would provide information that no current test for melanoma provides. A panel of makers such as 5100, HMB-45, Melan-A, Mart-1 and tyrosinase are used for melanoma diagnosis in the clinic. However, it is not uncommon for melanomas to be negative for some of the available markers. To avoid misdiagnosis, additional markers that help clinch the diagnosis are always desirable. The results indicate that CHCM1 is overexpressed in cutaneous (skin) and non-cutaneous malignant melanomas (FIGS. 19A-D) and has potential to be an additional high value marker for melanoma diagnosis. In particular, also note that all mucosal melanoma samples in the results (FIGS. 19A-D) were positive for CHCM1 expression and the majority of them showed higher CHCM1 expression with staining intensity in the 2+ and 3+ ranges. Mucosal melanomas are believed to exhibit more aggressive behavior and have higher mortality compared to cutaneous melanomas (Seetharamu N. et al., The Oncologist July 2010 vol. 15 no. 7 772-781). Diagnosis of mucosal melanoma is difficult and generally delayed (Seetharamu N. et al., The Oncologist July 2010 vol. 15 no. 7 772-781). Mucosal melanomas also frequently show micrometastases. The findings that higher number of mucosal melanomas show increased positivity for CHCM1 highlight the point that CHCM1 can also be used for diagnosis of such melanomas including the associated micrometastases.

Use of a CHCM1 assay will help avoid misdiagnosis and facilitate accurate diagnosis of difficult to diagnose cases, and will lead to more timely initiation of intervention/treatment.

Assays for CHCM1 can be of various types appropriate for detecting the expression level of a gene or its protein product. One type of assay is to analyze biopsy specimens by immunohistochemical staining using an anti-CHCM1 antibody or any other substance that will bind to CHCM1 and can be detected optically, electrically, magnetically, chemically, physically, or by some other means. One method is Western blotting, which can also be used. Another method is Northern blotting. There are other methods to detect CHCM1 as noted above.

Vemurafenib has been approved by the US FDA as the most recent option for the treatment of malignant melanoma that harbors a BRAF mutation. Vemurafenib does not work in melanomas that harbor wild type BRAF. Another limitation of vemurafenib is that some melanomas that harbor a BRAF mutation do not respond to vemurafenib (inherent resistance) while others initially respond but later acquire resistance. It is possible that deregulation of CHCM1 may be one of the contributing factors for the inherent or acquired resistance to vemurafenib. The results indicate that CHCM1 knockdown by RNA interference approach (genetic inhibition) affects growth of melanoma cell lines that harbor mutant BRAF (vemurafenib-sensitive A375 and UACC-62) or wild type BRAF (vemurafenib-nonresponsive Sk-Mel-103) (FIGS. 8A-B). Therefore, targeting of CHCM1 can be used to (i) further improve the therapeutic potential of vemurafenib in vemurafenib-sensitive BRAF-mutant melanoma cells, and (ii) manage melanomas for which vemurafenib cannot be used (i.e. BRAF wild type tumors) or for those that harbor BRAF mutation but have inherent or acquired resistance to vemurafenib. Clearly, targeting CHCM1 will lead to better therapeutic management of malignant melanoma.

As FIGS. 6A-B of Example 1 show, the efficacy of cancer therapeutics, including genotoxic anticancer drugs, can be enhanced by decreasing CHCM1 levels while administering the cancer therapeutic, such as by co-administering a compound that reduces the expression of CHCM1 or blocking the functioning of CHCM1 proteins that have been expressed. The present invention includes a method of treating a cancer comprising the steps of (a) administering a therapeutic compound that are used for treatment/management of the cancer and (b) administering a compound that reduces the expression of CHCM1 or blocks or inhibits the functioning of CHCM1 proteins. The cancer may be breast cancer, melanoma or another form of cancer.

The therapeutic compound may be an anticancer drug including, but not limited to, doxorubicin (ADRIAMYCIN®), etoposide, bendamustine, busulfan, carmustine, chlorambucil, cyclophosphamid, dacarbazine (dtic), ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D/dactinomycin, bleomycin, daunorubicin, epirubicin, idarubicin, mitomycin, mitoxantrone, docetaxel, irinotecan, paclitaxel, topotecan, vinblastine, vincristine, vinorelbine, carboplatin, cisplatin and oxaliplatin or any anti-cancer or anti-tumor drug known in the art.

The compound reducing the expression of CHCM1 or blocking its activity or its interactions with other proteins can be a shRNA, siRNA, peptide, small molecule (including Cisplatin and DTIC), an antibody, or a large molecule. The method of treating a cancer can include a first step of determining the level of CHCM1 expression in the cancer cells and if CHCM1 is being overexpressed, then proceeding with steps (a) and (b).

The present invention also includes a method of treating a cancer comprising down-regulating or blocking the activity of CHCM1 or blocking CHCM1 interactions with other proteins. Reducing the expression or blocking the activity of CHCM1 or blocking CHCM1 interactions with other proteins can comprise administering a compound that down-regulates CHCM1 or interferes with the functioning of CHCM1 or with CHCM1 interactions with other proteins. The compound can be any of the compounds described herein as modulating the expression of CHCM1, and any of the known types of compounds that will interfere with the expression or activity of a protein that has been modified to reduce the expression of CHCM1 or bind to it to reduce its activity or functionality. The compound can be any new compound that can be identified in the future using the information from the structure of CHCM1.

The present invention also includes an assay for a cancer that comprises determining the level of CHCM1. Determining the level of CHCM1 can include the steps of obtaining a sample of the cancer (such as by biopsying a tumor) and applying an immunohistochemical staining procedure to the sample, wherein the immunohistochemical staining procedure will detect CHCM1 expression. A last step can include evaluating the stained sample to determine the level of CHCM1. Determining the level of CHCM1 can also include the steps of obtaining a blood sample from the patient having the cancer and detecting the level of CHCM1 in the blood sample. Determining the level of CHCM1 can include the steps of obtaining a blood sample from the patient having the cancer and detecting the level of the mRNA for CHCM1 in the blood sample, such as by using RT-PCR or a microarray. The assay can be an assay to determine whether a cancer is melanoma. It can also be an assay for other types of cancers mentioned herein.

The present invention also includes an assay to determine the whether a therapeutic compound modulates the expression of CHCM1 by following the same steps as described above. The present invention also includes an assay to determine whether a therapeutic compound is reducing the expression or activity of CHCM1 or its interactions with other proteins.

The present invention relates to the use of inhibitors of CHCM1 to treat cancer, in particular to treat melanoma. A CHCM1 inhibitor is any agent that would reduce the levels of CHCM1 and/or interfere with CHCM1 activity/function and/or block/interfere with CHCM1 interactions with other proteins. The present invention also relates to the use of CHCM1 inhibitors to improve the efficacy of other cancer therapeutics by co-administering a CHCM1 inhibitor with another cancer therapeutic. The present invention also relates to an assay for cancer that determines the level of CHCM1 expression, and to an assay where the cancer is melanoma.

According to various embodiments, the substance suitable for the instant invention can be a nucleic acid, such as a genetic construct or other genetic means directing expression of an antagonist of CHCM1 function. Nucleic acid molecules suitable for the inventive method include anti-sense polynucleotides, other polynucleotides that bind to CHCM1 mRNA, recombinant retroviral vector, or a combination thereof. A preferred genetic construct of the invention comprises a gene delivery vehicle, a recombinant retroviral vector, or a combination thereof. In a preferred embodiment, the substance that inhibits CHCM1 function is a nucleic acid that hybridizes to a CHCM1 mRNA.

In other embodiments, the substances suitable for the instant invention may also include peptidomimetic inhibitors of CHCM1 function, ribozymes, and an RNA aptamer, or a combination thereof.

Pharmaceutical agents or genetic therapies that reduce or eliminate CHCM1 activity and function encompass, but are not limited to the following: 1) small molecule inhibitors (preferably having a molecular weight of less than 10,000) of CHCM1 activity (i.e. suicide substrates; competitive or non-competitive inhibitors of CHCM1 activity; RNA aptamers), 2) anti-sense oligonucleotides, 3) peptidomimetics, 4) ribozymes, 5) means for interfering with transcription and/or translation of CHCM1 RNA, or 6) genetic therapy comprising transfection with a dominant negative CHCM1 mutant or 7) use of any of these approaches to block/interfere with CHCM1 interactions with other proteins.

Means for inhibiting CHCM1 function comprise genetic and non-genetic means for inhibiting CHCM1 function, and includes substances that inhibit CHCM1 functions, levels or interactions with other proteins.

Among the genetic construct inhibiting CHCM1 function are various "gene delivery vehicles" known to those of skill in the art, that facilitate delivery to a cell of, for example, a coding sequence for expression of a polypeptide, such as a CHCM1 inhibitor, an anti-sense oligonucleotide, an RNA aptamer capable of inhibiting CHCM1 activity, an RNA aptamer capable of inhibiting a ribozyme, or another genetic construct of inhibiting CHCM1 activity known to those of skill in the art.

Among the non-genetic means inhibiting CHCM1 function are pharmaceutical agent, pharmaceutically acceptable salts thereof that are preferably administered in a pharmaceutically acceptable carrier.

According to preferred embodiments, substances suitable for the instant invention can be a nucleic acid, such as a genetic construct or other genetic means directing expression of an antagonist of CHCM1 function. Nucleic acid molecules suitable for the inventive method include anti-sense polynucleotides, other polynucleotides that bind to CHCM1 mRNA, recombinant retroviral vector, or a combination thereof. A preferred genetic construct of the invention comprises a gene delivery vehicle, a recombinant retroviral vector, or a combination thereof. In a preferred embodiment, the substance that inhibits CHCM1 function is a nucleic acid that hybridizes to a CHCM1 mRNA.

Preferred substances may also include peptidomimetic inhibitors of CHCM1 function, ribozymes, and an RNA aptamer, or a combination thereof.

Suitable substances for the instant invention may also be a low molecular weight substance having a molecular weight of less than about 10,000 that inhibits CHCM1 activity.

Administering a therapeutic compound refers to the process of delivering to a mammal a therapeutic agent, or a combination of therapeutic agents. The process of administration can be varied, depending on the therapeutic agent, or agents, and the desired effect. Administration can be accomplished by any means appropriate for the therapeutic agent, for example, by parenteral, mucosal, pulmonary, topical, catheter-based, or oral means of delivery. Parenteral delivery can include, for example, subcutaneous, intravenous, intramuscular, intra-arterial, and injection into the tissue of an organ. Mucosal delivery can include, for example, intranasal delivery. Pulmonary delivery can include inhalation of the agent. Catheter-based delivery can include delivery by iontophoretic catheter-based delivery. Oral delivery can include delivery of an enteric coated pill, or administration of a liquid by mouth. Administration will generally also include delivery with a pharmaceutically acceptable carrier, such as, for example, a buffer, a polypeptide, a peptide, a polysaccharide conjugate, a liposome and/or a lipid. Gene therapy protocol is considered an administration in which the therapeutic agent is a polynucleotide capable of accomplishing a therapeutic goal when expressed as a transcript or a polypeptide in the mammal.

The administration of a compound and variants thereof (e.g., "administering" a compound) used in reference to a compound of the invention can also mean introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In treating a cancer, a therapeutically effective amount a CHCM1 inhibitor is administered. A therapeutically effective amount is that amount that will generate the desired therapeutic outcome. A therapeutically effective amount can be an amount administered in a dosage protocol that includes days or weeks of administration. It is also that amount of active compound or pharmaceutical agent that elicits the biological or medicinal response in a tissue, system, animal or human that is being sought by a researcher, veterinarian, medical doctor or other clinician.

The term "pharmaceutically acceptable carrier" refers to a carrier for administration of a therapeutic agent, such as, for example, a polypeptide, polynucleotide, small molecule (preferably a molecule having a molecular weight of less than about 10,000), peptoid, or peptide, refers to any pharmaceutically acceptable carrier that does not itself induce the production of antibodies harmful to the individual receiving the composition, and which may be administered without undue toxicity. It can also refer to a carrier, such as a solvent, suspending agent or vehicle, for delivering the compound or compounds in question to the animal or human. The carrier may be liquid or solid and is selected with the planned manner of administration in mind Liposomes are also a pharmaceutical carrier. As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated.

A pharmaceutically acceptable component is one that is suitable for use with humans and/or animals without undue adverse side effects (such as toxicity, irritation, and allergic response) commensurate with a reasonable benefit/risk ratio.

"Mammalian cell" as used herein refers to a subset of eukaryotic cells useful in the invention as host cells, and includes human cells, and animal cells such as those from dogs, cats, cattle, horses, rabbits, mice, goats, pigs, etc. The cells used can be genetically unaltered or can be genetically altered, for example, by transformation with appropriate expression vectors, marker genes, and the like.

The term "antagonist" as used herein refers to a molecule that blocks signaling, such as for example a molecule that can bind a receptor, but which does not cause a signal to be transduced by the receptor to the cell. In general, an antagonist of a polypeptide is an inhibitor of any biological activity of the polypeptide. A given inhibitor or agonist may target and inhibit one biological activity, while not affecting another non-target activity of the molecule.

As used herein, in other embodiments, suitable CHCM1 inhibitors for use in the methods of the present invention can include, without limitation, small hairpin RNAs (shRNAs) small interfering RNAs (siRNAs) or microRNAs (miRNAs) that are effective to inhibit CHCM1 via RNA interference (RNAi) (post transcriptional gene silencing).

RNAi technology provides an efficient means for blocking expression of a specific gene. RNAi technology takes advantage of the cell's natural machinery, facilitated by short interfering RNA molecules, to effectively knock down expression of a gene of interest. There are several ways to induce RNAi, synthetic molecules, shRNA, siRNA, miRNA, RNAi vectors, and in vitro dicing.

RNAi can be used to inhibit the CHCM1 genes, such as by creating shRNAs, siRNAs or miRNAs having the appropriate sequence and delivering them to the cells in which inhibition of the CHCM1 gene is desired. A key area of research in the use of RNAi for clinical applications is the development of a safe delivery method, which to date has involved mainly viral vector systems similar to those suggested for gene therapy. Once developed, these delivery methods can be used for the purposes of the present invention. RNAi inducing agents can also be delivered using bacteria, retroviruses, DNA viruses, lipidoids and amphoteric liposomes and nanoparticle-based approaches.

General rules for selecting siRNA targets on mRNA sequences include, for example, the following (www.rnai-web.com/RNAi/siRNA_Design/): (i) Targets should be located 50-100 nt downstream of the start codon (ATG); (ii) Search for sequence motif $AA(N_{19})TT$ or $NA(N_{21})$, or $NAR(N_{17})YNN$, where N is any nucleotide, R is purine (A, G) and Y is pyrimidine (C, U); (iii) Target sequences should have a G+C content between 35-60%; (iv) Avoid stretches of 4 or more nucleotide repeats; (v) Avoid 5'URT and 3'UTR, although siRNAs targeting UTRs have been shown to successfully induce gene silencing; and (vi) Avoid sequences that share a certain degree of homology with other related or unrelated genes.

Similarities and differences between siRNA and shRNA are known in the art (e.g., Rao D D, Vorhies J S, Senzer N, Nemunaitis J. siRNA vs. shRNA: similarities and differences. Adv Drug Deliv Rev. 2009 Jul. 25; 61(9):746-59).

Designing shRNA targets is also well known in the art (e.g., Chris B. Moore, Elizabeth H. Guthrie, Max Tze-Han Huang, and Debra J. Taxman. Short Hairpin RNA (shRNA): Design, Delivery, and Assessment of Gene Knockdown. Methods Mol Biol. 2010; 629:141-158.)

Selecting targets for miRNA: In animals, the tendency of miRNAs to bind their mRNA targets with imperfect sequence homology poses considerable challenges with target prediction. In animals, target sites are often only partially complementary to their miRNAs and are mostly located in the 3'UTR of target genes. Several computational approaches have been developed to facilitate experimental design and predicting miRNA targets. In general, computational target prediction identifies potential binding sites according to base-pairing rules and cross species conservation conditions.

The dosage form of the CHCM1 inhibitor of the present invention may be a liquid solution ready for use or intended for dilution with a preservation solution. Alternatively, the dosage form may be lyophilized or power filled prior to reconstitution with a preservation solution. The lyophilized substance may contain, if suitable, conventional excipients.

Other than in the operating examples, or unless otherwise expressly specified, all of the numerical ranges, amounts, values and percentages such as those for amounts of materials, times and temperatures of reaction, ratios of amounts, values for molecular weight (whether number average molecular weight ("$M_n$") or weight average molecular weight ("$M_w$"), and others in the following portion of the specification may be read as if prefaced by the word "about" even though the term "about" may not expressly appear with the value, amount or range. Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements. Furthermore, when numerical ranges of varying scope are set forth herein, it is contemplated that any combination of these values inclusive of the recited values may be used.

As used herein, the term "composition" is intended to encompass a product comprising the specified ingredients in the specified amounts, as well as any product that results, directly or indirectly, from combination of the specified ingredients in the specified amounts.

A person of ordinary skill in the art can easily determine an appropriate dose of one of the instant compositions to administer to a subject without undue experimentation. Typically, a physician will determine the actual dosage that will be most suitable for an individual patient and it will depend on a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy. The dosages disclosed herein are exemplary of the average case. There can of course be individual instances where higher or lower dosage ranges are merited, and such are within the scope of this invention.

Unless defined otherwise, all technical and scientific terms used herein have the same meaning as commonly understood by one of ordinary skill in the art (e.g., in cell culture, molecular genetics, nucleic acid chemistry, hybridization techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4th Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calit), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.).

REFERENCES FOR EXAMPLE 2

1. Curtin J A, Fridlyand J, Kageshita T, et al. Distinct sets of genetic alterations in melanoma. N Engl J Med 2005; 353(20):2135-47.
2. Takata M, Murata H, Saida T. Molecular pathogenesis of malignant melanoma: A different perspective from the studies of melanocytic nevus and acral melanoma. Pigment Cell Melanoma Res 2010; 23(1):64-71.
3. Moan J, Cicarma E, Setlow R et al. Time trends and latitude dependence of uveal and cutaneous malignant melanoma induced by solar radiation. Dermatoendocrinol 2010; 2(1):3-8.
4. Yun J, Lee J, Jang J, et al. KIT amplification and gene mutations in acral/mucosal melanoma in korea. APMIS 2011; 119(6):330-5.
5. Kong Y, Si L, Zhu Y, et al. Large-scale analysis of KIT aberrations in chinese patients with melanoma. Clin Cancer Res 2011; 17(7):1684-91.
6. Singh S, Davis R, Alamanda V, et al. Rb-Raf-1 interaction disruptor RRD-251 induces apoptosis in metastatic melanoma cells and synergizes with dacarbazine. Mol Cancer Ther. 2010; 9(12):3330-41.
7. Eggermont A M, Kirkwood J M. Re-evaluating the role of dacarbazine in metastatic melanoma: what have we learned in 30 years? Eur J Cancer 2004; 40:1825-36.
8. Daponte A, Ascierto P A, Gravina A, et al. Temozolomide and cisplatin in avdanced malignant melanoma. Anticancer Res. 2005; 25(2B):1441-7.
9. Baudy A R, Dogan T, Flores-Mercado J E, et al. FDG-PET is a good biomarker of both early response and acquired resistance in BRAFV600 mutant melanomas treated with vemurafenib and the MEK inhibitor GDC-0973. EJNMMI Res 2012; 2(1):22.
10. Yang H, Higgins B, Kolinsky K, et al. RG7204 (PLX4032), a selective BRAFV600E inhibitor, displays potent antitumor activity in preclinical melanoma models. Cancer Res 2010; 70(13):5518-27.
11. Neyns B, Seghers A C, Wilgenhof S, Lebbe C. Successful rechallenge in two patients with BRAF-V600-mutant melanoma who experienced previous progression during treatment with a selective BRAF inhibitor. Melanoma Res 2012 May 11. [Epub ahead of print]
12. Kudchadkar R, Paraiso K H, Smalley K S. Targeting mutant BRAF in melanoma: current status and future development of combination therapy strategies. Cancer J 2012; 18(2):124-31.

Samples of Methods that are Described Herein are as Follows:

A method for diagnosing and treating a cancer or a tumor in a patient comprising the steps of:
obtaining a biological sample from a patient,
analyzing the sample for the presence or absence of Coiled Coil Helix Cristae Morphology 1 protein (CHCM1), wherein the patient is diagnosed with the cancer or the tumor if the sample expresses higher levels of CHCM1 compared to normal tissue; and administering a cancer (or tumor) treatment to the diagnosed patient (i.e., provided that the patient is diagnosed with the cancer or the tumor).

In one embodiment of the method, the cancer or tumor is breast cancer, colon cancer or melanoma.

In another embodiment of the method, the biological sample can be a cell or tissue sample such as a sample from a biopsy (e.g., obtained from a patient's suspected cancer or tumor) or a blood sample.

In another embodiment of the method, the step of analyzing the sample for the presence or absence of CHCM1 comprises the step of determining whether CHCM1 is overexpressed, and then administering a cancer (or tumor) treatment to the diagnosed patient provided that CHCM1 is overexpressed.

In another embodiment of the method, the step of analyzing the sample for the presence or absence of CHCM1 comprises the step of performing Western blotting, Northern blotting, dot blotting or PCR-based approaches.

In certain embodiments of the method, overexpression of CHCM1 is 1.5- to 2-fold, 2- to 3-fold, 3- to 5-fold, 5- to 10-fold, or greater than 10-fold greater than normal or wild-type expression of CHCM1.

In another embodiment of the method, quantitatively higher levels of CHCM1 are 1.5 fold and higher compared to corresponding normal tissue. Determination of normal or wild-type expression of CHCM1 can be performed by the skilled artisan using routine methods. Expression may be measured by band intensity (e.g., in a Northern or Western blot), by other measures of expression, or by the intensity of histochemical or immunohistochemical staining.

In another embodiment of the method, the step of administering the cancer treatment to the diagnosed patient comprises the step of administering a therapeutic compound for treating and/or managing the cancer to the patient.

In another embodiment of the method, the therapeutic compound is an anticancer drug including, but not limited to, doxorubicin (ADRIAMYCIN®), etoposide, bendamustine, busulfan, carmustine, chlorambucil, cyclophosphamid, dacarbazine (dtic), ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D/dactinomycin, bleomycin, daunorubicin, epirubicin, idarubicin, mitomycin, mitoxantrone, docetaxel, irinotecan, paclitaxel, topotecan, vinblastine, vincristine, vinorelbine, carboplatin, cisplatin and oxaliplatin.

In another embodiment of the method, the step of administering the cancer treatment to the diagnosed patient comprises the step of administering a compound for reducing the expression of CHCM1 or for blocking or inhibiting function of CHCM1.

In another embodiment of the method, the step of administering the cancer treatment to the diagnosed patient comprises the step of administering a compound for reducing the expression of CHCM1 or for blocking or inhibiting function of CHCM1.

In another embodiment of the method, the compound reducing the expression of CHCM1 or blocking or inhibiting its activity or its interactions with other proteins is a shRNA, siRNA, a peptide, a small molecule (e.g., Cisplatin and DTIC), an antibody, or a large molecule such as a full-length protein or a larger fragment of a protein. Smaller fragments (polypeptides) of CHCM1 can also be used to block its interactions with other proteins. For example, small or large CHCM1 mimetics (peptides) can be used which will interact with CHCM1-interacting proteins and thereby inhibit their interactions with CHCM1 (competitive approach).

In another embodiment of the method, the step of administering the cancer treatment to the diagnosed patient comprises the step of down-regulating, inhibiting or blocking the activity of CHCM1, or inhibiting or blocking CHCM1 interactions with other proteins.

In another embodiment of the method, the step of down-regulating, inhibiting or blocking the activity of CHCM1, or inhibiting or blocking CHCM1 interactions with other proteins comprises administering a compound that: down-regulates or inhibits CHCM1, or interferes with or inhibits the functioning of CHCM1 or with CHCM1 interactions with other proteins.

In another embodiment of the method, the compound is a CHCM1 inhibitor. A CHCM1 inhibitor may be any agent that reduces levels of CHCM1 and/or interferes with CHCM1 activity and/or function and/or blocks and/or interferes with CHCM1 interactions with other proteins.

In another embodiment of the method, the step of analyzing the sample comprises the step of performing an assay, wherein the assay comprises the step of determining the level of CHCM1 in the sample.

In another embodiment of the method, the step of determining the level of CHCM1 comprises the step of performing an immunohistochemical staining procedure on the sample, thereby producing a stained sample, wherein the immunohistochemical staining procedure detects CHCM1 expression.

In another embodiment of the method, the method comprises, after the step of performing the immunohistochemical staining procedure, the step of evaluating the stained sample to determine the level of CHCM1.

In another embodiment of the method, the sample is a blood sample, and the step of determining the level of CHCM1 comprises the step of detecting the level of CHCM1 in the blood sample.

In another embodiment of the method, the step of determining the level of CHCM1 comprises the step of detecting the level of mRNA for CHCM1 in the sample A method for diagnosing and treating a cancer or a tumor in a patient comprising the steps of:

obtaining a sample of cancer or tumor cells from the patient, determining a level of CHCM1 expression in the sample of cancer or tumor cells, and administering to the patient a compound for reducing the expression of CHCM1 or for blocking or inhibiting function of CHCM1.

In one embodiment, the method comprises the step of administering to the patient a therapeutic compound for treating and/or managing the cancer or tumor.

In another embodiment of the method, the therapeutic compound is an anticancer drug including, but not limited to, doxorubicin (ADRIAMYCIN®), etoposide, bendamustine, busulfan, carmustine, chlorambucil, cyclophosphamid, dacarbazine (dtic), ifosfamide, melphalan, procarbazine, streptozocin, temozolomide, asparaginase, capecitabine, cytarabine, 5-fluoro uracil, fludarabine, gemcitabine, methotrexate, pemetrexed, raltitrexed, actinomycin D/dactinomycin, bleomycin, daunorubicin, epirubicin, idarubicin, mitomycin, mitoxantrone, docetaxel, irinotecan, paclitaxel, topotecan, vinblastine, vincristine, vinorelbine, carboplatin, cisplatin and oxaliplatin, and combinations thereof.

In another embodiment of the method, the therapeutic compound is a CHCM1 inhibitor. A CHCM1 inhibitor may be any agent that reduces levels of CHCM1 and/or interferes with CHCM1 activity and/or function and/or blocks and/or interferes with CHCM1 interactions with other proteins.

In one embodiment, the compound that reduces the expression of CHCM1 or that blocks or inhibits function of CHCM1 is a shRNA, siRNA, a peptide, a small molecule (e.g., Cisplatin and DTIC), an antibody, or a large molecule such as such as a full-length protein or a larger fragment of a protein.

A method for diagnosing and treating a cancer or a tumor in a patient comprising the steps of:
  obtaining a biological sample from a patient (e.g., a cancer patient);
  testing the sample for presence of a BRAF mutation; and
  provided that the sample tests positive for presence of a BRAF mutation, administering to the patient vemurafenib.

In one embodiment of the method, the BRAF mutation is V600E.

In another embodiment of the method, the method further comprises the steps of: determining a response of the patient to the administered vemurafenib; and, provided that there is a diminished or no response to the administered vemurafenib, administering to the patient a compound for reducing the expression of CHCM1 or for blocking or inhibiting function of CHCM1.

In another embodiment of the method, the diminished response to administered vemurafenib is diminished 10-20%, 20-30%, 30-40%, 40-50%, 50-60%, 60-70%, 70-80%, 80-90% or 90-100% with respect to an established (known in the art or typical) positive response to administered vemurafenib.

In another embodiment of the method, the step of testing the sample for presence of a BRAF mutation comprises determining the nucleotide sequence of the BRAF gene or a fragment thereof from the patient, comparing the determined nucleotide sequence from the patient with wild-type sequence(s) known in the art for the BRAF gene.

A method for diagnosing and treating a cancer or a tumor in a patient is provided comprising the steps of:
  obtaining a biological sample from a cancer patient showing resistance to vemurafenib,
  analyzing the sample for CHCM1 overexpression;
  administering to the patient vemurafenib; and
  administering to the patient a compound for reducing the expression of CHCM1 or for blocking or inhibiting function of CHCM1.

In one embodiment of the method, the compound that reduces the expression of CHCM1 or that blocks or inhibits function of CHCM1 is a shRNA, siRNA, a peptide, a small molecule (e.g., Cisplatin and DTIC), an antibody, or a large molecule such as such as a full-length protein or a larger fragment of a protein.

A method for diagnosing and treating a cancer or a tumor in a patient comprising the steps of:
  obtaining a biological sample from a patient:
  testing the sample for presence of a BRAF mutation;
  provided that the sample tests negative for presence of a BRAF mutation or tests wild-type for BRAF;
  administering to the patient a compound for reducing the expression of CHCM1 or for blocking or inhibiting function of CHCM1.

In one embodiment of the method, the compound that reduces the expression of CHCM1 or that blocks or inhibits function of CHCM1 is a shRNA, siRNA, a peptide, a small molecule (e.g., Cisplatin and DTIC), an antibody, or a large molecule such as such as a full-length protein or a larger fragment of a protein.

A method for diagnosing a cancer or a tumor in a patient comprising the steps of:
  obtaining a biological sample from a patient,
  analyzing the sample for the presence or absence of cancer cells or tumor cells by measuring the presence or absence of CHCM1,
  wherein the patient is diagnosed with the cancer or the tumor if a CHCM1-specific staining cell is detected in the sample.

A method for treating a cancer or a tumor in a patient comprising:
  requesting a test of the patient, wherein the test provides the results of an analysis to determine whether the patient expresses CHCM1; and
  administering a cancer treatment or a tumor treatment to the patient if the patient expresses CHCM1.

A method for diagnosing cancer or a tumor in a patient, wherein the cancer is characterized by the presence of CHCM1 biomarker comprising the steps of:
  i) obtaining a biological sample from a patient;
  ii) applying an antibody specific for CHCM1 biomarker to the sample, wherein presence of the CHCM1 biomarker creates an antibody-CHCM1 biomarker complex;
  iii) applying a detection agent that detects the antibody-CHCM1 biomarker complex; and
  iv) diagnosing cancer or tumor in the patient provided that the detection agent of step iii) is detected.

In one embodiment, the antibody may be a polyclonal or a preferably, a monoclonal antibody specific for CHCM1. Methods for preparing polyclonal and monoclonal antibodies are well known in the art.

A kit for performing a CHCM1 assay comprising a substance that binds to a CHCM1 protein or nucleic acid.

In one embodiment of the kit, the kit comprises an anti-CHCM1 antibody.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

While embodiments of the present disclosure have been particularly shown and described with reference to certain examples and features, it will be understood by one skilled in the art that various changes in detail may be effected therein without departing from the spirit and scope of the present disclosure as defined by claims that can be supported by the written description and drawings. Further, where exemplary embodiments are described with reference to a certain number of elements it will be understood that the exemplary embodiments can be practiced utilizing either less than or more than the certain number of elements.

All references cited herein are incorporated herein by reference in their entirety and for all purposes to the same extent as if each individual publication, patent or patent application was specifically and individually indicated to be incorporated by reference in its entirety for all purposes.

The citation of any publication is for its disclosure prior to the filing date and should not be construed as an admission that the present invention is not entitled to antedate such publication by virtue of prior invention.

What is claimed is:

1. A method for diagnosing and treating a cancer or a tumor in a patient, wherein the cancer or the tumor overexpresses Coiled Coil Helix Cristae Morphology 1 (CHCM1), the method comprising:
   obtaining a biological sample from a patient,
   determining a level of CHCM1 protein or CHCM1 nucleic acid in the sample, wherein the patient is diagnosed with the cancer or the tumor provided that the biological sample expresses at least a 1.5-fold higher level of CHCM1 protein or CHCM1 nucleic acid than a corresponding level of CHCM1 protein or CHCM1 nucleic acid in matching normal tissue; and
   administering a therapeutic compound to the diagnosed patient,
   wherein:
   the therapeutic compound is a genotoxic anti-cancer compound,
   the cancer is breast cancer, colon cancer, melanoma, lung cancer, testicular cancer, or thyroid cancer,
   the tumor is a breast tumor, colon tumor, melanoma tumor, lung tumor, testicular tumor, or thyroid tumor, and
   the genotoxic anti-cancer compound reduces the expression of CHCM1, blocks or inhibits function of CHCM1, or blocks or inhibits CHCM1 interactions with other proteins.

2. The method of claim 1, comprising: administering a second therapeutic compound, wherein the second therapeutic compound is an anti-cancer compound and is selected from the group consisting of doxorubicin (ADRIAMYCIN®), etoposide, bendamustine, carmustine, chlorambucil, cyclophosphamid, dacarbazine (dtic), ifosfamide, melphalan, temozolomide, asparaginase, capecitabine, cytarabine, 5-fluoro uracil, gemcitabine, methotrexate, pemetrexed, raltitrexed, actinomycin D/dactinomycin, bleomycin, epirubicin, idarubicin, mitomycin, mitoxantrone, docetaxel, irinotecan, paclitaxel, topotecan, vemurafenib, vinblastine, vincristine, vinorelbine, carboplatin, cisplatin and oxaliplatin, or a combination thereof.

3. The method of claim 1, wherein determining the level of CHCM1 protein or CHCM1 nucleic acid comprises performing an assay, wherein the assay is immunohistochemical staining, Western blotting, immunoprecipitation, protein pull-down, Northern or dot blotting, or a microarray procedure, or a modification thereof on the sample, wherein the assay comprises using an antibody specific for a CHCM1 protein, using a nucleic acid that binds to a CHCM1 nucleic acid, or using a peptide that binds to a CHCM1 protein, and wherein the assay detects CHCM1 expression.

4. The method of claim 3, wherein determining the level of CHCM1 nucleic acid comprises detecting a level of mRNA for CHCM1 in the sample.

5. A method for treating a patient being administered vemurafenib comprising:
  obtaining a biological sample from the patient being administered vemurafenib;
  determining a level of Coiled Coil Helix Cristae Morphology 1 (CHCM1) protein or nucleic acid expression in the biological sample; and
  provided that the biological sample expresses at least a 1.5-fold higher level of CHCM1 than matching normal tissue, administering to the patient a genotoxic anti-cancer compound for reducing the expression of CHCM1, for blocking or inhibiting function of CHCM1, or for blocking or inhibiting CHCM1 interactions with other proteins.

6. The method of claim 5, wherein the patient exhibits resistance to vemurafenib.

7. A method for diagnosing and treating a cancer or a tumor in a patient, wherein the cancer or the tumor harbors a vemurafenib-sensitive BRAF mutation comprising:
  obtaining a biological sample from a patient;
  determining a level of Coiled Coil Helix Cristae Morphology 1 (CHCM1) protein or CHCM1 nucleic acid in the sample;
  testing the biological sample for presence of a vemurafenib-sensitive BRAF mutation; and
  provided that the biological sample tests positive for presence of a vemurafenib-sensitive BRAF mutation, and provided that the sample expresses at least a 1.5-fold higher level of CHCM1 protein or CHCM1 nucleic acid than a level of CHCM1 protein or CHCM1 nucleic acid in matching normal tissue, administering vemurafenib and a genotoxic anti-cancer compound to the patient, wherein the genotoxic anti-cancer compound reduces the expression of CHCM1, blocks or inhibits function of CHCM1, or blocks or inhibits CHCM1 interactions with other proteins.

8. The method of claim 7, wherein the vemurafenib-sensitive BRAF mutation is a V600 BRAF mutation.

9. A method for diagnosing and treating a cancer or a tumor expressing a vemurafenib-insensitive BRAF mutation or a BRAF wild-type gene in a patient comprising:
  obtaining a biological sample from a patient;
  determining a level of Coiled Coil Helix Cristae Morphology 1 (CHCM1) protein or nucleic acid in the sample;
  testing the sample for presence of a vemurafenib-sensitive BRAF mutation or a wild-type BRAF gene; and
  provided that the sample tests negative for presence of the vemurafenib-sensitive BRAF mutation or tests positive for the wild-type BRAF gene, and provided that the biological sample expresses at least a 1.5-fold higher level of CHCM1 protein or CHCM1 nucleic acid than a level of CHCM1 protein or CHCM1 nucleic acid in matching normal tissue, administering to the patient a genotoxic anti-cancer compound for reducing expression of CHCM1, for blocking or inhibiting function of CHCM1, or for blocking or inhibiting CHCM1 interactions with other proteins.

10. A method for determining whether efficacy of a therapeutic compound for treatment of a cancer or a tumor in a patient can be enhanced by decreasing a level of expression of Coiled Coil Helix Cristae Morphology 1 (CHCM1), comprising:
  obtaining a biological sample from a patient; and
  determining a level of expression of CHCM1 protein or CHCM1 nucleic acid in the biological sample,
  wherein if the biological sample expresses at least a 1.5-fold higher level of expression of CHCM1 protein or CMCH1 nucleic acid than a level of expression of CHCM1 protein or CHCM1 nucleic acid in
  matching normal tissue, determining that the efficacy of the therapeutic compound can be enhanced by decreasing the level of expression of CHCM1,
  the cancer is breast cancer, colon cancer, melanoma, lung cancer, testicular cancer, or thyroid cancer, and
  the tumor is a breast tumor, colon tumor, melanoma tumor, lung tumor, testicular tumor, or thyroid tumor.

11. A method for treating a cancer or a tumor in a patient comprising:
  requesting a test of a patient, wherein the test compares a level of Coiled Coil Helix Cristae Morphology 1 (CHCM1) protein or CHCM1 nucleic acid in a biological sample of suspected cancer or tumor tissue from the patient to a level of CHCM1 protein or CHCM1 nucleic acid in matching normal tissue; and
  provided that the sample expresses at least a 1.5-fold higher level of CHCM1 protein or CHCM1 nucleic acid than the level of CHCM1 protein or CHCM1 nucleic acid in the matching normal tissue,
  administering a cancer treatment or a tumor treatment to the patient,
  wherein:
  the cancer is breast cancer, colon cancer, melanoma, lung cancer, testicular cancer, or thyroid cancer, and
  the tumor is a breast tumor, colon tumor, melanoma tumor, lung tumor, testicular tumor, or thyroid tumor.

12. A method for determining whether efficacy of a therapeutic compound for treatment of a cancer or a tumor in a patient can be enhanced by decreasing a level of expression of Coiled Coil Helix Cristae Morphology 1 (CHCM1), wherein the cancer or tumor is characterized by a level of a CHCM1 biomarker, wherein the CHCM1 biomarker is a protein or nucleic acid, the method comprising:
  i) obtaining a biological sample from a patient;
  ii) determining a level of expression of CHCM1 by applying an antibody specific for the CHCM1 biomarker or for a substance that binds to the CHCM1 biomarker to create a complex with the CHCM1 biomarker;
  iii) assaying for the level of CHCM1 expression in the sample by applying a detection agent that detects the complex; and
  iv) provided that the detection agent of iii) is detected, and provided that the sample expresses at least a 1.5-fold higher level of the complex than a level of the complex in matching normal tissue, determining that the efficacy of the therapeutic compound can be enhanced by decreasing the level of expression of CHCM1,
  wherein:
  the cancer is breast cancer, colon cancer, melanoma, lung cancer, testicular cancer, or thyroid cancer, and
  the tumor is a breast tumor, colon tumor, melanoma tumor, lung tumor, testicular tumor, or thyroid tumor.

13. The method of claim 1, wherein the genotoxic anti-cancer compound is dacarbazine (DTIC), etoposide, cisplatin or doxorubicin.

* * * * *

SEQUENCE LISTING

<160> NUMBER OF SEQ ID NOS: 11

<210> SEQ ID NO 1
<211> LENGTH: 984
<212> TYPE: DNA
<213> ORGANISM: Homo sapiens

<400> SEQUENCE: 1

```
ctcgggtctg gtggctgccg gccctgcggc atctcgccat ggggagcacg gagagcagcg      60
agggccgcag ggtgtccttc ggagtggacg aggaggagcg ggtccgggtg ctgcagggtg     120
tccggctgtc tgaaaacgtg gtgaaccgca tgaaggagcc cagctctcca cccctgctc     180
ccacatcttc tacctttggc cttcaagatg gcaacttgag agcccctcac aaagaatcca     240
cactgcccag gtcggggagc agtggtggcc agcagccctc agggatgaag gagggtgtca     300
agaggtatga acaggagcat gctgctatcc aggataagct cttccaggtg gcaaagaggg     360
aaagagaggc tgccaccaag cactccaagg catccctgcc cacgggcgaa ggcagcatca     420
gccatgagga gcagaagtca gtccggctgg ccagggagct ggagagcaga gaggcagagc     480
taagacgccg tgacaccttc tacaaggagc agctggagcg tattgagagg aagaatgctg     540
agatgtataa actgtcttca gagcaattcc atgaggcagc ctcaaagatg gagagcacaa     600
taaagccccg cagggtggag cccgtctgct caggggttgca ggcccagatt ctccactgct     660
accgagatcg cccgcatgag gtgctgctgt gctcggacct ggtcaaggca taccagcgct     720
gcgtgagcgc cgcccacaag ggctgaggag cagacatcat tccctgccct ggcagtgact     780
tggagccctg aagaagggac caatcatggg accacagcca ctgtgccctg ccgtttcctg     840
ctgggcccct gcatatgccc ctgagcctgg ggctgccacg tgtttaggaa acaaagtatg     900
cgctactgtc tgaaaacaaa taaagcagat gcctttgttt tcagtcaaaa aaaaaaaaa     960
aaaaaaaaa aaaaaaaaaa aaaa                                            984
```

<210> SEQ ID NO 2
<211> LENGTH: 235
<212> TYPE: PRT
<213> ORGANISM: Homo sapiens

<400> SEQUENCE: 2

```
Met Gly Ser Thr Glu Ser Ser Glu Gly Arg Arg Val Ser Phe Gly Val
1               5                   10                  15

Asp Glu Glu Glu Arg Val Arg Val Leu Gln Gly Val Arg Leu Ser Glu
            20                  25                  30

Asn Val Val Asn Arg Met Lys Glu Pro Ser Ser Pro Pro Ala Pro
        35                  40                  45

Thr Ser Ser Thr Phe Gly Leu Gln Asp Gly Asn Leu Arg Ala Pro His
    50                  55                  60

Lys Glu Ser Thr Leu Pro Arg Ser Gly Ser Ser Gly Gly Gln Gln Pro
65                  70                  75                  80

Ser Gly Met Lys Glu Gly Val Lys Arg Tyr Glu Gln Glu His Ala Ala
                85                  90                  95

Ile Gln Asp Lys Leu Phe Gln Val Ala Lys Arg Glu Arg Glu Ala Ala
            100                 105                 110

Thr Lys His Ser Lys Ala Ser Leu Pro Thr Gly Glu Gly Ser Ile Ser
        115                 120                 125

His Glu Glu Gln Lys Ser Val Arg Leu Ala Arg Glu Leu Glu Ser Arg
    130                 135                 140
```

```
Glu Ala Glu Leu Arg Arg Arg Asp Thr Phe Tyr Lys Glu Gln Leu Glu
145                 150                 155                 160

Arg Ile Glu Arg Lys Asn Ala Glu Met Tyr Lys Leu Ser Ser Glu Gln
                165                 170                 175

Phe His Glu Ala Ala Ser Lys Met Glu Ser Thr Ile Lys Pro Arg Arg
            180                 185                 190

Val Glu Pro Val Cys Ser Gly Leu Gln Ala Gln Ile Leu His Cys Tyr
        195                 200                 205

Arg Asp Arg Pro His Glu Val Leu Leu Cys Ser Asp Leu Val Lys Ala
    210                 215                 220

Tyr Gln Arg Cys Val Ser Ala Ala His Lys Gly
225                 230                 235

<210> SEQ ID NO 3
<211> LENGTH: 49
<212> TYPE: DNA
<213> ORGANISM: Artificial Sequence
<220> FEATURE:
<223> OTHER INFORMATION: Synthetic sequence

<400> SEQUENCE: 3
gagcgtattg agaggaagaa tctcgagatt cttcctctca atacgctct              49

<210> SEQ ID NO 4
<211> LENGTH: 49
<212> TYPE: DNA
<213> ORGANISM: Artificial Sequence
<220> FEATURE:
<223> OTHER INFORMATION: Synthetic sequence

<400> SEQUENCE: 4
cctgaagaag ggaccaatca tctcgagatg attggtccct tcttcaggt              49

<210> SEQ ID NO 5
<211> LENGTH: 49
<212> TYPE: DNA
<213> ORGANISM: Artificial Sequence
<220> FEATURE:
<223> OTHER INFORMATION: Synthetic sequence

<400> SEQUENCE: 5
gcatgctgct atccaggata actcgagtta tcctggatag cagcatgct              49

<210> SEQ ID NO 6
<211> LENGTH: 49
<212> TYPE: DNA
<213> ORGANISM: Artificial Sequence
<220> FEATURE:
<223> OTHER INFORMATION: Synthetic sequence

<400> SEQUENCE: 6
ctttggcctt caagatggca actcgagttg ccatcttgaa ggccaaagt              49

<210> SEQ ID NO 7
<211> LENGTH: 49
<212> TYPE: DNA
<213> ORGANISM: Artificial Sequence
<220> FEATURE:
<223> OTHER INFORMATION: Synthetic sequence

<400> SEQUENCE: 7
gctgagatgt ataaactgtc tctcgagaga cagtttatac atctcagct              49
```

```
<210> SEQ ID NO 8
<211> LENGTH: 59
<212> TYPE: DNA
<213> ORGANISM: Artificial Sequence
<220> FEATURE:
<223> OTHER INFORMATION: Synthetic sequence

<400> SEQUENCE: 8
ccgggctaag gttgtatctc agtatctcga gatactgaga tacaacctta gctttttg        59

<210> SEQ ID NO 9
<211> LENGTH: 59
<212> TYPE: DNA
<213> ORGANISM: Artificial Sequence
<220> FEATURE:
<223> OTHER INFORMATION: Synthetic sequence

<400> SEQUENCE: 9
ccggccaagc tttaaccgca gctatctcga gatagctgcg gttaaagctt ggtttttg        59

<210> SEQ ID NO 10
<211> LENGTH: 59
<212> TYPE: DNA
<213> ORGANISM: Artificial Sequence
<220> FEATURE:
<223> OTHER INFORMATION: Synthetic sequence

<400> SEQUENCE: 10
ccgggcacta tcctatatgc caaatctcga gatttggcat ataggatagt gctttttg        59

<210> SEQ ID NO 11
<211> LENGTH: 59
<212> TYPE: DNA
<213> ORGANISM: Artificial Sequence
<220> FEATURE:
<223> OTHER INFORMATION: Synthetic sequence

<400> SEQUENCE: 11
ccgggtctag aaatgagcag gtttactcga gtaaacctgc tcatttctag acttttttg       59
```